(12) United States Patent
Becker et al.

(10) Patent No.: US 6,641,708 B1
(45) Date of Patent: Nov. 4, 2003

(54) METHOD AND APPARATUS FOR FRACTIONATION USING CONVENTIONAL DIELECTROPHORESIS AND FIELD FLOW FRACTIONATION

(75) Inventors: Frederick F. Becker, Houston, TX (US); Peter R. C. Gascoyne, Belaire, TX (US); Ying Huang, San Diego, CA (US); Xiao-Bo Wang, San Diego, CA (US); Jun Yang, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/378,874

(22) Filed: Aug. 23, 1999

Related U.S. Application Data

(63) Continuation-in-part of application No. 08/604,779, filed on Jan. 31, 1996, now Pat. No. 5,993,630.
(60) Provisional application No. 60/010,904, filed on Jan. 31, 1996.

(51) Int. Cl.⁷ .................... G01N 27/26; G01N 27/447
(52) U.S. Cl. ........................ 204/547; 204/643
(58) Field of Search ................ 204/547, 643

(56) References Cited

U.S. PATENT DOCUMENTS

| | | | |
|---|---|---|---|
| 5,039,426 A | * 8/1991 | Giddings | 210/695 |
| 5,133,844 A | 7/1992 | Stevens | 204/180.1 |
| 5,344,535 A | * 9/1994 | Betts et al. | 204/547 |

FOREIGN PATENT DOCUMENTS

| | | |
|---|---|---|
| WO | WO 97/27933 | 8/1997 |
| WO | WO 98/09161 | 3/1998 |

OTHER PUBLICATIONS

M. Stephens et al. "The dielectrophoresis enrichment of CD34⁺ cell from peripheral blood stem cell Harvests" Bone Marrow Tranplantation, vol. 18, No. 4 (Oct. 1996) 777–784.*

J. Calvin Giddings "Field–Flow Fractionation: Analysis of Macromolecular, Colloidal, and Particulate Materials" Science, vol. 260 (Jun. 4, 1993) 1456–1465.*

Joe M. Davis and J. Calvin Giddings, "Feasibility Study of Dielectrical Field Flow Fractionation", Separation Science and Technology, 21(9), (1986) 969–989.*

Harold Ackler et al. "Microfluidic Systems for Electrochemical and Biological Studies" Electrochemical Society Proceeding, vol. 98–14, (Nov. 1998) 54–61. Nov. 1998.*

Davis and Giddings, "Feasiblity study of dielectrical field–flow fractionation," *Separation Science and Technology*, 21(9):969–989, 1986.

Ratanathanawongs and Giddings, "Dual–field and flow–programmed lift hyperlayer field–flow fractionation," *Anal. Chem.*, 64:6–15, 1992.

Yang et al., "Cell separation on microbabircated electrodes using dielectrophoretic/gravitational field–flow fractionation," *Anal. Chem.*, 71:911–918, 1999.

(List continued on next page.)

*Primary Examiner*—Jill Warden
*Assistant Examiner*—John S. Starsiak, Jr.
(74) *Attorney, Agent, or Firm*—Fulbright & Jaworski LLP

(57) ABSTRACT

Methods and apparatus for discriminating matter in a chamber having an inlet port and an outlet port utilizing dielectrophoresis and field flow fractionation. A carrier medium is introduced into the inlet port and is directed from the inlet port to the outlet port according to a velocity profile. A programmed voltage signal is applied to an electrode element coupled to the chamber to form a dielectrophoretic force on the matter. The dielectrophoretic force is balanced with a gravitational force to displace the matter to positions within said velocity profile in the carrier medium to discriminate the matter. A chamber having a top and bottom outlet port may be utilized to withdraw a first portion of a carrier medium from the top outlet port at a first, controllable fluid flow rate and to withdraw a second portion of the carrier medium from the bottom outlet port at a second, controllable fluid flow rate.

40 Claims, 36 Drawing Sheets

OTHER PUBLICATIONS

Becker et al., "The removal of human leukaemia cells from blood using interdigitated microelectrodes," *J. Phys. D: Appl. Phys.*, 27:2659–2662, 1994.

Becker et al., "Separation of human breast cancer cells from blood by differential dielectric affinity," *Proc. Natl. Acad. Sci.*, 92:860–864, 1995.

Gascoyne et al., "Use of dielectrophoretic collection spectra for characterizing differences between normal and cancerous cells," *IEEE. Trans. Ind. Appl.*, 30:829–834, 1994.

Gascoyne et al., "Dielectrophoretic separation of mammalian cells studied by computerized image analysis," *Meas. Sci. Technol.*, 3:439–445, 1992.

Gascoyne et al., "Cell separation by conventional dielectrophoresis combined with field–flow fractionation," *Biophys. J.*, 70:A330, 1996.

Gascoyne et al., "Dielectrophoretic separation of cancer cells from blood," *IEEE Trans. Ind. App. Soc.*, 33:670–678, 1997.

Huang et al., "Differences in the ac electrodynamics of viable and non–viable yeast cells determined through combined dielectrophoresis electrorotation studies," *Phys. Med. Biol.*, 37:1499–1517, 1992.

Huang et al., "Membrane changes associated with the temperature–sensitive P85$^{gag-mos}$–dependent transformation of rat kidney cells as determined by dielectrophoresis and electrorotation," *Biochim. Biophys. Acta 1282*, 76–84, 1996.

Huang et al., "Introducing dielectrophoresis as a new force field for field–flow fractionation," *Biophys. J.*, 73:1118–1129, 1997.

Huang et al., "Membrane dielectric responses of human T–lymphocytes following mitogenic stimulation," *Biochim. Biophys. Acta*, 1417:51–62, 1999.

Wang et al., "Selective dielectrophoretic confinement of bioparticles in potential energy wells," *J. Phys. D: Appl. Phys.* 26:1278–1285, 1993.

Wang et al., "Changes in friend murine erythroleukaemia cell membranes during induced differentiation determined by electrorotation," *Biochim. Biophys. Acta*, 1193:330–344, 1994.

Wang et al., "Non–uniform spatial distributions of both the magnitude and phase of ac electric fields determine dielectrophoretic forces," *Biochim. Biophys. Acta*, 1243:185–194, 1995.

Wang et al., "A theoretical method of electrical field analysis for dielectrophoretic electrode arrays using Green's theorem," *J. Phys. D: Appl. Phys.*, 29:1649–1660, 1996.

Wang et al., "Dielectrophoretic manipultation of particles," *IEEE Trans. Ind. Appl.*, 33:660–669, 1997.

Wang et al., "Separation of polystyrene microbeads using dielectrophoretic/gravitational field–flow fractionation," *Biophys. J.*, 74:2689–2701, 1998.

Yang et al., "Dielectric properties of human leukocyte subpopulations determined by electrorotation as a cell separation criterion," *Biophys. J.*, 76:3307–3314, 1999.

* cited by examiner

*Fixed Frequency, Amplitude*

*Fixed Amplitude, Three Frequencies: f1, f2, f3*

*Fixed Frequency, Three Amplitudes: V1, V2, V3*

Five different amplitude/frequency combination

Three different amplitude frequency-modulation combination

Three different amplitude frequency-modulation combination

METHOD AND APPARATUS FOR FRACTIONATION USING CONVENTIONAL DIELECTROPHORESIS AND FIELD FLOW FRACTIONATION

The present application is a continuation-in-part of U.S. patent application Ser. No. 08/604,779 filed Jan. 31, 1996, now U.S. Pat. No. 5,993,630 which claims priority to U.S. Provisional Application Ser. No. 60/010,904 filed Jan. 31, 1996. The entire text of each of the above-referenced disclosures is specifically incorporated by reference herein without disclaimer.

BACKGROUND OF THE INVENTION

1. Field of the Invention

The present invention relates generally to the fields of molecular separation and particle discrimination. More particularly, it concerns the fractionation of particulate matter utilizing a combination of electrical, hydrodynamic or gravitational forces.

2. Description of the Related Art

The ability to identify, characterize and purify cell subpopulations is fundamental to numerous biological and medical applications, often forming the starting point for research protocols and the basis for current and emerging clinical protocols. Cell separation has numerous applications in areas such as medicine, biotechnology, biomedical research, environmental monitoring and bio/chemical warfare defense. For example, cell separation can make possible life-saving procedures such as autologous bone marrow transplantation for the remediation of advanced cancers where the removal of cancer-causing metastatic cells from a patient's marrow is necessitated (Fischer, 1993). In other applications, such as the study of signaling between blood cells (Stout, 1993; Cantrell et al., 1992), highly purified cell subpopulations permit studies that would otherwise be impossible. Current approaches to cell sorting most frequently exploit differences in cell density (Boyum, 1974), specific immunologic targets (Smeland et al., 1992), or receptor-ligand interactions (Chess et al., 1976) to isolate particular cells.

These techniques are often inadequate and sorting devices capable of identifying and selectively manipulating cells through novel physical properties are therefore desirable. The application of the principles of AC electrokinetics has been used for the dielectric characterization of mammalian cells through the method of electrorotation (ROT) (Arnold and Zimmermann, 1982; Fuhr, 1985; Hölzel and Lamprecht, 1992; Wang et al., 1994) and for cell discrimination and sorting (Hagedorn et al., 1992; Huang et al., 1993; Gascoyne et al., 1992; Gascoyne et al., 1994; Huang et al., 1992). In these techniques, cells become electrically polarized when they are subjected to an AC electric field. In ROT, a rotational electrical field is applied and the interaction between the cells' polarization and the applied field results in cell rotation. If that field is inhomogeneous, then the cells experience a lateral dielectrophoretic (DEP) force, the frequency response of which is a function of their intrinsic electrical properties (Gascoyne et al., 1992). In turn, these properties depend strongly on cell composition and organization, features that reflect cell morphology and phenotype. Cells differing in their electrical polarizabilities can thus experience differential forces in the inhomogeneous electric field (Becker et al., 1994; Becker et al., 1995). Analysis of the dielectrophoretic motion of mammalian cells as a function of applied frequency permits cell membrane biophysical parameters, such as capacitance and surface conductance, to be probed. Because DEP effectively maps biophysical properties into a translational force whose direction and magnitude reflects cellular properties, DEP force may induce separation between particles of different characteristics. For example, DEP has been used on a microscopic scale to separate bacteria from erythrocytes (Markx et al., 1994), viable from nonviable yeast cells (Wang et al., 1993), and erythroleukemia cells from erythrocytes (Huang et al., 1992). However, the differences in the electrical polarizabilities of the cell types in those various mixtures were greater than those to be expected in many typical cell sorting applications.

Field flow fractionation (FFF) has also been generally employed for separation of matter, utilizing particle density, size, volume, diffusivity, and surface charge as parameters (Giddings, 1993). The technique can be used to separate many different types of matter, from a size of about 1 nm to more than about 100 micrometers, which may include, for example, biological and non-biological matter. Separation according to field flow fractionation occurs by differential retention in a stream of liquid flowing through a thin channel. The FFF technique combines elements of chromatography, electrophoresis, and ultracentrifugation, and it utilizes a flow velocity profile established in the thin channel when the fluid is caused to flow through the chamber. Such velocity profile may be, for example, linear or parabolic. A field is then applied at right angles to the flow and serves to drive the matter into different displacements within the flow velocity profile. The matter being displaced at different positions within the velocity profile will be carried with the fluid flow through the chamber at differing velocities. Fields may be based on sedimentation, crossflow, temperature gradient, centrifugal forces, and the like. The technique suffers, however, from producing insufficiently pure cell populations, being too slow, or being too limited in the spectrum of target cells or other matter.

Thus, there exists a need in the art for highly discriminate separation of particulate matter, especially biological matter. Furthermore, such a technique should operate without physically modifying the structure of the matter to be separated. In addition, it should allow for the sensitive manipulation of such particles, which may include characterization and purification of desired matter from extraneous or undesired matter.

SUMMARY OF THE INVENTION

The present invention seeks to overcome these drawbacks inherent in the prior art by combining the use of frequency-dependent dielectric and conductive properties of particles with the properties of the suspending and transporting medium. As used herein, the term "matter" is intended to include particulate matter, solubilized matter, or any combination thereof. The invention provides a novel apparatus and novel methods by which different particulate matter and solubilized matter may be identified and selectively manipulated. These particles may also be fractionated or collected separately by changing the DEP force or the fluid flow characteristics. Utilizing the invention in this manner, particulate matter and solubilized matter may be discriminated and separated. The apparatus and methods of the present invention may discriminate many different types of matter simultaneously.

The present invention provides a method and apparatus for the discrimination of particulate matter and solubilized matter of different types. This discrimination may include, for example, separation, characterization, differentiation and manipulation of the particulate matter. According to the present invention, the particulate matter may be placed in liquid suspension before input into the apparatus. The discrimination occurs in the apparatus, which may be a thin, enclosed chamber. Particles may be distinguished, for example, by differences in their density, size, dielectric permittivity, electrical conductivity, surface charge, and/or surface configuration. In the case of the biological cells, they may be discriminated according to differences in their size, density, membrane electrical capacitance and conductance, interior conductivity and permittivity, and/or surface charges.

The methods according to the present invention may be used to discriminate particulate matter, including inorganic matter, such as minerals, crystals, colloidal, conductive, semiconductive or insulating particles and gas bubbles. The methods of the present invention may also be used to discriminate biological matter, such as cells, cell organelles, cell aggregates, nucleic acids, bacterium, protozoans, or viruses. Further, the particulate matter may be, for example, a mixture of cell types, such as fetal nucleated red blood cells in a mixture of maternal blood, cancer cells such as breast cancer cells in a mixture with normal cells, or red blood cells infested with malarial parasites. Additionally, the methods of the present invention may be used to discriminate solubilized matter such as a molecule, or molecular aggregate, for example, proteins, or nucleic acids.

Particles to be discriminated may be any size. However, the present invention is generally practical for particles between ~10 nm and ~1 mm, and may include, for example, chemical or biological molecules (including proteins, DNA and RNA), assemblages of molecules, viruses, plasmids, bacteria, cells or cell aggregates, protozoans, embryos or other small organisms, as well as non-biological molecules, assemblages thereof, minerals, crystals, colloidal, conductive, semiconductive or insulating particles and gas bubbles. For biological applications using living cells, the present invention allows cells to be separated without the need to alter them with ligands, stains, antibodies or other means. Cells remain undamaged, unaltered and viable during and following separation. Non-biological applications similarly require no such alteration. It is recognized however, that the apparatus and methods according to the present invention are equally suitable for separating such biological matter even if they have been so altered.

The apparatus may include, for example, a chamber. The chamber may have at least one inlet and one outlet port, an interior surface and an exterior surface. The chamber may further be designed to have structural characteristics so that a desired flow velocity profile is generated when a fluid is caused to flow through the chamber. The flow velocity profile refers to the fact that the fluid at different positions travels at differing velocities. The chamber may be rectangular in shape and may include, for example, a top wall, bottom wall and two side walls. In certain embodiments, the chamber may be constructed so that the top wall and bottom wall are of a much greater magnitude than the side walls, thereby creating a thin chamber capable of creating a velocity profile. For example, for a rectangular chamber having a width W, a height H and a length L where the condition W>>H is held, the velocity profile for a fluid flow in the chamber in the direction along its length can be described as follows (Pazourek and Chmelik, 1992), $$V(x, h) = 6(V_m)\frac{h}{H}\left(1 - \frac{h}{H}\right)\left(1 - \frac{\cosh(2\sqrt{3}(x - W/2)/H)}{\cosh(\sqrt{3}W/H)}\right) \quad (1)$$

where x is the distance from the chamber side wall (measuring horizontally) and h is the distance from the bottom wall (measuring vertically). The factor $<V_m>$ is the average velocity of the fluid traveling through the chamber. Equation (1) indicates that the fluid velocity follows a parabolic dependency on the vertical position in the chamber. Since W>>H, the fluid velocity expression in Equation (1) can be approximated as a parabolic dependency, as $$V(h) = 6(V_m)\frac{h}{H}\left(1 - \frac{h}{H}\right). \quad (2)$$

where the edge-effect along the chamber width is ignored. In such a flow profile, the fluid velocity increases with increasing distance from the chamber top or bottom walls. Fluid close to the top and bottom walls travels at near zero velocity; and that at the mid point between the top and bottom walls travels at the highest velocity.

In other embodiments, the chamber may be constructed so that the top wall and bottom wall are of a much smaller magnitude than the side walls, again creating a thin chamber capable of creating a velocity profile. In that case, the parameter h in equation (2) describes the horizontal distance in the chamber from a side wall and H is the width of the chamber. Alternately, the chamber may be of circular construction, triangular, rectangular, hexadecagonal, or of other geometrical shapes. In such cases, modified versions of equation (2) will apply as is known in the art of hydrodynamics. As such, the present invention is not intended to be limited to a particular geometric shape. The chamber according to the present invention may be constructed of many different materials, for example, glass, polymeric material, plastics, quartz, coated metal, or the like.

The chamber includes at least one electrode element adapted along a portion or all of the chamber walls. Each of these one or more electrode elements may be electrically connected to an electrical conductor, which in turn are connected to an electrical signal source. In the discussion which follows, the terms "electrode element" or "electrodes" will be used. As used herein, "electrode element" is a structure of highly electrically-conductive material over which an applied electrical signal voltage is constant. It is to be understood that these terms include all of the electrode configurations described below. An electrical signal generator, which may be capable of varying voltage, frequency, phase or all the three may provide at least one electrical signal to the electrode elements. The electrode elements of the present invention may include, for example, a plurality of electrode elements which may be connected to a plurality of electrical conductors, which in turn are connected to the electric signal generator.

The chamber according to the present invention may include a plurality of electrode elements which comprise an electrode array. As used herein, an "electrode array" is a collection of more than one electrode element in which each individual element may be displaced in a well-defined geometrical relationship with respect to one another. This array may be, for example, an interdigitated (or parallel) array, interdigitated castellated array, a polynomial array, plane electrode, or the like. Further, the array may be comprised of microelectrodes of a given size and shape, such as an interdigitated array. The electrode array may be adapted along any interior or exterior surface of the chamber. Alternately, it is envisioned that the electrode array may be incorporated into the material which comprises the chamber walls. In certain embodiments, the electrode array may be a multilayer array in which conducting layers may be interspersed between insulating layers. Further, the present invention may have a plurality of electrode arrays which may be adapted, for example, on opposing surfaces of the chamber. However, it may be possible to place the plurality of electrode arrays on adjacent surfaces or on all surfaces of the chamber. Fabrication of such an electrode array, depending on electrode dimensions, may use any of the standard techniques known in the art for patterning and manufacturing microscale structures.

For an interdigitated (parallel) array, the parallel electrode elements may be adapted to be substantially longitudinally or latitudinally along a portion of the chamber. Other configurations of electrode elements are contemplated by the present invention, such as electrode elements adapted at angles to the chamber. It is also possible to use a three-dimensional electrode element that may or may not be attached to the surface of the chamber. For example, electrode elements may be fabricated from silicon wafers, using the semiconductor microfabrication techniques known in the art. If the electrodes are adapted along the exterior surface of the chamber, it is envisioned that a means of transmitting energy into the chamber, such as a microwave transmitter may be present. The electrode elements may be configured to be on a plane substantially normal or parallel to a flow of fluid travelling through said chamber. However, it is to be understood that the electrode elements may be configured at many different planes and angles to achieve the benefits of the present invention.

When the electrode elements are energized by at least one electrical signal from the electrical signal generator, the electrode elements thereby create spatially inhomogeneous alternating electric field, which causes a DEP force on the particulate matter and solubilized matter. This DEP force may be a conventional DEP force (cDEP), or it may be a travelling wave DEP force (twDEP), or the combination of the both. The cDEP force may have components acting in a direction substantially normal to the electrode element plane, that is, the cDEP force may cause matter to move towards or away from this plane. In reference to the fluid traveling through the chamber, the DEP force may act substantially in a direction normal to the fluid flow. As used herein, "a direction normal to the fluid flow" means in a direction which is substantially non-opposing and substantially nonlinear to the flow of a fluid traveling through the chamber. This direction may be for example, vertically, sideways, or in another non-opposing direction. By effect of this DEP force, particulate matter and solubilized matter is displaced to different positions within the fluid, in particular within the flow velocity profile established in the chamber. This displacement may be relative to the electrode elements, or may relate to other references, such as the chamber walls.

It is noted that by altering phase of the alternating electrical signal, a second DEP force, known as traveling wave DEP (twDEP), is created. The cDEP force is dependent on the spatial inhomogeneity of the electric field and causes matter to move towards or away from regions of high electrical field strength. The twDEP force is dependent upon the phase distribution of the applied electric field, and caused matter to move towards or away from the direction of increasing phase values.

In the present invention, the cDEP force is dependent on the magnitude of the spatial inhomogeneity of the electric field and the in-phase (real) part of the electrical polarization induced in matter by the field. It is to be understood that the term "electrical polarization" is related to the well known Clausius-Mossotti factor, described below. This field-induced electrical polarization is dependent on the differences between the dielectric properties between the matter and the suspending medium. These dielectric properties include dielectric permittivity and electrical conductivity. Together, these two properties are known as complex permittivity. The cDEP force causes the matter to move towards or away from regions of high electrical field strength, which in an exemplary embodiment, may be towards or away from the electrode plane.

The equation for the time-averaged dielectrophoretic force in a non-uniform electrical field is (Wang et al., 1995):

$$F_{DEP}=2\pi\in_m r^3 Re(f_{CM})\nabla E_{rms}^2+2\pi\in_m r^3 Im(f_{CM})(E_{x0}^2\nabla\phi_x+E_{y0}^2\nabla\phi_y+E_{z0}^2\nabla\phi_z) \quad (3)$$

where $E_{rms}$ is the rms value of the electric field distribution, $E_{\alpha 0}$ and $\phi_\alpha$ ($\alpha$=x,y,z) are the magnitudes and phases of each field component. The parameters $E_{rms}$, $E_{\alpha 0}$ and $\phi_{60}$ are, in general, functions of spatial coordinates (x,y,z) and dependent on positions. Nevertheless for the sake of simplicity, the explicit spatial coordinates (x,y,z) have be omitted. The factor $f_{CM}$ is the well-known Clausius-Mossotti factor, defined as $$f_{CM} = (\varepsilon_p^* - \varepsilon_m^*)/(\varepsilon_p^* - 2\varepsilon_m^*),$$

where $\in_p^*$ and $\in_m^*$ are the complex permittivities of the matter and its suspending medium, respectively. Each complex permittivity is defined as $$\varepsilon^* = \varepsilon - i^\sigma/(2\pi f),$$

$\in$ and $\sigma$ are the permittivity and conductivity, respectively. The parameters is the frequency of the applied field, r is the radius of the matter on which the DEP force is acting. Equation (3) indicates that dielectrophoretic force in general consists of two components. The first component, cDEP (conventional dielectrophoretic) force component, is dependent on the real part $Re(f_{CM})$ (in-phase component) of the Clausius-Mossotti factor $f_{CM}$ and the magnitude non-uniformity factor $\nabla E_{rms}^2$ of the applied electric field. If the in-phase part of the Clausius-Mossotti factor is greater than zero, then the cDEP force component will move the matter towards the location of the strong field. If the in-phase part of the Clausius-Mossotti factor is less than zero, the cDEP force component will move the matter towards the location of the weak field. The second component, twDEP (traveling-wave dielectrophoretic) force component, is dependent on the imaginary part $Im(f_{CM})$ (out-of-phase component) of the Clausius-Mossotti factor $f_{CM}$ and the phase non-uniformity factor ($\nabla\phi_x$, $\nabla\phi_y$, and $\nabla\phi_z$) of the applied electric field. Depending on the polarity of $Im(f_{CM})$, the twDEP force component will tend to move the matter towards the direction of increasing or decreasing phase values ($\phi_x,\phi_y,\phi_z$) of the field components. Whether the matter experiences a cDEP force component, or a twDEP force component, or both, will depend upon the electrode geometry and the manner in which the electrical signals are applied.

In the present invention, the purpose of applying the DEP force is to cause particulate matter and solubilized matter to be displaced to different positions within the fluid flow velocity profile established in the chamber. Specifically, the DEP force is applied so that it acts in conjunction with other forces so that different types of particulate matter is equilibrated at different, characteristic positions within the flow profile (or solubilized matter will attain equilibrium concentration distribution within the flow profile). Examples of other forces that may be used in conjunction with the applied DEP force include gravitational forces, electrical forces and hydrodynamic lifting forces. Gravitational forces arise because of the density difference between the matter and its suspending medium. If the density of the matter is larger than that of the medium, the matter will experience a gravitational force pointing downwards. If the density of the matter is smaller than that of the medium, the matter will experience a gravitational force pointing upwards. An electrical force may be produced on the charged matter when a DC electrical field is established in the chamber. Hydrodynamic lifting forces refer to the forces acting on matter when it is close to a chamber wall and there is a fluid-velocity profile in the chamber (Williams et al., 1992). Such lifting forces tend to push the matter away from the chamber walls. The magnitude of the hydrodynamic lifting forces may depend on the size, density, shape of the matter, the density and viscosity of the medium, and the fluid-flow profile in the chamber. In some cases, the hydrodynamic lifting forces may be significant and may be of comparable magnitude to the gravitational forces and dielectrophoretic forces. In other cases, the hydrodynamic lifting forces may be much smaller than the dielectrophoretic forces and may play a negligible role in positioning matters in the hydrodynamic flow profile.

A feature of the present invention is that DEP forces are applied to the matter in combination with at least one other force so that matter having different properties (dielectric/electrical property, density property, charge property) will be positioned differently in the flow-velocity profile established in the chamber. In one embodiment, DEP forces may be balanced with gravitational forces so that different matter attains different equilibrium positions. In another embodiment, DEP forces may be balanced with gravitational forces plus the hydrodynamic lifting forces so as to influence the equilibrium positions of the matter. In another embodiment, DEP forces may be balanced by electrical forces to control the equilibrium positions of different matter. DEP and other forces depend on the properties of the matter (e.g. dielectric property, density, size, electrical charge etc), therefore, the balance of these forces and the resulting matter equilibrium positions (or displacement) are also dependent on the properties of the matter. The matter of different properties will be displaced to different positions within the chamber or within the flow-velocity profile. These equilibrium positions may also be referred as "levitation" or "levitation height". As used herein, "levitate" or "levitation height" means that matter is displaced at different levels with respect to the electrode elements, in any direction, or matter is equilibrated at different positions with respect to the electrode elements under the balance of DEP forces and other forces.

In one embodiment of the present invention, an interdigitated (or parallel) electrode array may be adopted on the bottom wall of the separation chamber. The geometry of the interdigitated electrode array is characterized by the electrode element width to electrode element spacing. In one embodiment, the electrode element width and spacing are the same and an electrical voltage is applied to the neighboring electrode elements. Under this condition, only the cDEP force component is present in DEP forces exerting on the matter in the chamber. This cDEP force mainly lies in the vertical direction, especially for positions some distances away from the chamber bottom wall. This force acting on a matter of the radius r can be approximated as (Huang et al., 1997; Wang et al., 1998).

$$F_{DEP} = 2\pi \epsilon_m r^3 Re(f_{CM}) U^2 A \exp(-2\pi h/d) \quad (4)$$

where U is the applied root-mean-squared (RMS) voltage, $\epsilon_m$ is the dielectric permittivity of the medium. The DEP forces fall approximately exponentially with height h above the electrode plane, with a decay constant that is characterized by the periodic distance d(=2*electrode-element-width+2*electrode-element-spacing) of the electrode array and a unit voltage force coefficient A. Thus, changing electrode element width and/or spacing may modify DEP forces acting on the matter. The DEP forces shown Equation (4) may be used to balance the gravitational forces acting on the matter to achieve positioning particulate matter at different heights from the electrode plane. The gravitation forces are given by $-4/3\pi r^3(\rho_p - \rho_m)$. Here $\rho_p$ and $\rho_m$ are the densities of the matter and its suspending medium, respectively, satisfying the relationship $\rho_p > \rho_m$. The balance of gravitational and DEP levitation forces positions the matter at a stable equilibrium height, given by $$h_{eq} = \frac{d}{4\pi} \ln\left( \frac{3\epsilon_m U}{2g} \frac{A Re(f_{CM})}{(\rho_p - \rho_m)} \right). \quad (5)$$

Thus, equilibrium levitation heights are dependent on the dielectric property (as characterized by the dielectric polarization factor, $Re(f_{CM})$) and density ($\rho_p$) of the matter, of the electrode dimensions (A and d), of the applied DEP field strength (U). The factor $Re(f_{CM})$ is also dependent on the frequency of the applied field. In this embodiment, the DEP force acts in combination with the gravitational forces, and the levitation height of the matter is in the vertical direction with respect to the electrode plane. In other embodiments, the DEP force may act in combination with other forces and the levitation height may not be along the vertical direction.

In another embodiment, the interdigitated electrode array may have different electrode width from electrode spacing. The DEP force may take different form from those shown in Equation (4). Thus, the ratio of electrode width to electrode spacing may be modified to change the particulate matter and solubilized matter levitation height. Specifically, by changing this ratio, the electric field which is created is thereby altered. When the electric field is thereby altered, in magnitude and/or inhomogeneity, the levitation height of the matter similarly change. This levitation need not be in a vertical direction, and may include displacement in a horizontal direction, for example.

Common electrical conductors may be used to connect the one or more sets of electrode elements to the signal generator. The common electrical conductors may be fabricated by the same process as the electrodes, or may be one or more conducting assemblies, such as a ribbon conductor, metallized ribbon or metallized plastic. A microwave assembly may also be used to transmit signals to the electrode elements from the signal generator. All of the electrode elements may be connected so as to receive the same signal from the generator. It is envisioned that such a configuration may require presence of a ground plane. More typically, alternating electrodes along an array may be connected so as to receive different signals from the generator. The electrical generator may be capable of generating signals of varying voltage, frequency and phase and may be, for example, a function generator, such as a Hewlett Packard generator Model No. 8116A. Signals desired for the methods of the present invention are in the range of about 0 to about 50 volts, and about 0.1 kHz to about 180 MHz, and more preferably between about 0 to about 15 volts, and about 10 kHz to 10 MHz. These frequencies are exemplary only, as the frequency required for matter discrimination is dependent upon the conductivity of for example, the cell suspension medium. Further, the desired frequency is dependent upon the characteristics of the matter to be discriminated. The variation of the frequency will generally alter the polarization factor (the Clausius-Mossotti factor) of the matter and change the DEP forces exerted on the matter. Thus to enhance the discrimination of matters using the present invention, the operational frequency may be chosen so as to maximize the difference in the DEP forces exerting on the matter or maximize the difference in the DEP force induced levitation height between different matter. In one embodiment of the invention using the interdigitated (parallel) electrode array, the levitation-height of the matter may be expressed in Equation (5). As an example, the operation frequency for discriminating two different matters (A and B) with such an embodiment of the invention may be chosen to maximize the levitation height difference $|h_{eqA} - h_{eqB}|$:

$$\underset{frequency}{\text{Max}} \; |h_{eqA} - h_{eqB}| \; \text{or} \qquad (6)$$

$$\underset{frequency}{\text{Max}} \left| \frac{d}{4\pi} \ln\left( \frac{(\rho_{pB} - \rho_m)Re(f_{CMA})}{(\rho_{pA} - \rho_m)Re(f_{CMB})} \right) \right|. \qquad (7)$$

Here the polarization factors $f_{CMA}$ and $f_{CMB}$ depend on the applied field frequency, the maximum discrimination may be found by scanning the frequency empirically. Alternatively, if the dielectric property of the matter A and B can be obtained from some other methods, then the discrimination frequency may then be predicted through theoretical calculation. For example, the dielectric properties of mammalian cells may be readily determined using the technique of electrorotation in which individual cells are subjected to a rotating electrical field and cells are caused to rotate as a result of the interaction between the rotating field and the field-induced polarization. The frequency spectra of cell rotations are obtained by measuring cell rotational rate as a function of the frequency and can be analyzed in terms of dielectric shell-models to obtain cell dielectric parameters. The use of electrorational method for cell dielectric characterization is known to those skilled in the art (Wang, X.-B. et al. 1995; Huang, Y. et al, 1996; Fuhr & Hagedorn, 1996). The dielectric parameters from electrorotational measurements may then be used to calculate the frequency dependency of cell polarization factor $f_{CM}$ and to determine the frequency using Formula (7) at which the discrimination between two cell types is maximized.

The discrimination between matters depends also on the shape, size and configuration of the electrode elements. The change in these variables may significantly alter electrical field distribution and affect DEP forces acting on matters. Thus, it may be, necessary to design different geometries of electrode array for different applications of the present invention. Electrode array may be, for example, an interdigitated (or parallel) array, interdigitated castellated array, a polynomial array, plane electrode, or the like. Further, the array may be comprised of microelectrodes of a given size and shape, such as an interdigitated array.

In an exemplary embodiment, the signals are sinusoidal, however it is possible to use signals of any periodic or aperiodic waveform. The electrical signals may be developed in one or more electrical signal generators which may be capable of varying voltage, frequency and phase. Furthermore, DEP forces acting on matters may be programmed and varied by electrical signals applied to electrode arrays so that the signal amplitude, frequency, waveforms, and/or phases are a function of the time. For example, the applied sinusoidal signal may have a frequency ($f_1$) for certain length of time and may then be changed to a frequency ($f_2$). Alternatively, electrical signals with frequency-modulation (frequency continuously changes with time) and amplitude-modulation (amplitude continuously changes with time) may be applied. The signals applied to electrode arrays can therefore be programmed according to the specific separation goals and the specific separation problems. By employing such programmed signals, the DEP force may be varied with time for enhancing separation performance and the discrimination of DEP-FFF separator may be tailed to specific applications.

A chamber according to the present invention may have at least one inlet and outlet port. These ports may be the same port, or the chamber may be constructed to have different ports. The inlet port may take the form of drilled holes on the major walls of the chamber at the positions close to the chamber inlet end. The inlet port would allow the introduction of the matter to be discriminated into the chamber. The matter may be suspended or solubilized in a liquid medium, and may be introduced into the chamber through an injection valve equipped with an injection loop. The use of such injection valve for introducing the matter to be discriminated is known to those skilled in the art, as typically employed in chromatography. The inlet port may also be used for the introduction of the medium into the chamber so to establish a flow velocity profile. The reference by Wang et al (1998) provided a detailed description of using an injection valve for introducing the matter to be discriminated and for introducing the medium through an inlet port.

The outlet port may be arranged to be vertically lower than the at least one inlet port. Such an arrangement thereby permits sedimentation of the particulate matter and solubilized matter as it travels throughout the chamber. In addition to the at least one inlet port and one outlet port, the chamber may also include one or more input ducts which allow the fluid to flow through the apparatus.

The outlet port of the chamber according to the present invention may take many forms. Specifically, the outlet port may be a single port, or a plurality of ports, or an array of ports. In one embodiment,the outlet port may be two ports and may be located on the two major facing walls at positions close outlet end of a rectangular chamber. Because the matters to be discriminated attain equilibrium levitation heights in the chamber and are transported through the chamber under the influence of the flow-velocity profile, the matters may exit the chamber from one of the two outlet ports and the carrier medium may exit the chamber from the other outlet port. The advantage of this approach would increase the concentration of the matters at the port where they exit the chamber so that the matters may be collected and analyzed. In another embodiment, the matters to be discriminated may exit the two outlet ports, i.e. one population of the matter from one outlet port and all the others from the second outlet port. This embodiment may further allow the continuous operation of the discrimination and separation of the matter using the present invention. The matters may continuously be introduced into the chamber through the inlet port, and upon their introduction into the chamber, the matters would experience dielectrophoretic forces and other operational forces (such as gravity and hydrodynamic lifting forces) and would be directed towards to different levitation heights within the chamber. At these heights, all the forces acting on the matters would balance each other and the net force would be zero. During this process of moving the matters to their equilibrium positions, the flow velocity profile would carry the matter through the chamber. Depending on their levitation positions in the profile, the matter would exit the chamber at one of the two outlet ports. Which of the two ports the matter may exit from would depend on DEP and other forces acting on the matter and thus depend on the properties of the matter, allowing the discrimination of the matter.

In another embodiment, the outlet port may be located along the entire width or a part of the width of the chamber. The outlet port may be adapted to receive the matters of various shapes and sizes. For example, the size of the outlet port may vary from approximately twice the size of the matter desired to be discriminated to the entire width of the chamber. In one embodiment, the outlet port may be constructed of one or more tubing elements, such as TEFLON tubing. The tubing elements may be combined to provide an outlet port having a cross section comprised of individual tubing elements. Further, for example, the outlet port may be connected to fraction collectors or collection wells which are used to collect separated matter. As used herein, "fraction collectors" and "collection wells" include storage and collection devices for discretely retaining the discriminated particulate matter and solubilized matter. Other components that may be included in the apparatus of the present invention are, for example, measurement or diagnostic equipment, such as flow cytometers, lasers, particle counters, particle impedance sensors, impedance analyzers, and spectrometers. These analytical instruments connected directly to the outlet port of the chamber may serve not only detection step for measuring and recording the time of the arrival of the particulate or solubilized matter but also analyzing step for characterizing the properties of the matter. For example, an AC impedance sensor may be connected to the outlet port of the chamber, and coupled with AC impedance sensing electronics, may serve an analytical step for determining the AC impedance of individual particles when they exit the separation chamber.

The matter being discriminated using the chamber of the present invention attains equilibrium positions within the chamber at which DEP and other forces (e.g. gravity or hydrodynamic lifting forces) balance each other. A fluid flow may be established in the chamber so to establish a flow velocity profile. After being displaced within such a fluid flow profile, the displaced matter may exit from the outlet port or ports at a time proportionate to the displacement of the matter within the fluid. Specifically, the matter equilibrated at different positions within the flow profile is carried by the fluid flow at different speeds or matter at different levels of displacement within the fluid travels at different speeds. Therefore, the matter is discriminated by its displacement within the fluid flow. Matters of different properties attain different equilibrium positions or are displaced at different levels within the fluid flow profile. Particulate matter and solubilized matter within the fluid flow velocity profile will travel through the chamber at velocities according to their positions within the velocity profile.

This velocity profile may be, for example, a hydrodynamic fluid profile such as a parabolic flow profile. For a chamber of a rectangular shape, the velocity profile may be determined by knowing the average fluid velocity, and the chamber width and thickness, as shown in Equations (1) and (2). The average fluid velocity may be calculated based on the flow rate of the fluid, and the chamber width and thickness, according to the equation:

$$\text{average fluid velocity} = (\text{flow rate})/(\text{chamber width} \times \text{chamber thickness}) \tag{8}$$

Parameters that determine the velocity profile of the fluid flow include (but are not limited to): the chamber width or thickness, which in a rectangular embodiment may be the distance between opposing walls; constrictions or expansions of the fluid flow path which may include, for example, those arising for a non-parallel disposition of opposing chamber walls, or from the presence of suitably-placed obstructions or vanes; surface roughness of the chamber walls; structural features of the chamber walls that give rise to periodic or aperiodic modifications of the thickness of the fluid stream, including the electrode elements and other surface structural configurations, and the geometrical form of the chamber which may be, for example, rectangular, circular, wedge-shaped, stepped, or the like.

In one embodiment of the present invention, an interdigitated (parallel) electrode array may be adopted on the bottom wall of a rectangular separation chamber. The matter to be discriminated is introduced into the chamber with appropriate electrical signals applied and is positioned at equilibrium heights with respect to the electrode elements under the influence of the DEP forces and the gravitational forces. Matters of different properties (e.g.: dielectric, density, size) are displaced to different heights, allowing the discrimination of the matter. Further, when a fluid flow profile such as those described in Equations (1) and (2) is generated in the chamber, the matter being displaced at different heights from the electrode plane is transported at different velocities under the influence of the fluid flow. For example, when a parabolic flow profile (along the vertical direction as in Equation (2)) is established, the matter being displaced to positions close to the half-height of the chamber travels at higher speeds than the matter being displaced to positions close to the chamber top and bottom walls. Thus the matter may be discriminated by such differing velocities. As an example, two particulate matters A and B are positioned at equilibrium heights $h_{eqA}$ and $h_{eqB}$ within a parabolic flow profile (along the vertical direction as in Equation (2)). Their velocities caused by the fluid flow are $$V_A = 6K_\alpha(V_m)\frac{h_{eqA}}{H}\left(1 - \frac{h_{eqA}}{H}\right), \text{ and} \tag{9}$$

$$V_B = 6K_\alpha(V_m)\frac{h_{eqB}}{H}\left(1 - \frac{h_{eqB}}{H}\right). \tag{10}$$

Here $K_\alpha$ is a factor which lies between 0 and 1, and it reflects the retardation effects due to the chamber wall (Williams et al, 1992). If the matter A is positioned higher than the matter B but less than the half chamber height H, $h_{eqB} < h_{eqA} < H$, then A would travel at larger velocity than B, $V_B < V_A$. Further, different matter, when introduced into the chamber at a fixed time, would take differing time to travel through the chamber and to exit the chamber outlet port. The matter having larger velocities would exit the chamber ahead of the matter having smaller velocities. For the matter A and B described above, the time they take to travel through the chamber of length L would be $$t_A = \frac{L}{V_A} \text{ and} \tag{11}$$

$$t_B = \frac{L}{V_B}. \tag{12}$$

Thus, the matter may be further discriminated and separated by such differential exit-time ($t_B > t_A$ since $V_B < V_A$). For the matter exiting the chamber earlier may be collected separately from those exiting the chamber later, allowing the matter separation and discrimination. In another embodiment of an apparatus according to the present invention, a chamber may have two facing electrode arrays adapted on opposing surfaces. The chamber may be oriented so that the electrode planes stand substantially vertical and the thin sides of the chamber are vertically arranged. It is understood, however, that the electrode planes need not be only vertical, and the present invention contemplates adapting the apparatus at varying angles. Different electrical signals (frequency and magnitude) may be applied to the facing electrodes from the signal generator so that particles experience different cDEP forces. Further, within each electrode array, each alternate element may receive different electrical signals to create an inhomogeneous alternating electric field.

This further embodiment may have, for example, one inlet port adapted to receive the particulate matter to be discriminated. The inlet port may be located, for example, close to the top of one end of the chamber. This apparatus may also include one or more ducts to introduce a fluid that travels through the chamber. The ducts, which may be arranged substantially along the entire width of the input end of the chamber, serve to introduce a sheet of fluid that travels throughout the chamber in a substantially linear direction. As used herein, a "sheet" of fluid may be a flow of fluid or gas entering the chamber at a substantially uniform fluid velocity. The uniform distribution in the fluid velocity here refers to that the fluid velocity does not vary with positions along the entire width of the input end of the chamber. However, the fluid velocity may be a function of the distance from electrode planes located at two major, facing walls. The introduced "sheet" fluid carries the particulate matter through the chamber. Following transit through the chamber, fluid leaves at the opposite end. This exit end of the chamber may include, for example, one or more exit ports, which may be arranged in one or more arrays of exit ports. The outlet port may be constructed so that matter having different lateral positions at one vertical level may be separately discriminated. For example, it may be possible to utilize a laser as a tool to determine characteristics of matter exiting at selected lateral positions.

Different electrical signals (frequency or magnitude or both) are applied to electrode elements located on each of the side walls. There is a synergistic interaction between these different electrical signals which creates an inhomogeneous electric field. Particulate matter to be discriminated is subjected to DEP forces ($F_{DEP1}$ and $F_{DEP2}$) from electrical fields induced from electrode elements located on both the side walls, $$F_{total} = F_{DEP1} + F_{DEP2}. \quad (13)$$

Under the combined influence of these forces, the matter is directed equilibrium positions with respect to the side-walls. The equilibrium position, defined as the distances from the two side-walls, is therefore determined by DEP forces on the particulate matter. Since both DEP force components are dependent on the dielectric and conductive properties of the matter, this equilibration position depends on these properties of the matter. Other factors influencing the equilibrium positions include the magnitude and frequency of the electrical fields applied to the electrodes on the opposing chamber walls, the fluid density, viscosity, and flow rate. Different matter, because of their different properties, equilibrates at different characteristic distances from the side-walls of the chamber and attains different equilibrium positions based on this synergistic interaction of the DEP forces induced by the differing electrical signals. When a fluid flow is established in the chamber, the velocity of the different matter within the fluid is controlled by the velocity profile of the fluid and the equilibrium position of the matter with in the flow-velocity profile. This velocity profile has a maximum velocity towards the center of the chamber, with this velocity proportionately diminishing as distance from the side-walls decreases. Because of this velocity profile, matter that has equilibrated at different equilibrium distances from the chamber walls will be carried at different velocities and therefore take varying amounts of time to traverse the chamber. Those skilled in the art would appreciate that the equations describing the velocity and the transit time of matter through the chamber under the influence of the fluid flow are similar to Equations (9, 10, 11, 12).

The distance that matter sediments during its passage across the chamber will depend upon its transit time, as gravitational forces act on the matter during its transit through the chamber, and this is known as a "sedimentation effect." For a spherical particle having a radius r and density $\rho_p$, the sedimentation velocity $V_{sed}$ in a medium having a density $\rho_m$ and viscosity $\eta_m$ can be written as $$V_{sed} = \frac{2\ r^2(\rho_p - \rho_m)}{9\eta_m}. \quad (14)$$

The sedimentation velocity is a function of the particle size and density, medium viscosity and density. Consequently, different particles will sediment to different depths ($D_{sed}$) based upon the sedimentation velocity ($V_{sed}$) and the transit time ($t_{transit}$) of matter through the chamber, $$D_{sed} = V_{sed} \times t_{transit}. \quad (15)$$

Thus, particle sedimentation depends on matter characteristics, such as size, mass, and volume, for example. As described above, the time ($t_{transit}$) required for particles to travel across the entire length of the chamber is controlled by the fluid flow profile and the positions of particles within the flow-velocity profile. The placement of particles within the fluid flow profile is in turn determined by the synergism of the differing electrical signals. Thus, particles with different characteristics (e.g.: dielectric property, size) may be placed at different positions in the flow profile and therefore exhibit different transit times. The combination of differences in transit time and in sedimentation velocity between particles of different properties (e.g. dielectric property, density, size) may lead to different sedimentation depths for these particles. They may exit the chamber through different outlet ports which may be placed at different heights with respect to the inlet ports. Discrimination may be accomplished either in "batch mode" or in "continuous mode." In batch mode, an aliquot of particles is injected and collected with respect to the time of transit ($t_{transit}$) for the particles and the height of exit ($D_{sed}$) at the outlet ports. In continuous mode, a constant stream of particles is injected into the inlet port, and matter emerging at different heights ($D_{sed}$) are continuously collected.

The methods and apparatus of the present invention introduce for the first time the use of the frequency-dependent dielectric and conductive properties of particles as well as those of the suspending medium. These new criteria for particle fractionation allow sensitive manipulation of particles because the dielectrophoretic force is large and strongly dependent on particle properties. Appropriate choices of the suspending medium and applied field conditions allow for high levels of discrimination.

Previously reported field flow fractionation techniques have limitations for biological samples because of the narrow range of cell densities, demanding complex centrifuges and centrifugation techniques for good discrimination. The cDEP affinity method demands large differences in the dielectric characteristics of the particles to be separated so that selected particulate matter and solubilized matter can be completely immobilized while others are swept away by fluid flow forces. Since, for biological cells, damage can occur at high electric field strengths, there is a practical limitation to the maximum cDEP force that can be applied and this in turn limits the maximum fluid flow rate in the cDEP affinity approach. This may result in a slow cell sorting-rate. In the methods of the present invention, these limitations are substantially reduced. Furthermore, the cDEP affinity method of the prior art utilizes the dielectrophoretic force component that generally immobilizes particles on electrode elements. The cDEP/FFF approach of the present invention utilizes the DEP forces and other forces to determine the positions of particles or other matter in a flow-velocity profile and exploits the flow-velocity profile.

Also, in the present invention, the flow profile is an active mechanism for the separation and discrimination of particles, and the dielectrophoretic force (mainly the force component in the direction normal to the fluid flow direction), in conjunction with other forces (e.g. gravity, hydrodynamic lifting force, or another dielectrophoretic force), is the primary means by which the heights or positions of particles in the fluid flow profile are controlled. As discussed above, the fluid profile may be controlled by apparatus design, fluid rate, density and the like. By combining FFF and dielectrophoretic forces, the present invention takes advantage of particle volume and density in synergism with the frequency-dependent particle dielectric and conductive properties as well as surface configuration. The operation of an apparatus according to the present invention may be controlled by varying experimental conditions including, but not limited to, the particle suspending medium conductivity and permittivity, the fluid flow rate, viscosity and density, the applied electrical field strength, the applied frequency and the applied electrical signal waveform. This utilization of many parameters in setting the operational conditions for fractionation greatly increases the ability to discriminate between different particulate matter and solubilized matter. In the methods according to the present invention, particles emerging from the outlet ports of the apparatus may be collected, for example, by one or more fraction collectors, or may be fed directly into analytical apparatus such as flow cytometer or impedance sensors to characterize separated particles. Furthermore, when necessary or desired, particles may be transferred to collection wells containing appropriate solutions or media, such as neutral salt buffers, tissue culture media, sucrose solutions, lysing buffers, solvents, fixatives and the like. In the case of biological cells, the collected, separated cells may be further cultured and analyzed for their molecular characteristics. Alternatively, the separated cells may be subjected to other molecular, biochemical studies.

In an illustrative embodiment, the chamber may be constructed in a rectangular shape using, for example, two glass slides as chamber walls. These chamber walls may be spaced apart by spacers to create the rectangular design. These spacers may be made of, for example, glass, polymeric material such as TEFLON, or any other suitable material. The size of the chamber and spacing between chamber walls is dependent on the size of the particles which are to be discriminated. To practice the methods of the present invention, an apparatus may have spacing between about 100 nm and about 10 mm, and more preferably between about 20 microns and about 600 microns in an illustrative embodiment for the purpose of discriminating mammalian cells. Further, a longer chamber may be desired to permit greater discrimination throughput. An apparatus according to the present invention can discriminate cells at a rate between about 100 and about 3 million cells per second. Factors that determine discrimination rate include, for example, the dielectric properties of the particles to be discriminated, the electrode design, length of the chamber, fluid flow rate, frequency and voltage of the electrical signals, and the signal waveforms. The chamber dimensions may be chosen to be appropriate for the input matter type, characteristics, and degree of discrimination desired or required.

In other embodiments, one or more surfaces of the chamber may support an electrode array. The electrode array may be a microelectrode array of, for example, parallel electrode (interdigitated) elements. In certain embodiments, the parallel electrode elements may be spaced about 20 microns apart. The apparatus may accommodate electrode element widths of between about 0.1 microns and about 1000 microns, and more preferably between about 1 micron and about 100 microns for embodiments for the discrimination of cellular matter. Further, electrode element spacing may be between about 0.1 microns and about 1000 microns, and for cellular discrimination more preferably between about 1 micron and about 100 microns. Alteration of the ratio of electrode width to electrode spacing in the parallel electrode design changes the magnitude of the dielectrophoretic force and thereby changes the particle levitation characteristics of the design. The electrode elements may be connected to a common electrical conductor, which may be a single electrode bus carrying an electrical signal from the signal generator to the electrode elements. Alternately, electrical signals may be applied by more than one bus which provides the same or different electrical signals. In certain embodiments, alternate electrode elements may be connected to different electrode buses along the two opposite long edges of the electrode array. In this configuration, alternate electrode elements are capable of delivering signals of different characteristics. As used herein, "alternate electrode elements" may include every other element of an array, or another such repeating selection of elements. The electrode elements may be fabricated using standard microlithography techniques that are well known in the art. For example, the electrode array may be fabricated by ion beam lithography, ion beam etching, laser ablation, printing, or electrodeposition. The array may be comprised of for example, a 100 nm gold layer over a seed layer of 10 nm chromium or titanium. An apparatus according to the present invention may be used with various methods of the present invention. For example, an apparatus according to the present invention may be used in a method of discriminating particulate matter and solubilized matter utilizing dielectrophoresis and field flow fractionation. This method includes the following steps.

First, the chamber is preloaded through one inlet port with a carrier medium, such as a cell suspension medium, tissue culture medium, a sucrose solution, or the like. Cautions should be taken during the loading to ensure that no bubble (or only few small bubbles) is introduced into the chamber.

Secondly, the matter to be discriminated suspended or solubilized in a medium may then be introduced into one or more inlet ports of the chamber. During this introduction, certain electrical signals may be applied so that the matter to be discriminated is subjected to dielectrophoretic forces which may prevent the matter to be in contact with the walls containing the electrode elements. Alternatively, in some applications, no electrical signals are applied during the introduction of the matter.

Thirdly, after the introduction of the matter into the inlet region of the chamber, certain electrical signals may be applied for some time prior to the commencement of the fluid flow in the chamber. During this period, the matter may move to their appropriate positions (or equilibrium positions) under the influence of dielectrophoretic forces generated by the application of electrical signals and other forces such as gravity. At these positions, all the forces acting on the matter balance each other and the net force is zero or close to zero. The matters of different characteristics may attain different equilibrium positions within the chamber and are therefore discriminated according to their equilibrium positions. Alternatively, in some applications, no electrical signals are applied so that the matter may move to appropriate positions (equilibrium positions) under the influence of forces such as gravity.

Finally, a fluid flow is established in the chamber by, for example, pumping the carrier medium into the chamber using a syringe pump. This causes the carrier medium to travel through the chamber according to a velocity profile so that the velocity of the medium at different positions with respect to the chamber walls may be different. At least one alternating electrical signal may be applied to the one or more electrode elements, which creates an inhomogeneous alternating electric field within the chamber. This field causes dielectrophoretic forces to act on the matter within the chamber. Dielectrophoretic forces, together with other forces such gravity and hydrodynamic lifting forces, cause the matter to be displaced to equilibrium positions in the flow velocity profile within the carrier medium. At these equilibrium positions, the dielectrophoretic forces are balanced by other forces acting on the matter. The matters are discriminated according to their positions within the carrier medium. In addition, the matters at different positions are caused to travel at different velocities under the influence of the flow-velocity profile of the carrier medium. Thus, the matters are further discriminated according to their velocities. To further discriminate matter, the frequency, or magnitude or both of the electrical signal may be varied with time. Such change thereby causes a change in the inhomogeneous alternating electric field which, in turn, changes the dielectrophoretic forces acting on the matter and alters the displacement of the matter with respect to the electrode elements. These changes further influence the equilibrium positions of the matter within the flow velocity profile and the velocity of the matter. The matters are further discriminated according to their exit time from the chamber. The matter having larger velocities will exit the chamber ahead of others having small velocities. The matter after exiting the chamber may be collected and/or analyzed.

Another method according to the present invention for discriminating particulate matter and solubilized matter using dielectrophoresis and field flow fractionation includes the following steps. First, the chamber is preloaded through one inlet port with a carrier medium, such as a cell suspension medium, tissue culture medium, a sucrose solution, or the like. Secondly, the matter to be discriminated suspended or solubilized in a medium may then be flown into one or more inlet ports of the chamber. This introduction causes the carrier medium to travel through the chamber according to a velocity profile. The carrier medium at different positions of the chamber may travel at different velocities. At least one alternating electrical signal may be applied to the one or more electrode elements, which creates an inhomogeneous alternating electric field within the chamber. This field generates dielectrophoretic forces acting on the matter and causes the matter within the chamber to be displaced to a position in the flow velocity profile within the carrier medium. At such an equilibrium position, dielectrophoretic force acting on the matter is balanced by other forces such as gravity, or hydrodynamic lifting forces, or another dielectrophoretic force in the chamber. Thus, the matter is discriminated according to its position within the carrier medium. Furthermore, the matter may be discriminated, for example, according to its velocity. The matter at different positions of the flow velocity profile travels at different velocities under the influence of the fluid flow. To further discriminate matter, the electrical signal may be varied (frequency, or magnitude, or both). Such a change thereby causes a change in the inhomogeneous alternating electric field which, in turn, changes the dielectrophoretic force acting on the matter and changes the displacement of the matter with respect to the electrode elements. These changes further influence the equilibrium positions of the matter within the flow velocity profile and the velocity of the matter. The matters are further discriminated according to their exit time from the chamber. The matter having larger velocity will exit the chamber earlier than other having smaller velocities. The matter after exiting the chamber may be collected and/or analyzed.

Another method according to the present invention includes discriminating particulate matter and solubilized matter utilizing dielectrophoresis and field flow fractionation according to the following steps. First, the chamber is preloaded through one inlet port with a carrier medium, such as a cell suspension medium, tissue culture medium, a sucrose solution, or the like. Secondly, the matter to be discriminated is introduced into the chamber through one inlet port of a chamber. Next, a transport fluid, which may be, for example, a tissue culture medium or a gas, is flown into at least one duct. This causes a fluid flow in the chamber according to a velocity profile. The fluid at different positions of the chamber may travel at different speeds. At least one electrical signal is applied to at least one electrode element. These one or more electrical signals thereby create an inhomogeneous electric field within the chamber. The field causes a DEP force on the matter causing the matter to be displaced to a position within the transport fluid. At such an equilibrium position, DEP force is balanced by other forces (such as gravity, hydrodynamic lifting forces or another DEP force) acting on the matter. The matter is discriminated according to its position in the flow velocity profile within the transport fluid. As this transport fluid is subjected to a velocity profile, the matter moving at different velocities is thereby partitioned according to its position in the direction of the fluid flow. The matter is discriminated according to its velocity and its position within the fluid flow. To further discriminate matter, the electrical signal may be varied (frequency, or magnitude, or both). Such a change thereby causes a change in the inhomogeneous alternating electric field which, in turn, changes the dielectrophoretic force acting on the matter and changes the displacement of the matter with respect to the electrode elements. These changes further influence the equilibrium positions of the matter within the flow profile and the velocity of the matter. Furthermore, the separated particulate or solubilized matters may be collected at times dependent upon their velocities. It is further possible to collect the matter at one or more outlet ports for further analysis and characterization.

Another method according to the present invention for discriminating particulate matter and solubilized matter utilizing dielectrophoresis and field flow-fractionation includes the following steps. In this case, a continuous discrimination and separation of particulate matter and solubilized matter is achieved. The chamber according to the present invention has two outlet ports located on the two major facing walls. At least one of the two major walls supports an electrode array. First, the chamber is preloaded through one inlet port with a carrier medium, such as a cell suspension medium, tissue culture medium, a sucrose solution, or the like. Secondly, the matter to be discriminated suspended or solubilized in a medium is continuously introduced into the chamber. This causes a fluid flow in the chamber according to a velocity profile. At least one electrical signal is applied to at least one electrode element. These one or more electrical signals thereby create an inhomogeneous electric field within the chamber. The field causes a DEP force on the matter causing the matter to move towards equilibrium position within the transport fluid. Thus, the matter is not only carried with the fluid flow but also driven by combined influences of DEP and other forces such as gravity, hydrodynamic lifting forces or another DEP forces. When the matter reaches the outlet end, it will exit the chamber at one of the two outlet ports, depending on its position along the direction normal to the two major walls of the chamber. The matter is discriminated according to the outlet port it exits the chamber. For example, if the matter consists of two subpopulations having different dielectric properties, the two subpopulation of the matter may attain different positions in the fluid flow when they reach the chamber outlet end. The separation of the two populations is achieved since the two populations exit the chamber at the two different outlet ports. Clearly the discrimination of the matter using this approach can be operated continuously. The separated matter from the two outlet ports may be further collected and analyzed.

There are further steps possible to more precisely discriminate matter. These steps include the following. First, the alternating electrical signal or signals may be selected at a frequency and voltage combination which causes the matter to be either attracted towards or repelled from the electrode elements. By doing so, the matter is more clearly displaced within the transport fluid. By application of such a voltage and frequency combination, it is possible to hold the matter in close proximity to the electrode elements.

It is possible to select a frequency to attract desired or nondesired matter. As used herein, desired matter may be any matter which is desired to be discriminated and collected for further use. For example, the separation of normal blood cells from a sample containing "contaminated" cancer cells may be desired for use in returning these normal cells into a patient's bloodstream. So normal cells may be called "desired matter" in this case. Nondesired matter may be matter which is desired to be discriminated for other purposes. For example, cancer cells from a patient's blood or bone marrow may be discriminated so that a sample of blood not containing the cancer cells may be returned to the patient. In this case, the cancer cells may be called "nondesired matter".

A method for discriminating such a combination of matter may include the following. A frequency is selected so that the nondesired matter is held in close proximity to the electrode elements while simultaneously the desired matter is carried with the fluid flow and is separated from the nondesired matter. This frequency may be known as a holding frequency. The fluid flow then carries the desired matter to the outlet port or ports of the chamber, where it may be collected. During this process, the desired matter may also be subjected to further discrimination and separation so that the subpopulations of the desired matter are separated under the cDEP/FFF operation. After collection, the desired matter may, for example, be returned to a patient's bloodstream or bones, or it may be used for diagnosis or other molecular or biochemical analysis. Then, to clear the chamber, the frequency may be changed, or the voltage itself may be turned off. This will cause the nondesired matter to be released from close proximity to the electrode element and will be partitioned by the fluid flow. This nondesired matter may then flow through the chamber in the fluid, and may be collected, if required. After collection, the nondesired matter may be used, for example, for diagnosis or other purposes.

In an alternate embodiment, it may be possible to hold desired matter in close proximity to the electrode elements, and first partition the nondesired matter by the fluid flow, following the same steps outlined above.

The apparatus and methods of the present invention may be used for a number of different useful manners. For example, the methods according to the present invention may be used to determine characteristics of an unknown particulate matter and unknown solubilized matter in a sample of matter. These characteristics can then be compared to known matter. Additionally, the methods of the present invention may be used to diagnose a condition by determining a presence of unidentified particulate matter and unidentified solubilized matter in a patient sample. This unidentified matter may be, for example, the presence of a cancer, a virus, parasite, or the like. After determining the presence of a condition, the methods of the present invention may be used to treat the condition by using an apparatus according to the present invention to discriminate the cancer, virus, parasite or the like from normal blood or bone marrow cells.

"Manipulation or discrimination" as used in relation to the present invention may include, for example, characterization, separation, fractionation, concentration and/or isolation.

Typical biological applications for the device useful for specific products and services include the manipulation or discrimination of tumor cells, such as epithelial tumor cells or leukemia cells, from blood and hemopoietic stem cells, purging of tumor cells from bone marrow and hemopoietic stem cells and mixtures with other normal cells, purging of residual T-lymphocytes from stem cells, and enrichment of specific target cell types including tumor cells, stem cells, etc. Also included is the manipulation or discrimination of leukocyte cell subpopulations, removal and concentration of parasitized erythrocytes from normal erythrocytes in malaria and of other parasitized cells from their normal counterparts, manipulation of cells at different phases of the cell cycle, manipulation of viable and non-viable cells, manipulation of free cell nuclei, and manipulation of nucleated fetal erythrocytes and trophoblast cells from maternal blood for further analysis including genetic testing. Moreover, the invention contemplates the manipulation of bacteria, viruses, plasmids and other primitive organisms from water, blood, urine, cell mixtures and other suspensions, manipulation and identification of tumor cells in biopsies, plaques and scrape tests including Pap smears, and the manipulation and identification of metastatic tumor cells from cell mixtures.

With different and smaller electrode geometries, it is contemplated that the technology can be used for molecular applications including manipulation of DNA or RNA molecules and/or DNA or RNA fragments according to their molecular weight, folding characteristics and dielectric properties, manipulation of chromosomes, manipulation of specific protein/DNA and protein/RNA aggregates, manipulation of individual proteins from a mixture, and manipulation of specific subcellular molecular complexes and structures.

The chamber used for cDEP/FFF application may vary significantly in size to fit the need of different sample sizes. For example, the large size chamber may be implemented for separating many millions of the cells at each operation. On the other extreme, the chamber may be miniaturized so to form a microfluidic cell separation step in an integrated bioanalytical system. Such miniaturized chamber may be integrated with other microfluidic devices or components. In order to optimize particle discrimination in different applications it is understood that the present invention may encompass use of specifically-targeted electrodes and chamber designs. These designs should provide a sensitive dependency of the height of particle levitation on the particle dielectric properties. For example, alteration of the ratio of electrode width to electrode spacing in the parallel electrode design changes the vertical component of the dielectrophoretic force and thereby changes the particle levitation characteristics of the design. Other strategies for providing improved particle discrimination include, for example, using more than two sets of electrode elements with different frequencies and/or voltages applied to them and the exploitation of synergism between electrical signals applied to electrode arrays on both the chamber bottom and top walls. In addition, dielectric (i.e. non-conducting) elements can be placed within the chamber to modify both the electrical field distribution and the hydrodynamic flow profile. The electrode element size and shape may be designed to optimize discrimination. Furthermore, several electrode geometries (energized with the same or different electrical signals) can be connected serially so as to provide for stepwise discrimination between different particulate matter and solubilized matter. Different chamber configurations can also be used in series. Finally, cells that have been separated by an upstream cDEP/FFF configuration can be collected and held downstream by cDEP trapping for characterization.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

$A = -2.2072 \times 10^{13}/m^3$; $U=1.41$ V; $d=200$ $\mu$m; $\epsilon_m = 78\epsilon_0$ ($8.854 \times 10^{-12}$ F/m); $\rho_c = 1.072$ (MDA-435), 1.095 (erythrocytes) kg/dm$^3$; $\rho_m = 1.033$ kg/dm$^3$. Continuous curves ( —— MDA-435; ----- erythrocytes)

are polarization factors calculated from dielectric modeling (equations 21–24) using parameters derived from cell electrorotation measurements. For MDA-435 cells, r=7.5 $\mu$m, $C_{mem}(\epsilon_{mem}/d) = 24$ mF/m$^2$; $G_{mem}(\sigma_{mem}/d) = 200$ S/m$^2$; $\epsilon_{int} = 60$; and $\sigma_{int} = 0.5$ S/m. For erythrocytes, a=b=3.5 $\mu$m, ellipsoid factor e=4; $C_{mem}(\epsilon_{mem}/d) = 8.7$ mF/m$^2$; $G_{mem}(\sigma_{mem}/d) = 200$ S/m$^2$; $\epsilon_{int} = 60$; and $\sigma_{int} = 0.5$ S/m.

Figure 25A:
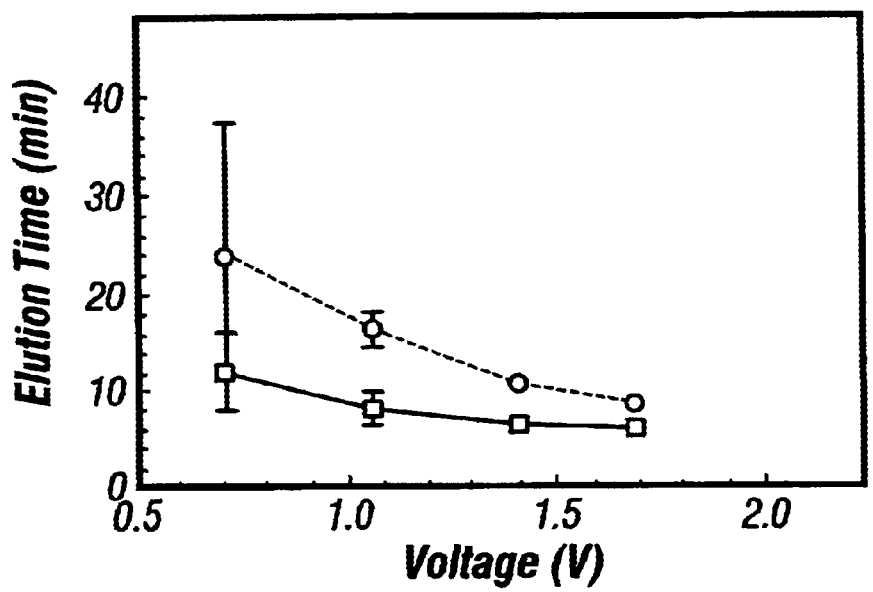

FIG. 25A Voltage dependency of the elution-time for MDA-435 (square) and erythrocytes (circle), with the error bars representing the elution-peak width. Large applied voltages increased DEP levitation forces so that cells were positioned higher above the chamber bottom wall, leading to larger FFF velocity and shorter elution time. Cells were suspended in an isotonic sucrose/dextrose medium of 56 mS/m. The applied DEP field frequency was 20 kHz and flow rate =1 mL/min.

Figure 25B:
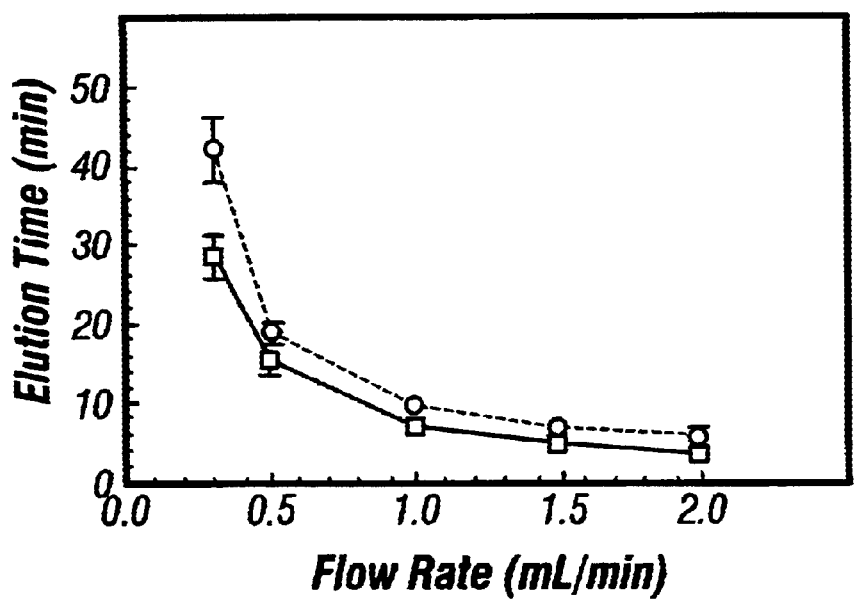

FIG. 25B Flow-rate dependency of the elution-time for the MDA-435 (square) and erythrocytes (circle), with the error bars representing the elution-peak width. Elution-time was found to be inversely proportional to the flow rate, indicating that cell positions in the flow profile were not influenced by the change in the flow rate. Experimental conditions are the same as in FIG. 25(A), except the applied voltage U=1.41 V.

Figure 26:
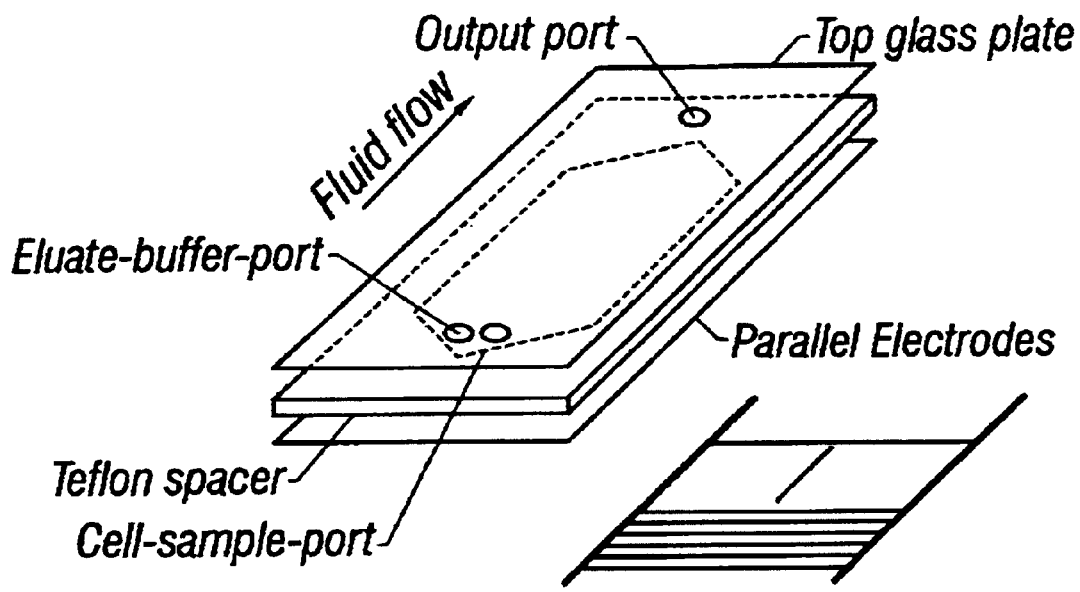

FIG. 26 Schematic representation of a DEP-FFF chamber of dimension 200 $\mu$m (H)×25 mm (L)×17 mm (W). The cell sample is preloaded into the inlet regions of the chamber from the cell-sample-port. After cells settle onto the bottom wall, eluate buffer is pumped through the chamber via the eluate-buffer-port so as to establish a hydrodynamic laminar flow profile in the chamber. Appropriate voltage signals are then applied to the electrode elements to cause cells to equilibrate at different heights and travel at correspondingly different velocities in the flow profile. In this study, parallel electrodes with equal electrode width and spacing of 20 (or 50) $\mu$m were used with alternate elements connected to electrode buses running along the two long edges of the chamber.

Figure 27:
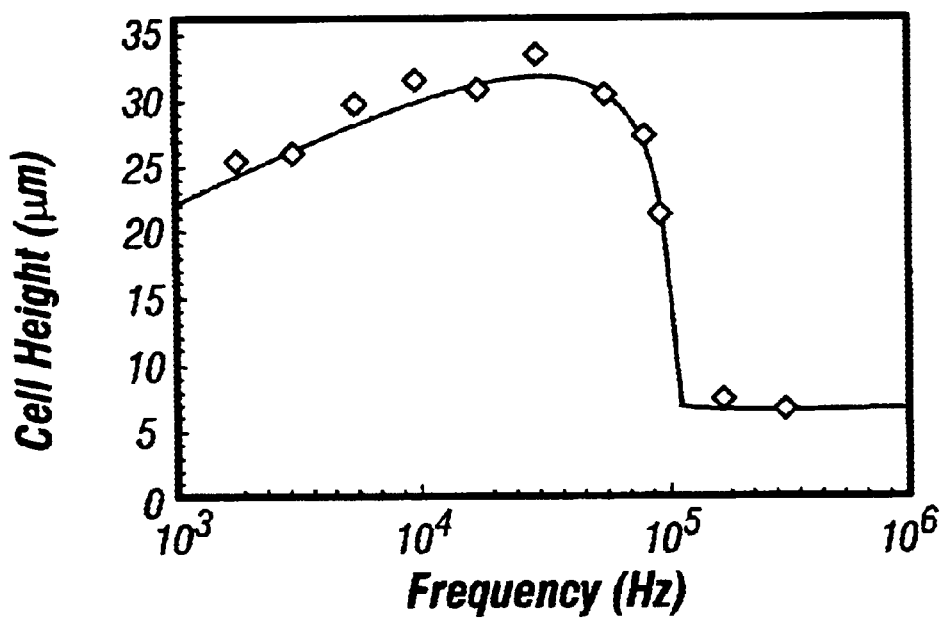

FIG. 27 The frequency dependency of levitation height (diamond symbol) of a typical HL-60 cell (radius=6.6 $\mu$m) suspended in a sucrose/dextrose medium of conductivity 56 mS/m under an applied voltage of 1.06 V (RMS) on a parallel electrode array (20 $\mu$m width and spacing). No fluid flow is present. The continuous curve represents the best fit of the experimental data using DEP levitation theory (Equations 18–19, Huang et al, 1997). The factor dielectric polarization Re($f_{CM}$) is based on a single-shell dielectric model (Irimajiri et al., 1979; Huang et al., 1992), for which, the cell interior relative permittivity and conductivity are assumed to be 75 an 0.75 S/m, respectively. The best fit yielded values for the membrane capacitance and conductance of 16.3 mF/m$^2$ and <50 S/m$^2$, respectively.

Figure 28:
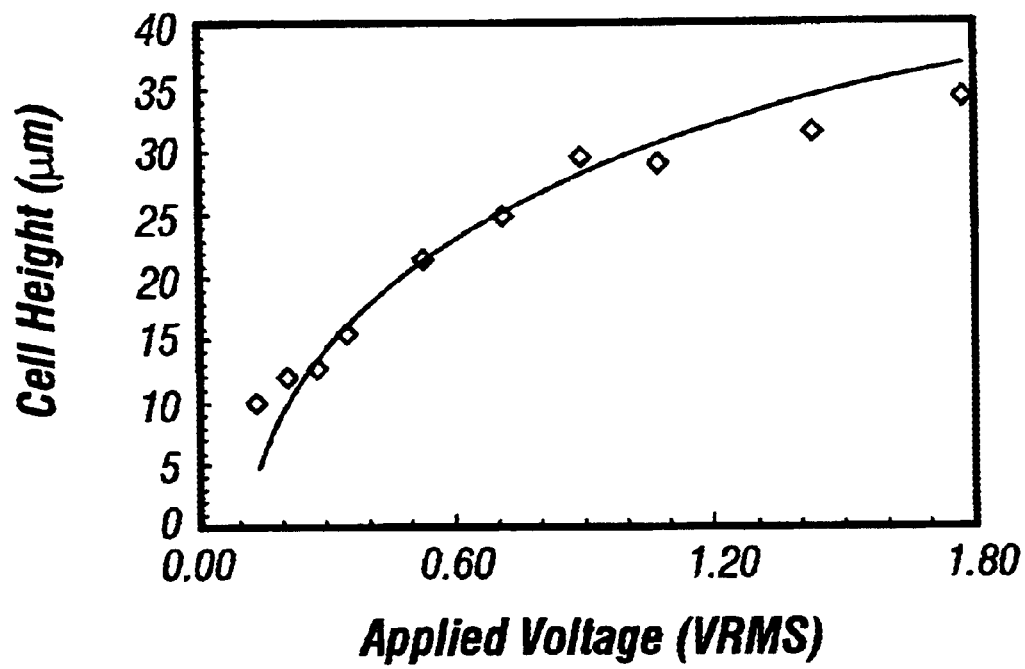

FIG. 28 The voltage dependency of the levitation height (diamond symbol) of an HL-60 cell (radius=6.3 $\mu$m) suspended in a medium of conductivity 56 mS/m for an applied filed of frequency 17.8 kHz field. No fluid flow is present. The continuous curve represents the best fit to the experimental data using dielectrophoretic levitation theory (Huang et al, 1997). The dielectric polarization factor Re($f_{CM}$) is derived as −0.43. In the simulation, the value for the electrode polarization factor p(f) at 17.8 kHz was 0.67 (Huang et al., 1997).

Figure 29:
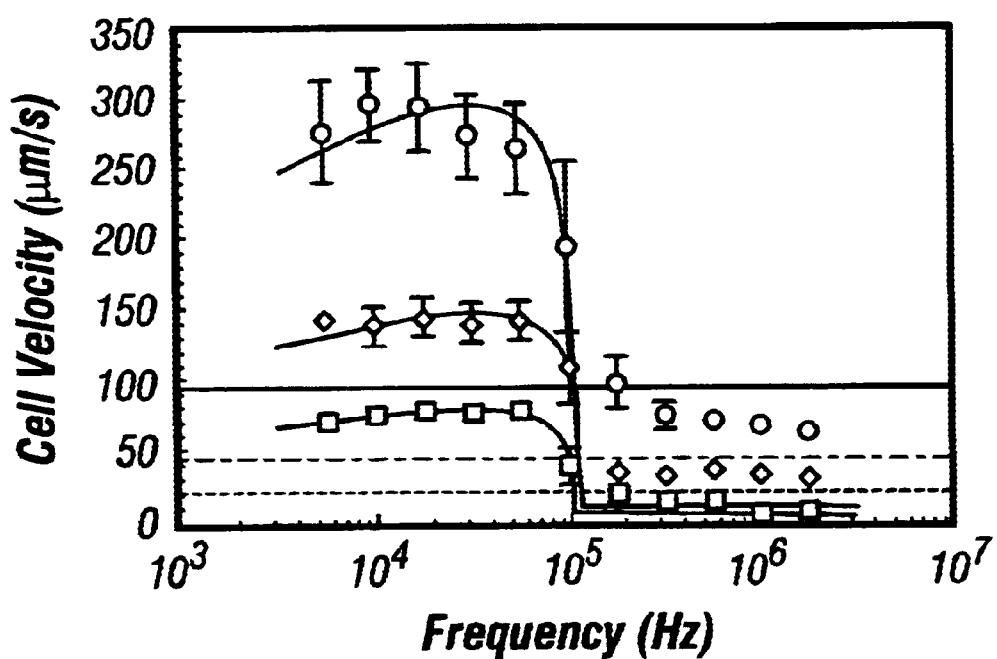

FIG. 29 The frequency dependency of the mean velocity for HL-60 cells suspended in a sucrose/dextrose medium of conductivity 44 mS/m in a thin chamber containing parallel microelectrode arrays (20 $\mu$m width and spacing) at flow rates of 20 ((square, lower curve <v>=98); 40 (diamond, middle curve, <v>=196); and 80 $\mu$l/min (circle, upper curve, <v>=392 $\mu$m/s). The parameter <v> is the average fluid flow velocity in the chamber. The applied voltage was 1.06 V (RMS). Chamber dimensions were 200 $\mu$m (H)×25 mm (L)×17 mm (W). Each symbol represents the mean velocity of about 20 cells. The continuous lines show the best fit of dielectrophoretic field-flow-fractionation theory (Huang et al, 1997), the broken lines (20: ----- ; 40: —--- ; 80 μl/min: ——- )

the averaged cell velocity when the electrical field was turned off. In the single shell model (Huang et al, 1992; 1997), the cell radius, interior relative permittivity and conductivity are taken to be 5.8 $\mu$m (measured by microscopy), 75 and 0.75 S/m, respectively. The best fits for the three flow rates gave values for cell membrane specific capacitance of 15.6 (±0.95) mF/m$^2$ and conductance of 220 (±76) S/m$^2$.

Figure 30:
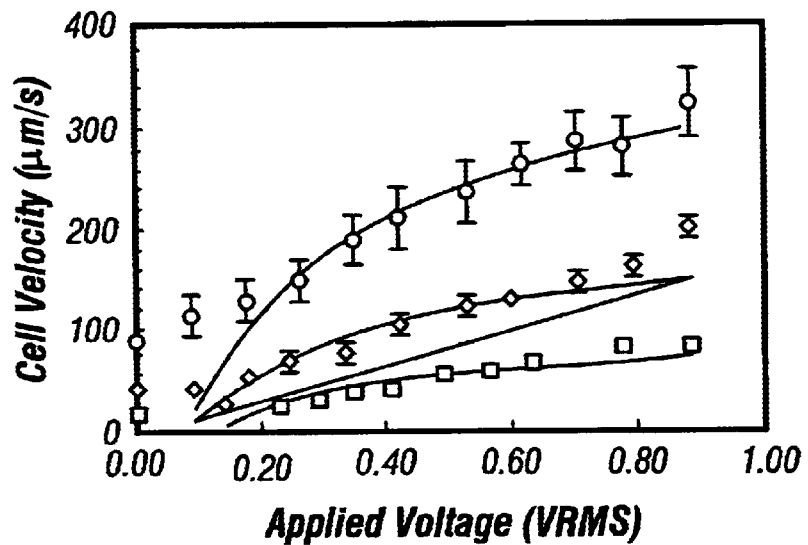

FIG. 30 The voltage dependency of the mean velocity of HL-60 cells suspended in a sucrose/dextrose medium of conductivity 44 mS/m in a thin chamber containing parallel microelectrode arrays (20 $\mu$m width and spacing) at flow rates of 20 (square, lower curve, <v>=98), 40 (diamond, middle curve, <v>=196), and 80 $\mu$l/min (circle, upper curve, <v>=392 $\mu$m/s). The parameter <v> is the average fluid flow velocity in the chamber. The applied field frequency was 31.6 kHz. Chamber dimension were H (200 $\mu$m)×L (25 mm)×W (17 mm). The continuous curve represents a best fit of dielectrophoretic field-flow-fractionation (DEP-FFF) theory to the experimental data for which the factor Re($f_{CM}$) was derived as −0.46 (±0.065).

Figure 31:
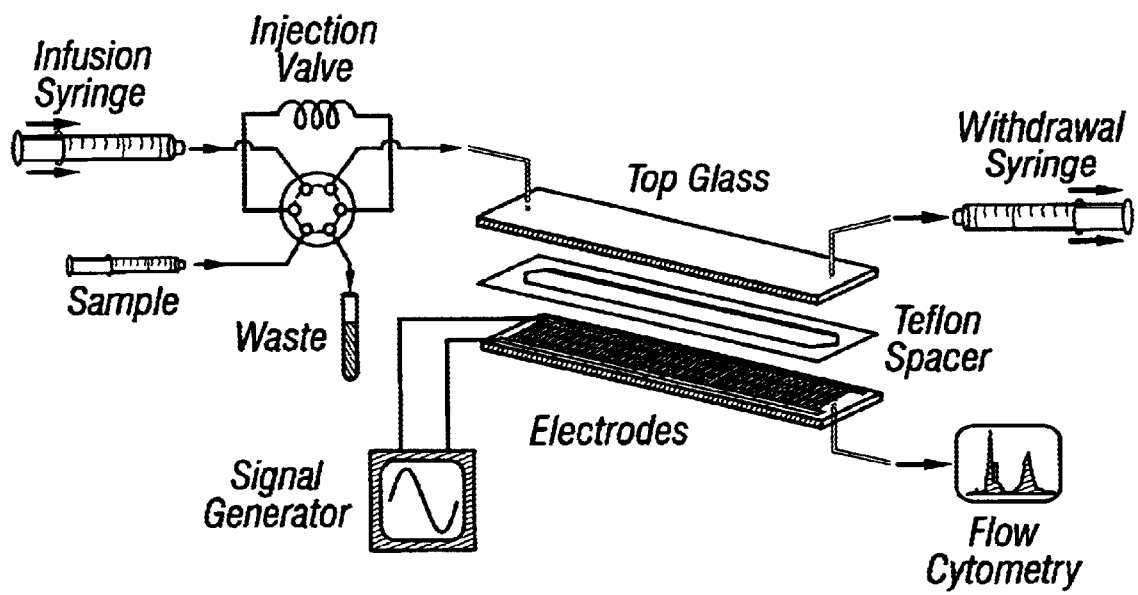

FIG. 31 DEP-FFF experimental setup. Microfabricated electrodes on the bottom wall of the separation chamber were energized with electrical signals and provided DEP levitation forces. After being introduced to the chamber through the injection valve, the cells of different types in a mixture were levitated to different equilibrium heights under the balance of DEP and sedimentation forces. A fluid flow profile was produced in the chamber from the injection syringe pump. The cells were transported through the chamber at different velocities corresponding to their heights, exited the chamber from the bottom outlet port and were detected by the flow cytometer.

Figure 32:
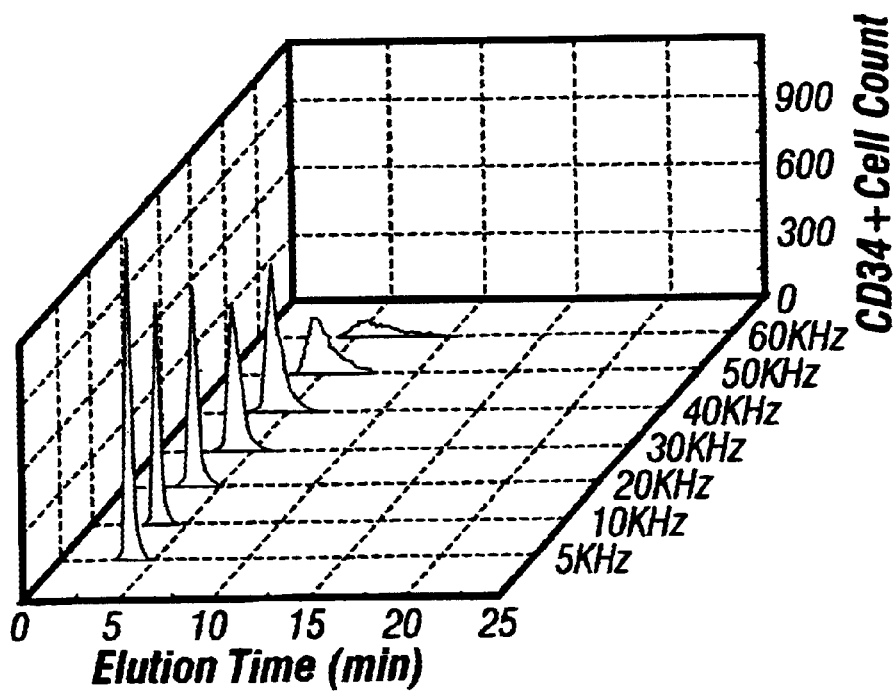

FIG. 32 Frequency dependency of DEP-FFF elution fractograms for CD34$^+$ stem cells obtained by the flow cytometer. Cells were suspended at $1.5 \times 10^6$/mL in the sucrose buffer having an electrical conductivity of 10 mS/m. The applied voltage was 4 V p-p. The injection and withdrawal syringe pumps were operated at 2 and 1.8 mL/min, respectively.

Figure 33:
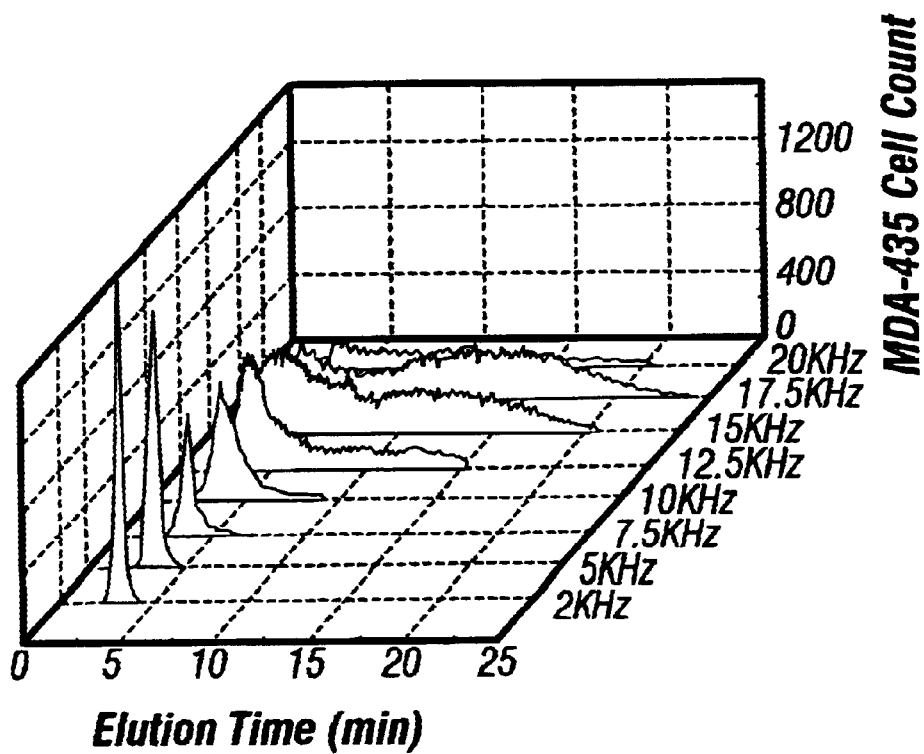

FIG. 33 Frequency dependency of DEP-FFF elution fractograms for MDA-435 cells obtained by the flow cytometer. Cells were suspended at $1.5 \times 10^6$/mL in the sucrose buffer having an electrical conductivity of 10 mS/m. The applied voltage was 4 V p-p. The injection and withdrawal syringe pumps were operated at 2 and 1.8 mL/min, respectively.

Figure 34:
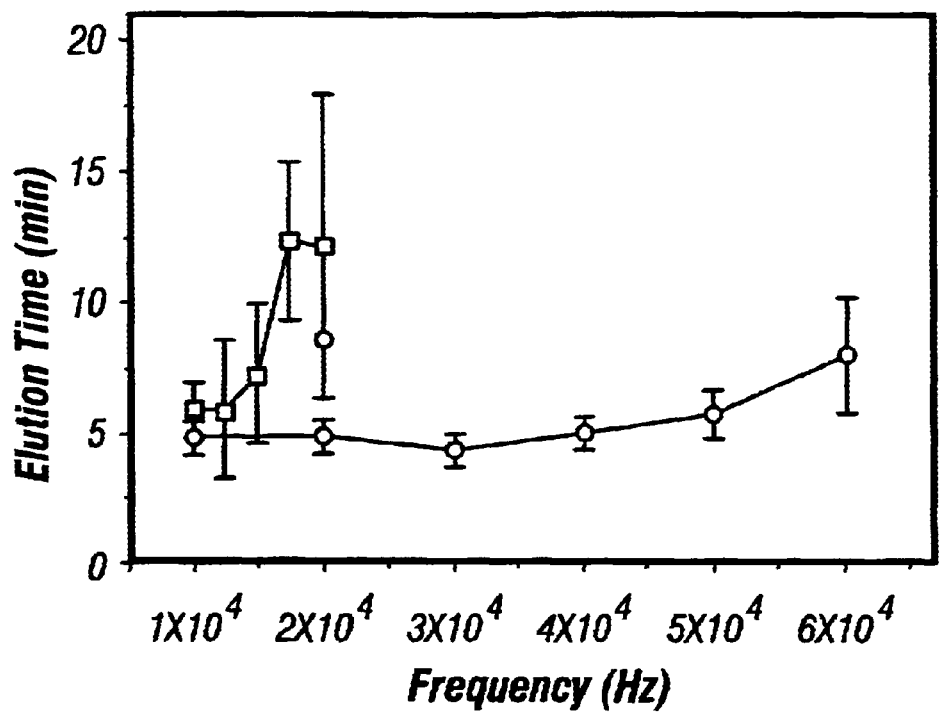

FIG. 34 Frequency dependency of elution-time for MDA-435 cells (square) and CD34$^+$ stem cells (circle). Error bars stand for the elution peak width for each DEP-FFF fractogram.

Figure 35:
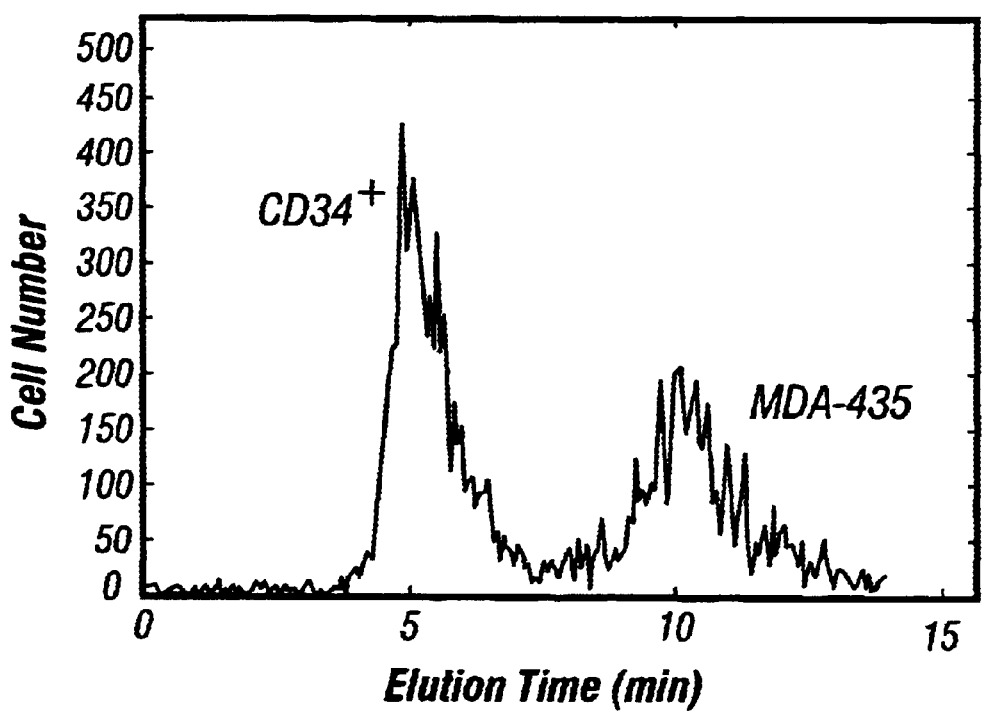

FIG. 35 DEP-FFF fractograms for separating MDA-435 cells from CD34+ cells using the trap-and-release protocol. DEP field was operated at 40 kHz for 7 min and switched to 5 kHz for 7 min. CD34− cells were pre-labeled with PE-conjugated CD34 antibodies and were identified by flow cytometer to elute the chamber earlier than MDA-435 cells. DEP signal voltage and fluid-flow conditions were the same as those used for FIG. 33.

Figure 36:
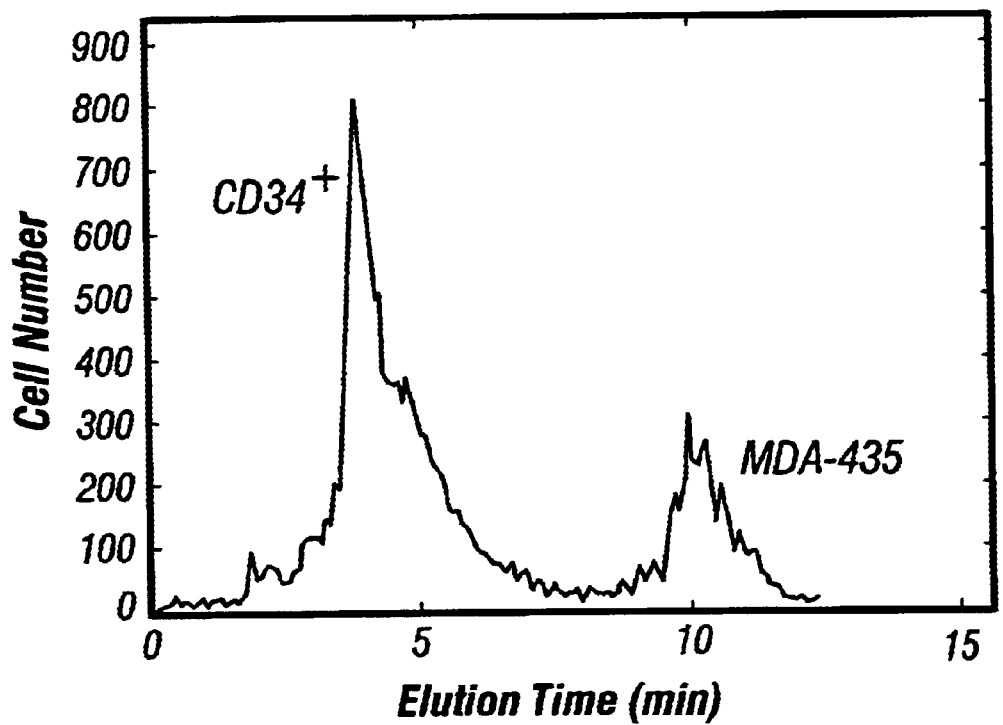

FIG. 36 DEP-FFF fractogram for separating MDA-435 cells from CD34− cells by the swept-frequency protocol. The DEP field was swept between 15 and 35 kHz for 7 min and then switched to 5 kHz for 7 min. DEP signal voltage and fluid-flow conditions were the same as those used in FIG. 33.

Figure 37:
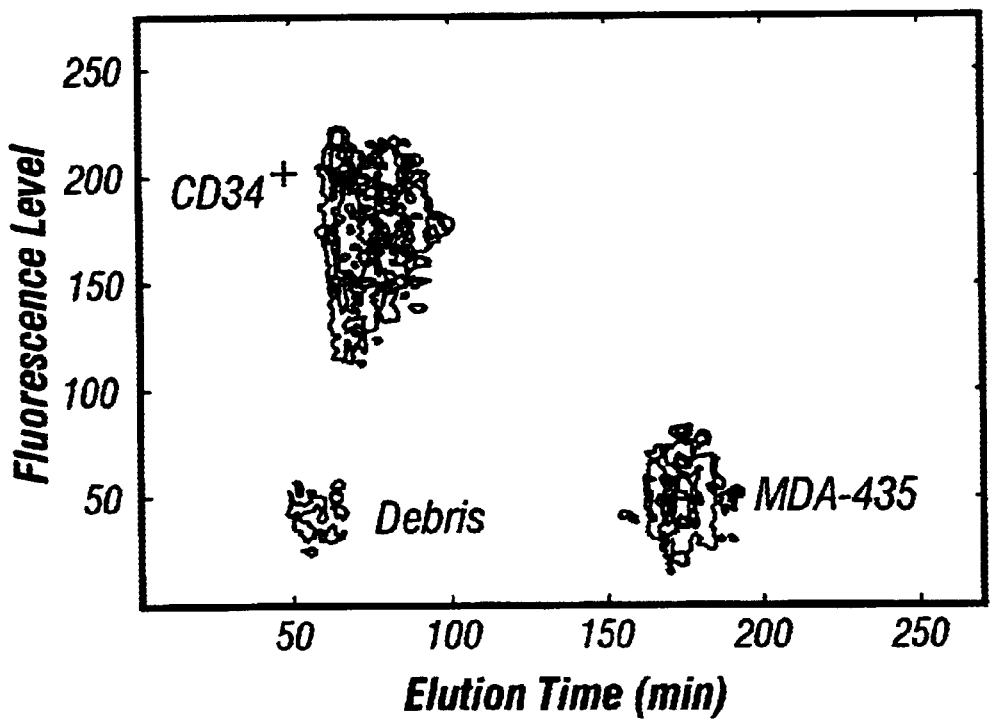

FIG. 37 Contour plot for fluorescence level vs elution time for cells that exited the DEP-FFF chamber for the separation shown in FIG. 36.

Figure 38A:
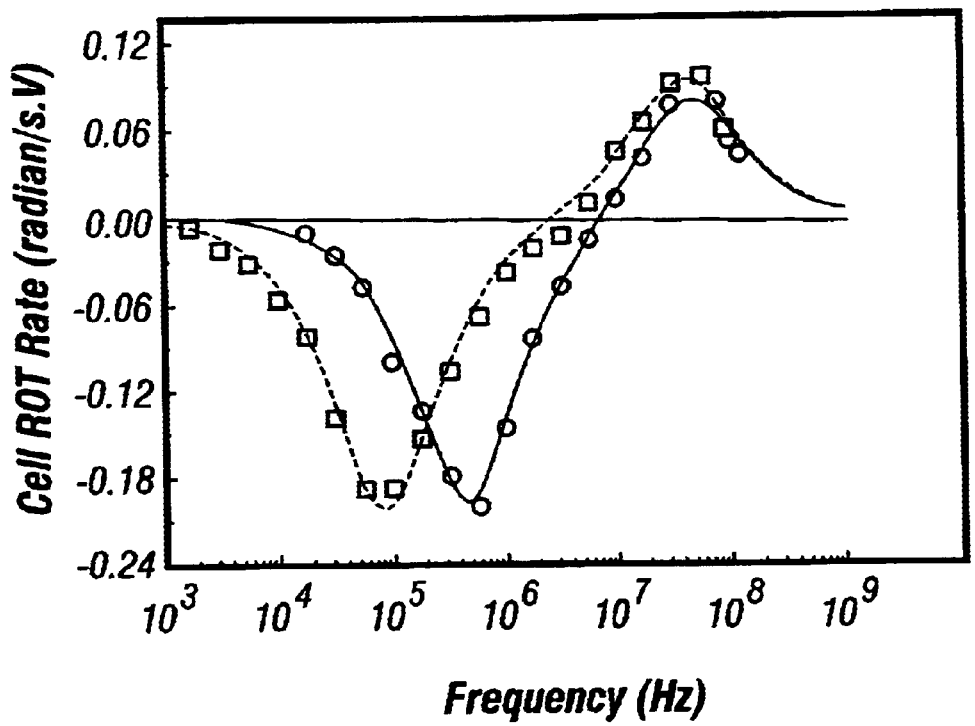
Figure 38B:
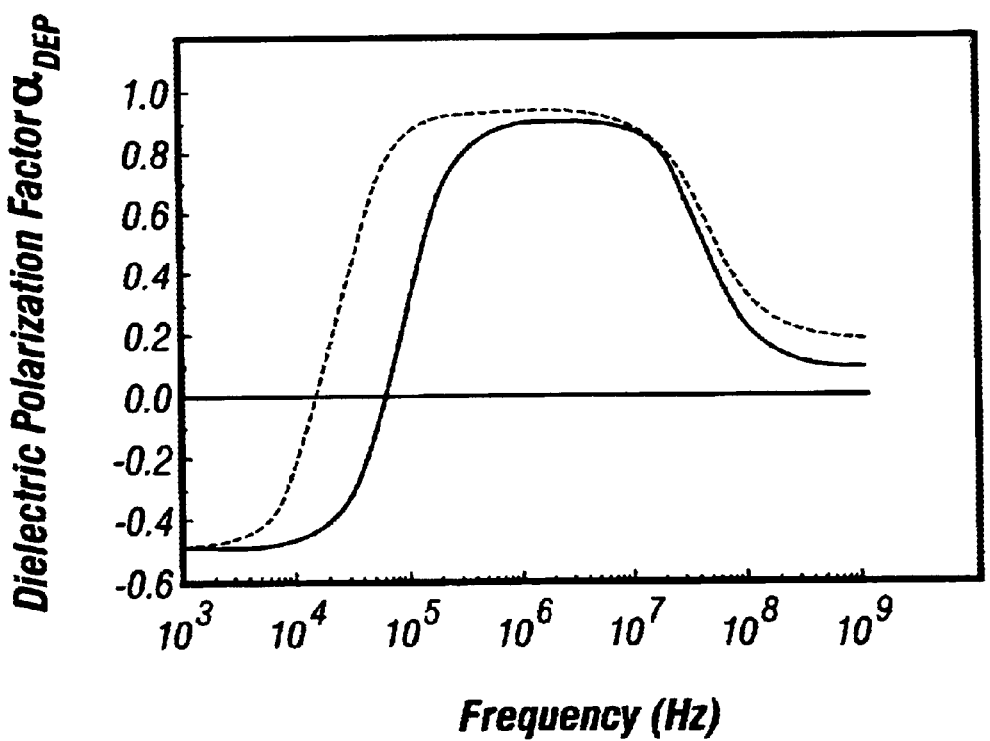

FIGS. 38A–38B (A) Typical electrorotation spectra for CD34+ (circle) and MDA-435 (square) cells in the sucrose buffer having a conductivity of 56 mS/m. Continuous curves show best fit of the single-shell dielectric model (Irimajiri et al., 1979; Huang et al, 1992).

(B) The frequency spectra of $\alpha_{DEP}$ (normalized DEP response) for

CD34+ (———) and MDA-435 (-----)

cells under separation conditions (conductivity 10 mS/m) calculated using the dielectric parameters (Table 1) derived from ROT measurements.

Figure 39:
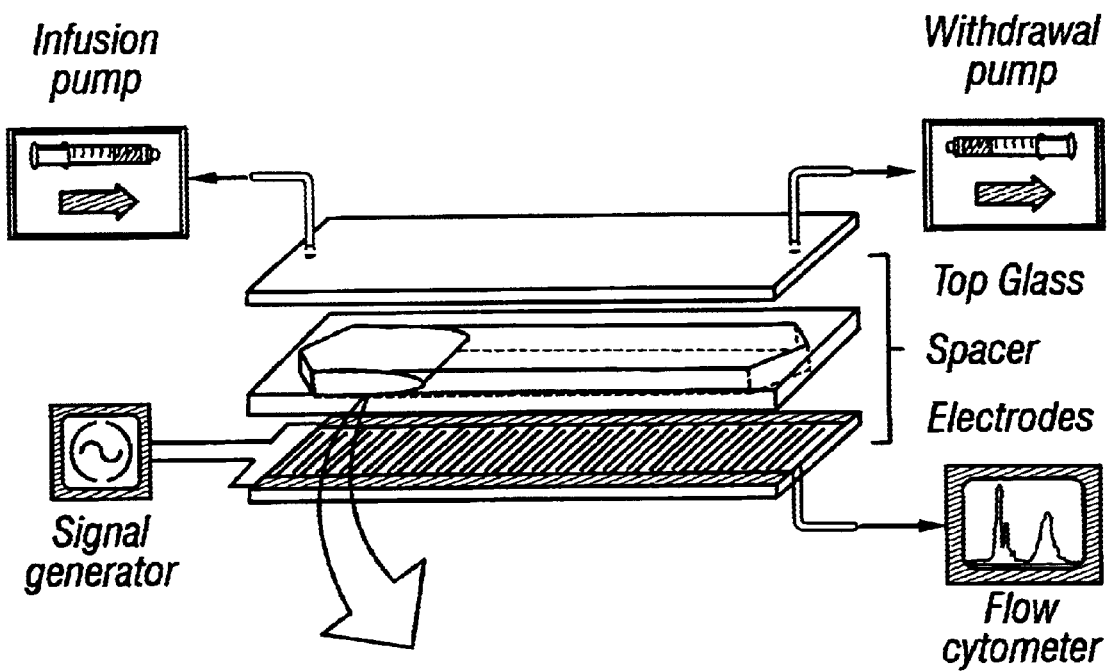
Figure 39:
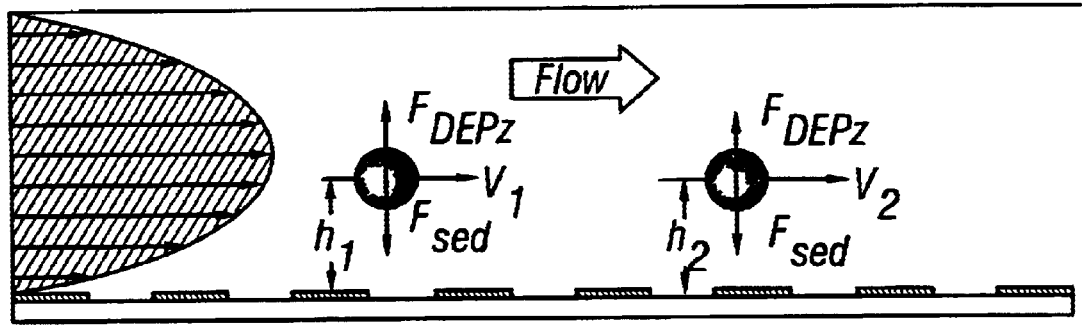

FIG. 39. Schematic showing DEP-FFF set-up and operating principles according to the present disclosure. A thin, rectangular chamber may be constructed with microfabricated, interdigitated electrodes on its bottom wall. Different cell types may be levitated to different equilibrium heights under the influence of the opposing DEP ($F_{DEPz}$) and sedimentation ($F_{sed}$) forces. With a flow velocity profile established in the chamber from an injector, cells at different heights ($h_2>h_1$) may be carried through the chamber at different velocities ($V_2>V_1$) and thereby separated. Cells may exit the chamber from the bottom outlet port and may be detected and counted by a detector such as an on-line flow cytometer.

FIGS. 40A–40B.

(A) Frequency dependency of DEP-FFF elution fractograms for T-lymphocytes obtained by the on-line flow cytometer.

(B) Frequency dependency of DEP-FFF elution fractograms for human breast cancer MDA-435 cells obtained by the on-line flow cytometer. Compared with T-lymphocytes, MDA-435 cells exhibited rapidly-broadening elution fractograms as frequencies increased above 10 kHz. Note the frequency scale difference. Cells were suspended at 1.2× 10⁶/ml in an isotonic sucrose/dextrose buffer having an electrical conductivity of 10 mS/m. The applied voltage was 4 V p-p. The injection and withdrawal syringe pumps were operated at 2 and 1.6 mL/min, respectively.

FIGS. 41A–41D.

(A) DEP-FFF fractograms showing the separation of human breast cancer MDA-435 cells from T-lymphocytes by a DEP field at 40 kHz followed by a 5 kHz field (see Method and Materials for details).

(B) DEP-FFF fractograms showing the separation of human breast cancer MDA-435 cells from T-lymphocytes by a DEP field swept between 15 and 35 kHz followed by a 5 kHz field.

Figure 41A:
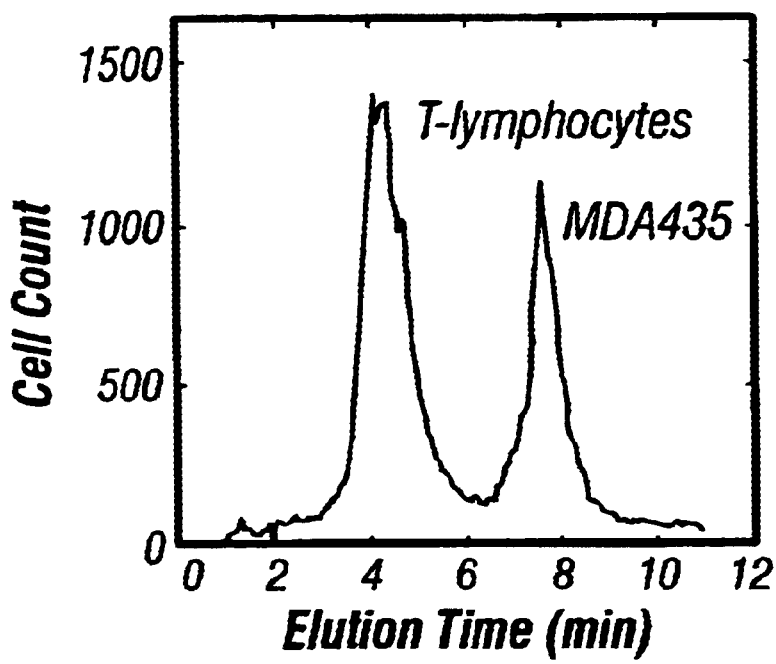

(C) contour plots show fluorescence level vs elution time for cells exiting the DEP-FFF chamber for the separation in FIG. 41A.

Figure 40A:
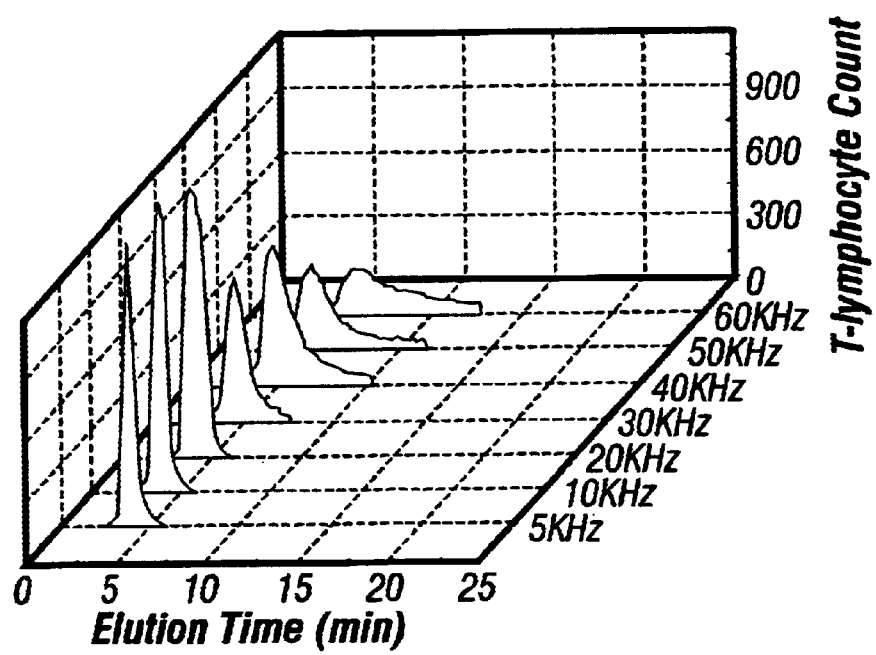
Figure 40B:
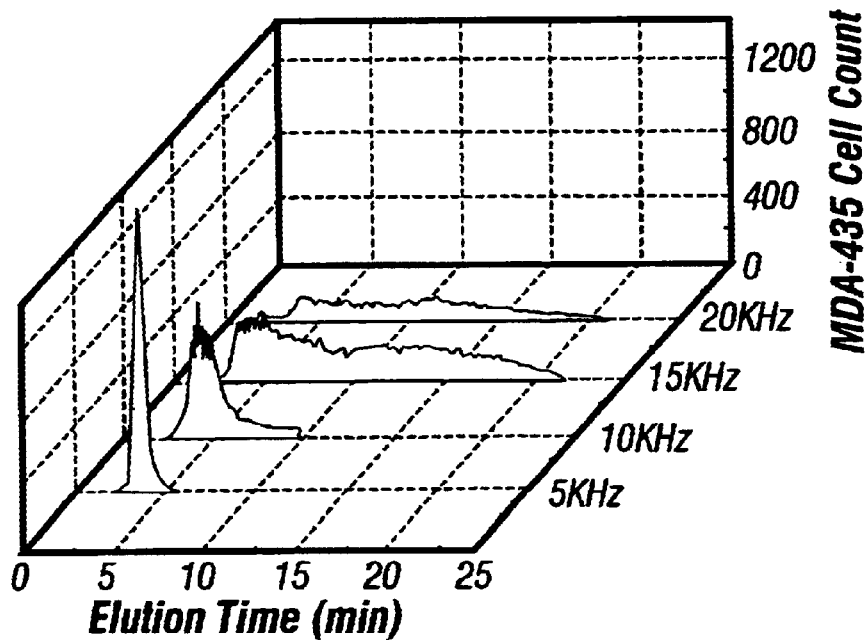
Figure 41B:
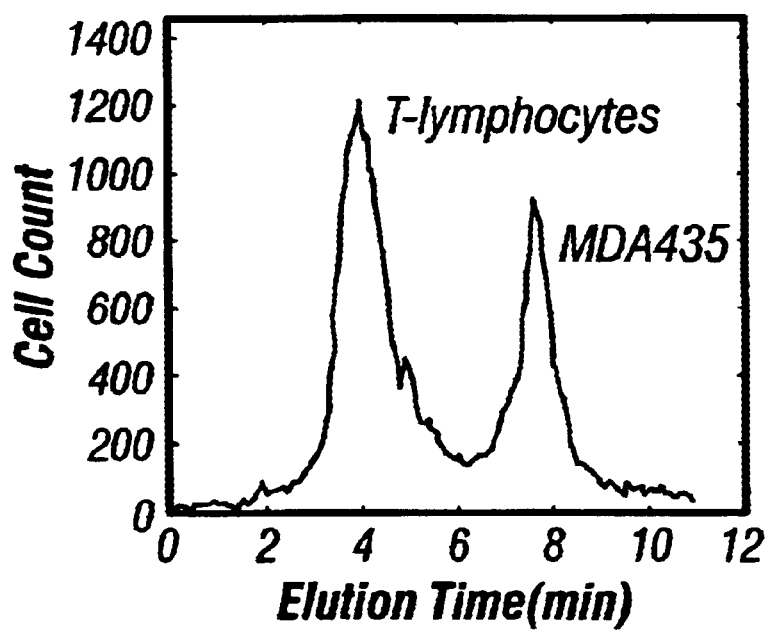
Figure 41C:
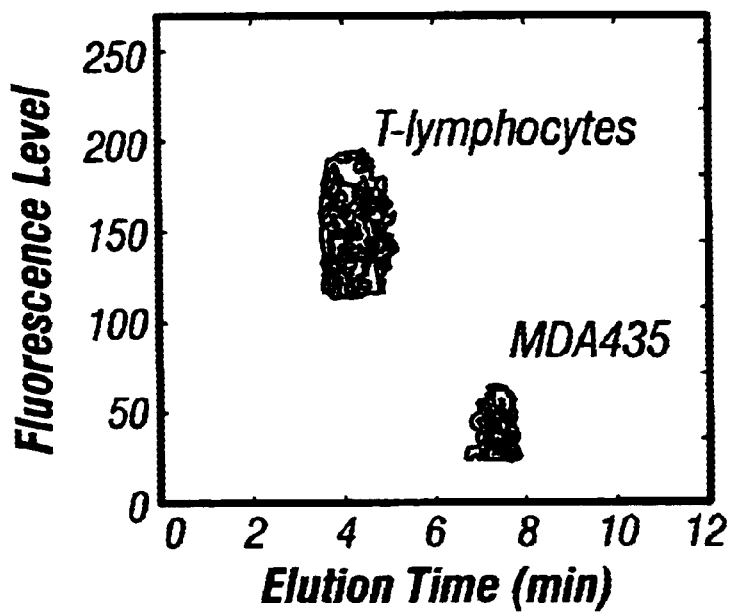
Figure 41D:
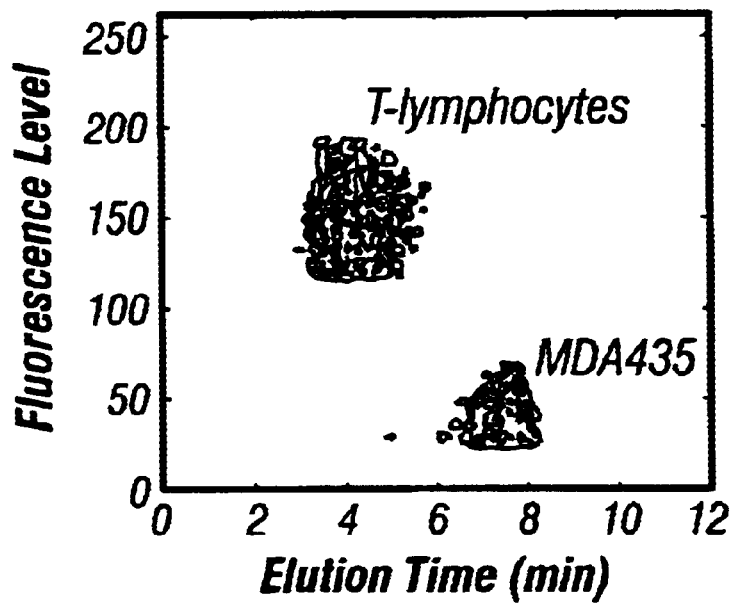

(D) contour plots show fluorescence level vs elution time for cells exiting the DEP-FFF chamber for the separation in FIG. 41B. To allow identification, the T-lymphocytes were fluorescently labeled with PE-conjugated CD3 antibodies. Cell suspension, DEP signal voltage and fluid-flow conditions were the same as for FIGS. 40A–40B.

Figure 42:
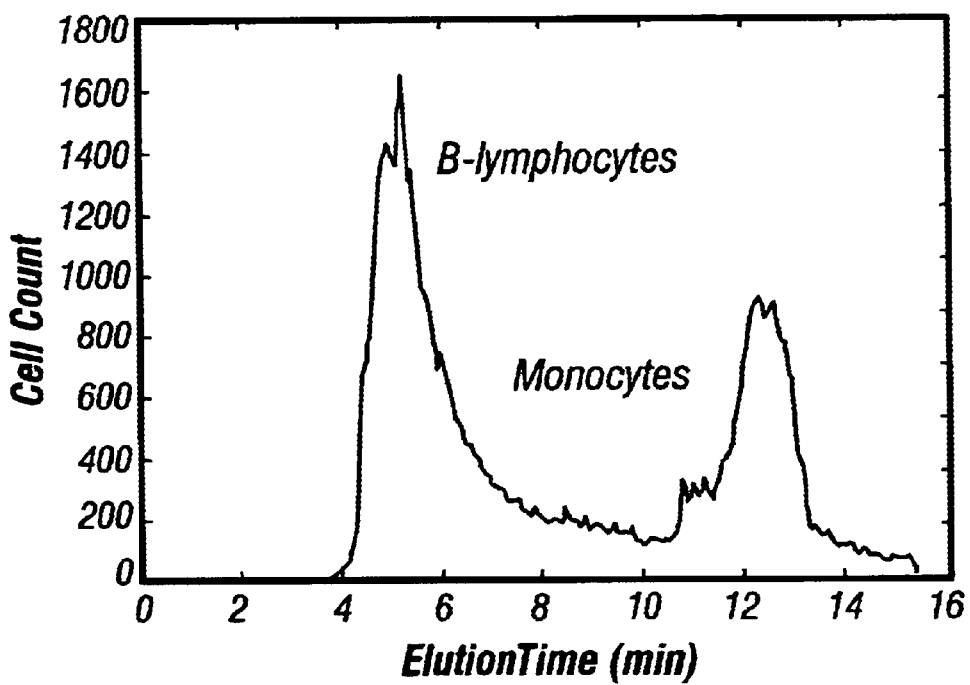

FIG. 42. DEP-FFF fractogram showing the separation of monocytes from B-lymphocytes. The injection and withdrawal syringe pumps were operated at 2 and 1.9 mL/min, respectively. Identification of monocytes and B-lymphocytes by flow cytometry was made possible by pre-labeling them with PE-CD14 and FITC-CD19 antibodies respectively. The cell suspension and DEP field conditions were the same as FIGS. 40A–40B, except that the DEP field was swept between 20 and 40 kHz.

Figure 43:
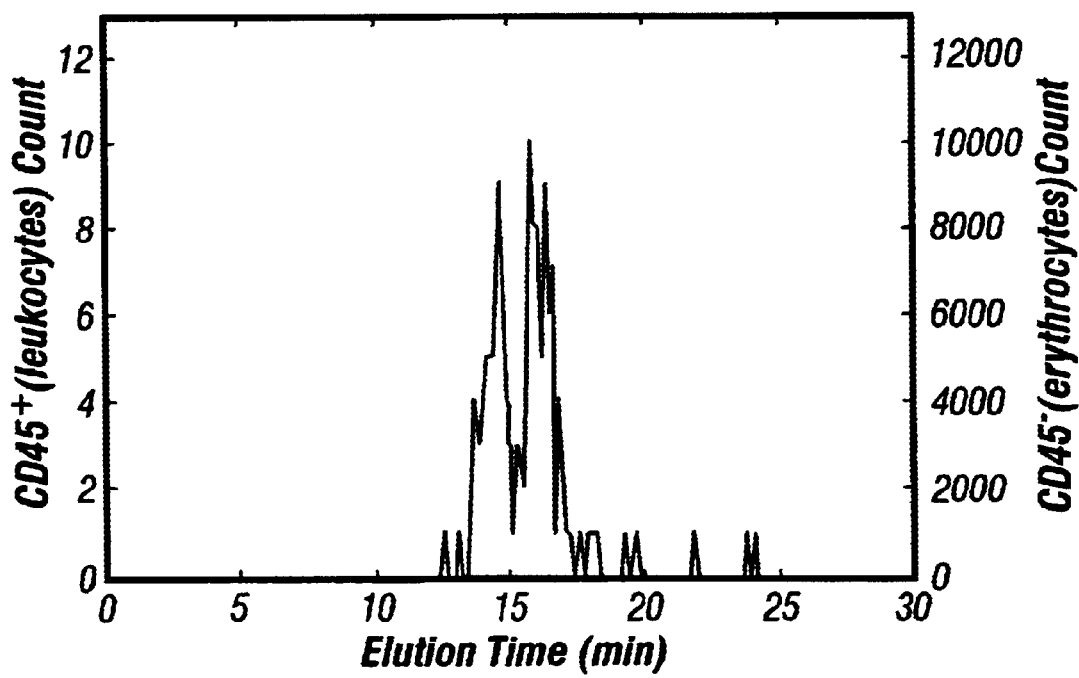

FIG. 43. Flow cytometric cell count for leukocytes (CD45+, solid line) and erythrocytes (CD45−, dashed line) as a function of elution time during DEP-FFF enrichment of leukocytes from blood. More than 95% of leukocytes eluted between 15 and 17.5 min. The leukocyte:erythrocyte ratio increased from 1:700 to 1:19, a 35-fold enrichment. The DEP-FFF was operated under a 10 kHz DEP field with the injection and withdrawal syringe pumps operated at 0.5 and 0.4 mL/min, respectively.

DESCRIPTION OF ILLUSTRATIVE EMBODIMENTS

DEP/FFF may employ a dielectrophoretic force that is balanced against gravitational forces to position cells at different equilibrium heights within a fluid-flow profile. Cells or other particles at different heights in the flow profile may be transported at different velocities, and may therefore be separated via velocity and/or via height differences. In embodiments described herein, the DEP force in DEP-FFF may be generated by applying electrical signals to microelectrode arrays configured on the bottom surface of a separation chamber. In one embodiment, the signal used for separation is a sinusoidal signal with fixed frequency and voltage. Using such an approach, it has been shown that polystyrene beads of different sizes and with different surface modification may be separated. Additionally, DEP-FFF separations of model cell mixtures (cultured breast cancer cells and cultured HL-60 leukemia cells) from normal blood cells has been demonstrated.

Figure 6A:
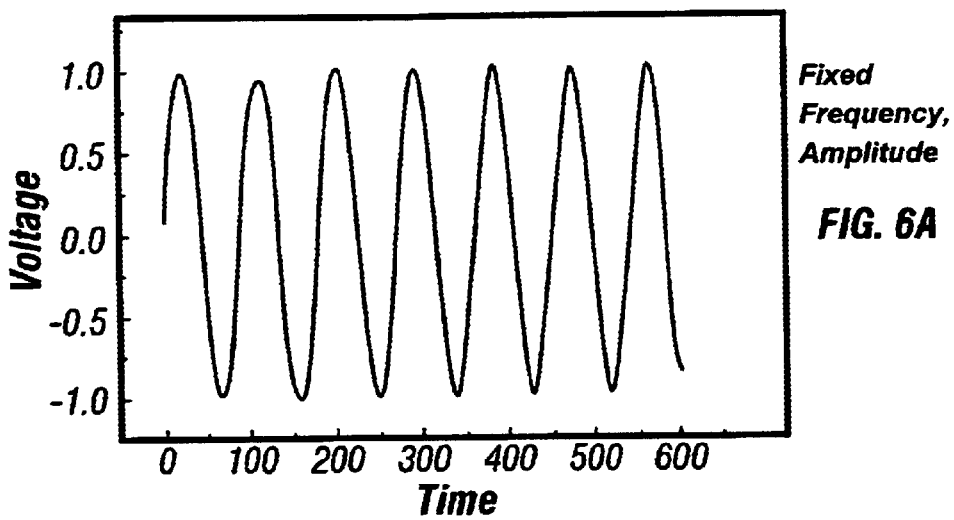
FIGS. 6A–6F illustrate programmable electrical signals that can be applied to electrodes under DEP-FFF operation according to embodiments of the present invention.
Figure 6B:
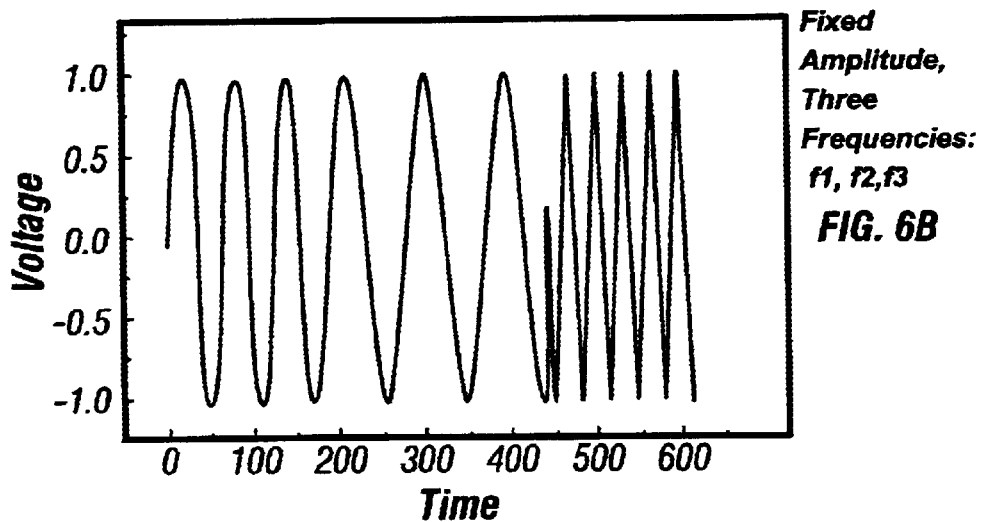
Figure 6C:
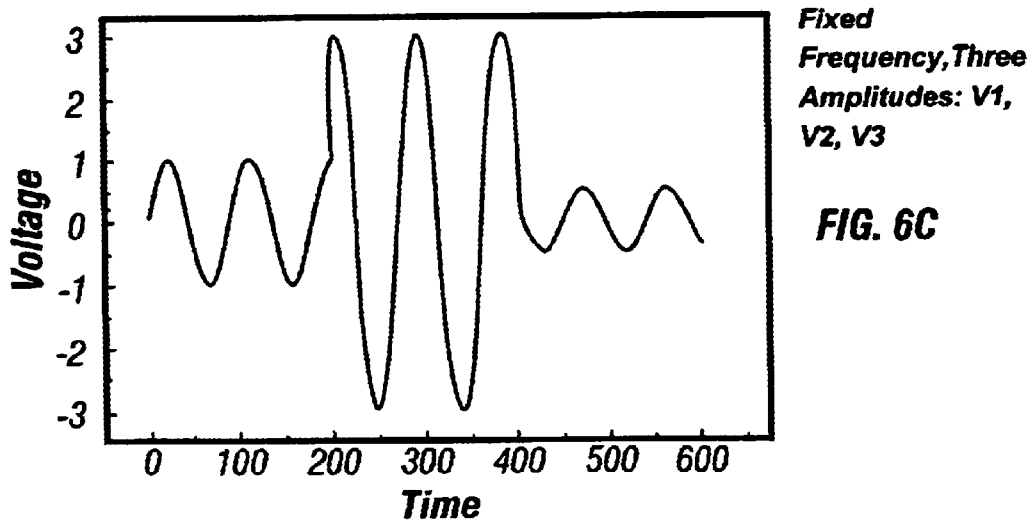
Figure 6D:
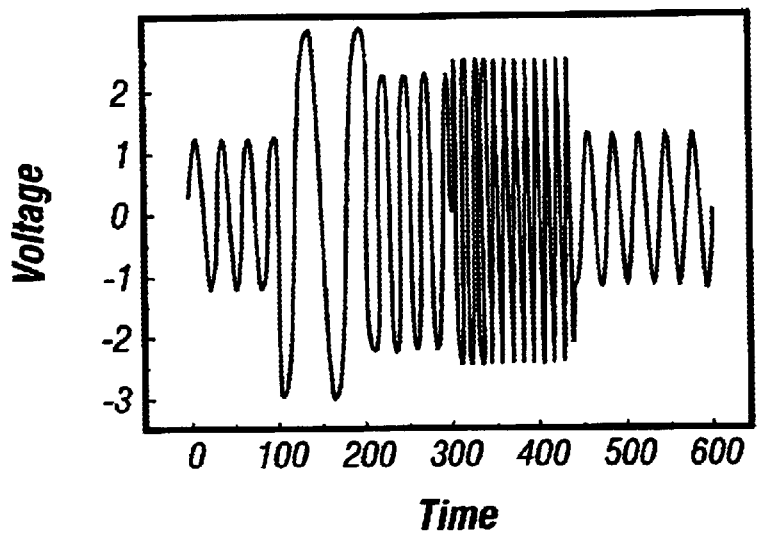
Figure 6E:
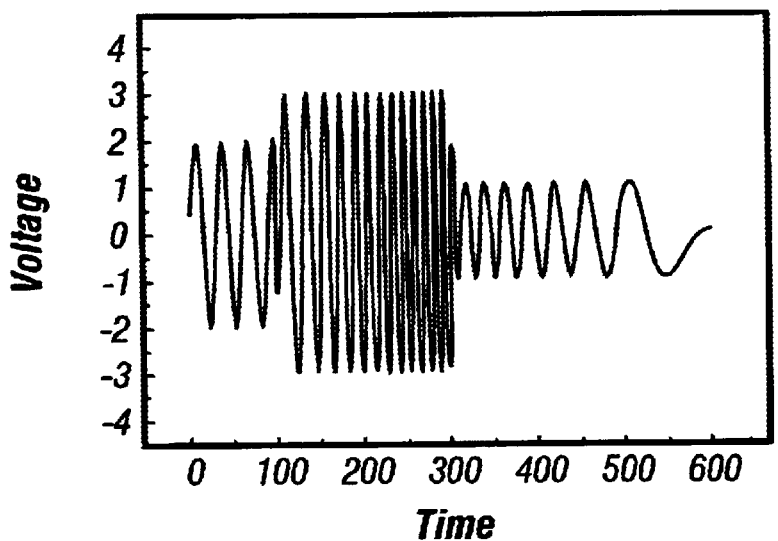
Figure 6F:
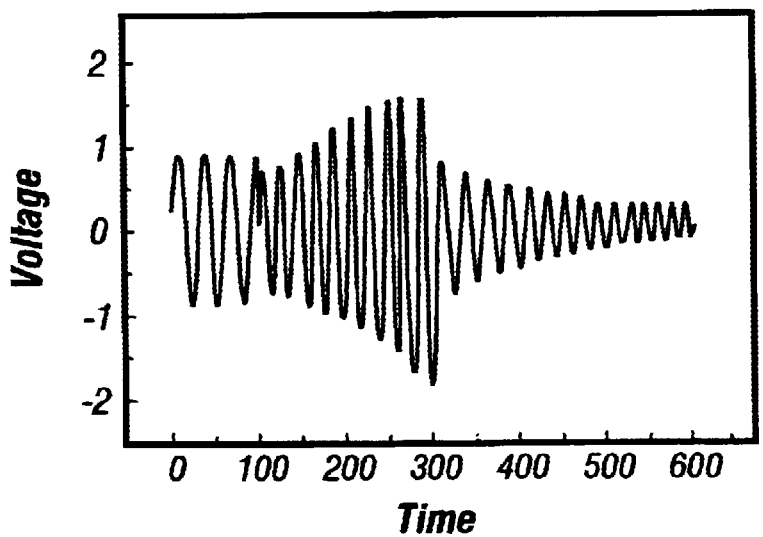

Turning now to FIGS. 6A–6F, there is shown an embodiment that utilizes a dielectrophoretic force field that is programmed and varied by adjusting voltage signals applied to microelectrodes so that the signal amplitude, frequency, waveforms, and/or phases are a function of the time. Specifically, FIGS. 6A–6F show several examples of such "programmed" voltage signals. FIG. 6A shows a signal with a fixed amplitude/frequency. FIGS. 6B–6F depict various embodiments using "programmed" voltage signals, and more particularly, embodiments using time-dependent amplitude/frequency. FIG. 6E and FIG. 6F show signals with frequency-modulation (frequency continuously changes with time) and amplitude-modulation (amplitude continuously changes with time). Applying such signals shown in FIGS. 6A–6F to electrodes described herein, DEP-FFF may be programmed according to specific problems one is facing and according to specific separation goals. By employing such programmed signals, DEP forces may be varied in time for better separation performance and the discrimination of a DEP-FFF separator may be tailored to specific applications.

Certain DEP-FFF chamber embodiments described herein contain one or two inlet ports and one outlet port. The chamber may be preloaded with a buffer solution. A sample (which, for convenience may be assumed to be made of a cell mixture) may be introduced into the chamber with voltage signals applied to microelectrodes. With electrical signals applied, cells are allowed to settle for some time (e.g., on the order of minutes) to reach equilibrium heights, resulting from a balancing of forces (including dielectrophoretic forces and gravitational forces). A flow profile may then be established in the chamber by driving fluid through at least one inlet port. Fluid exits the chamber at an outlet port. Cells at different heights within the flow profile may exit the chamber at different times because they are transported at different velocities. Exiting cells may be detected using a UV detector, or a flow cytometer, or are collected by a fraction collector.

The speed of DEP-FFF, operation may be increased by using a higher fluid flow rate. However, the maximum-flow-rate may be limited by the cell (or particle) detector one uses because high flow rates lead to excessively high fluid pressure at the cell detector. For example, a HS BRYTE flow cytometer (Bio-Rad, Microsciences Ltd) may operate at up to 50–100 microliters per minute, whilst the flow rate for DEP/FFF operation may range up to several mL per minute. It follows that a separation that may be achieved in the DEP/FFF separator with a flow rate of 5 mL/min would have to be slowed at least 50 fold if an HS BRYTE flow cytometer were used for detection. Such a slow-down is not only inefficient but also means that cells may be subjected to electrical fields and suspended in a non-physiological buffer for 50-times longer, which may lead to undesired effects.

To reduce the fluid pressure at the cell detector downstream from the DEP/FFF separator, a chamber according to the present invention may use two outlet ports, one adjacent the top of the chamber, and one adjacent the bottom of the chamber. Because, in many DEP/FFF applications, cells are levitated to heights less than half the chamber height, the top half of the fluid may not contain any, or may contain only few, cells. Thus, when fluid exiting the top outlet port is withdrawn by an extracting agent, such as a syringe pump, running at half the fluid-flow rate as the chamber inlet port, the great majority of cells or all the cells may exit the chamber at the bottom outlet port. In this embodiment, the fluid flow rate and fluid pressure at the detector may be reduced by half.

In one embodiment, such a two outlet port system may be operated with a fluid-flow-rate through the top outlet port set to more than half the inlet fluid flow rate because cells may occupy much less than half the chamber height. Thus, fluid pressure at the cell detector may be reduced even further. Furthermore, cells exiting the chamber may be at higher concentrations because less fluid exits with them. In the operation of the two outlet port system, the fluid-flow rates at the top and bottom outlet ports may vary with time, provided that the sum of the two equals to the inlet flow rate. Thus, the fluid flow rates at the inlet and outlet ports may be programmed and varied with time during the operation. Such variation in the flow rates with time may speed up the separation process. For example, in the case of the separation of the mixtures of two cell populations, after the complete elution of the first population of cells, the second population may be quickly removed from the chamber by increasing the inlet flow rate and, correspondingly the two outlet-flow rates.

Figure 7:
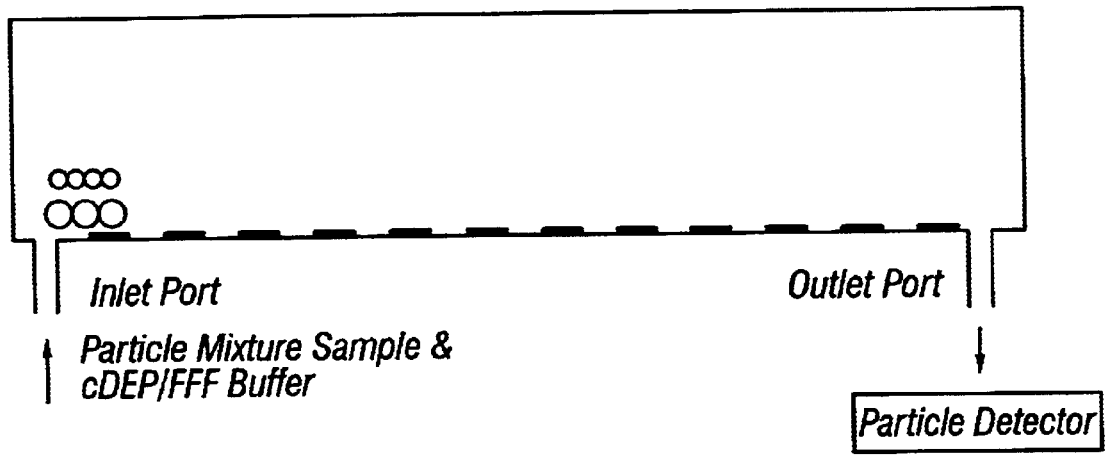
FIG. 7 shows a chamber having a single output port according to one embodiment of the present invention. Particles may be loaded into the chamber and attain equilibrium height positions with respect to the electrode plane on the bottom surface of the chamber. Under the balance of dielectrophoretic and gravitational forces, the smaller particles may be levitated higher than larger particles.
Figure 8:
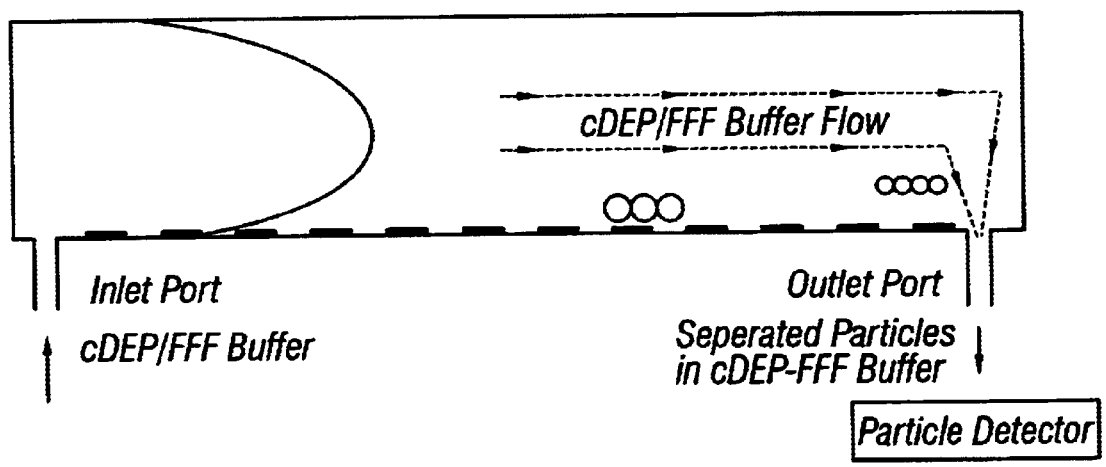
FIG. 8 shows a chamber having a single output port according to one embodiment of the present invention. Particles move under the influence of a fluid flow velocity profile at velocities corresponding to their height positions within the profile. Smaller particles, because of their higher levitation, move faster than larger particles.

In FIGS. 7, 8, 9 and 10, there are shown operating principles for a DEP/FFF chamber in accordance with this embodiment of the present invention n. FIG. 7 and FIG. 8 illustrate DEP/FFF operation for a single outlet port where the particles, which for convenience may be assumed to be a particle mixture, are first introduced into the chamber and equilibrated for some time to attain equilibrium heights (FIG. 7). The particles may then be subjected to a fluid flow profile that separates them as a result of differential velocities at different equilibrium heights. The particles and all the DEP/FFF buffer exits the chamber from the outlet port (FIG. 8).

Figure 9:
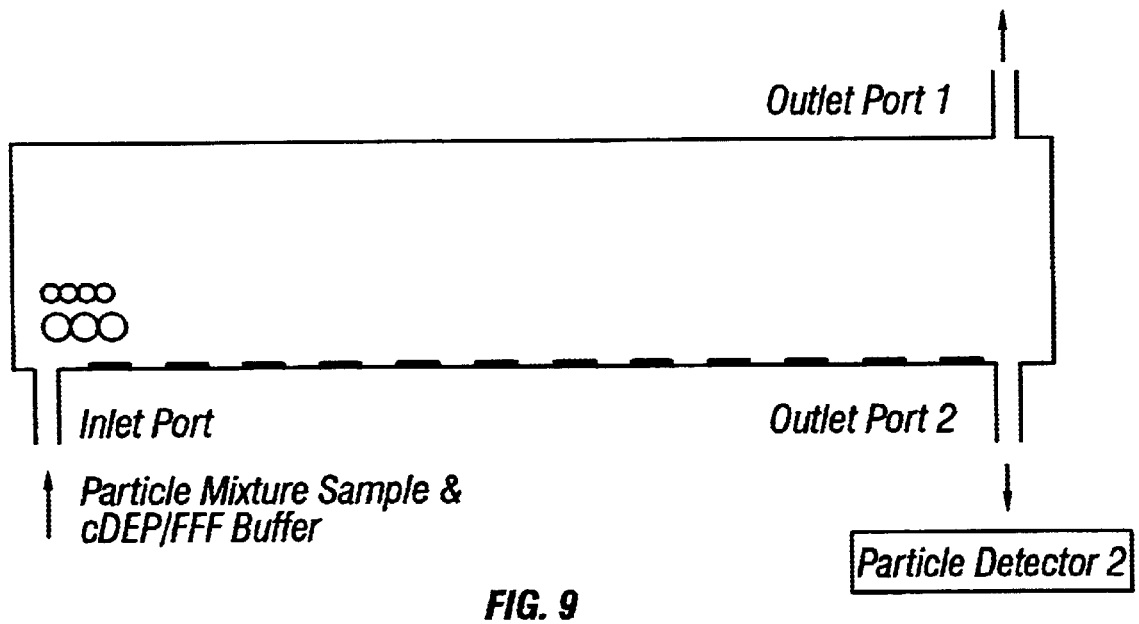
FIG. 9 shows a chamber having a top outlet port and a bottom output port according to one embodiment of the present invention. Particles may be loaded into the chamber and may attain equilibrium height positions with respect to the electrode plane on the bottom surface of the chamber. Under the balance of dielectrophoretic and gravitational forces, small particles may be levitated higher than larger particles.
Figure 10:
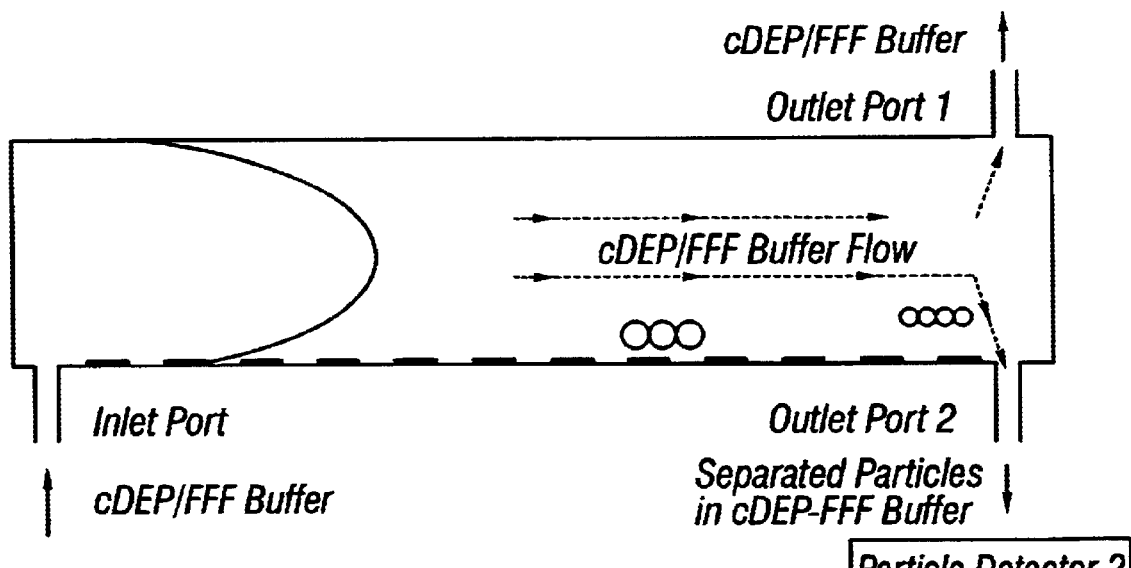
FIG. 10 shows a chamber having a top and a bottom output port according to one embodiment of the present invention. Particles move under the influence of a fluid flow velocity profile at velocities corresponding to their height positions within the profile. Smaller particles, because of their higher levitation, move faster than larger particles. The particles may exit the chamber from the bottom outlet port while a particle-free buffer may be eluted from the top outlet port.

FIGS. 9 and 10 show DEP/FFF operation for an embodiment having a chamber including two outlet ports positioned on the top and the bottom walls of the chamber. FIG. 9 shows that the particles may be introduced into the chamber and allowed to reach equilibrium positions. Particles may then be subjected to a fluid flow profile and are separated as before. However, in this embodiment there are two outlet ports. The particles may exit the chamber from the bottom outlet port while most of the buffer fluid may exit the chamber from the top outlet port (FIG. 10). Depending on the ratio of flow rates at the two outlet ports, the fluid pressure at the particle detector (which may be coupled to the bottom outlet port) may be significantly reduced.

While the description above and many examples given below discuss the DEP/FFF chambers with outlet port(s) from which particles (e.g. cells) are eluted, the inventors envisage embodiments of the present invention in which the particle detectors are integrated with the DEP/FFF separation chamber. In one embodiment, particle detection may be based on the electrical impedance change between two sensing electrode elements (see, e.g., electrodes illustrated as dashed line segments in FIG. 7) located at the two opposite sides of a channel when particles flow through the channel. Such electrode elements may be fabricated using the same methods as those for making DEP separation microelectrodes, and the channel may be on the same substrate (e.g. glass or silicon) as that for the separation electrodes. In such cases, particle separation and detection are accomplished in the same integrated device.

Figure 11:
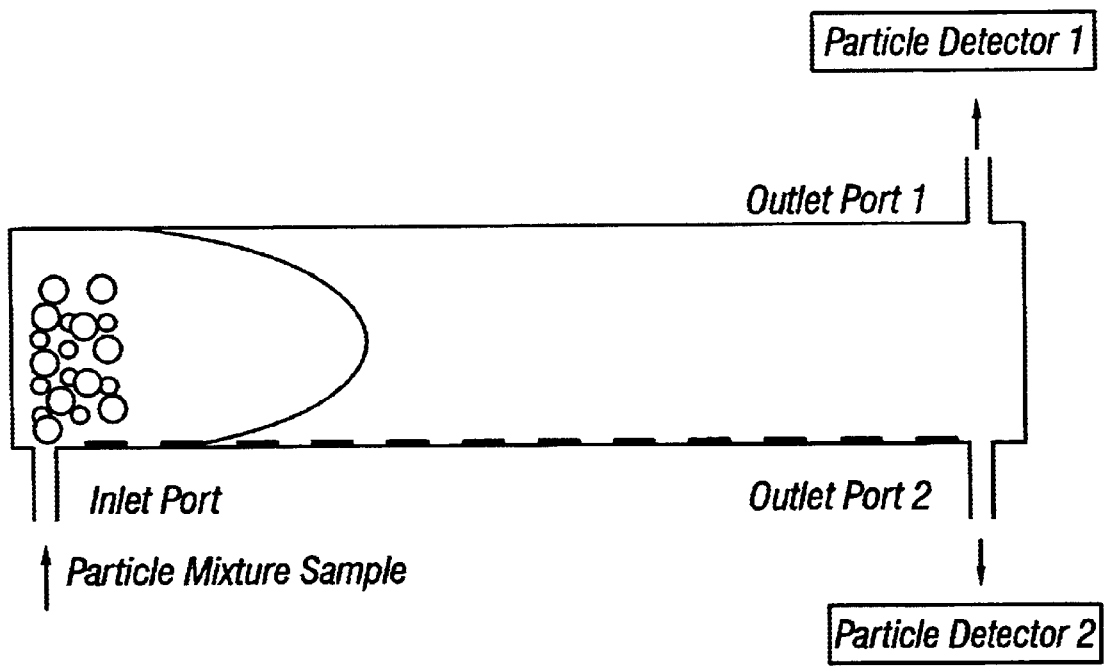
FIG. 11 shows a chamber having a top outlet port and a bottom output port according to one embodiment of the present invention. The chamber may be operated at a continuous separation mode where particle mixtures are continuously introduced into the chamber.
Figure 12:
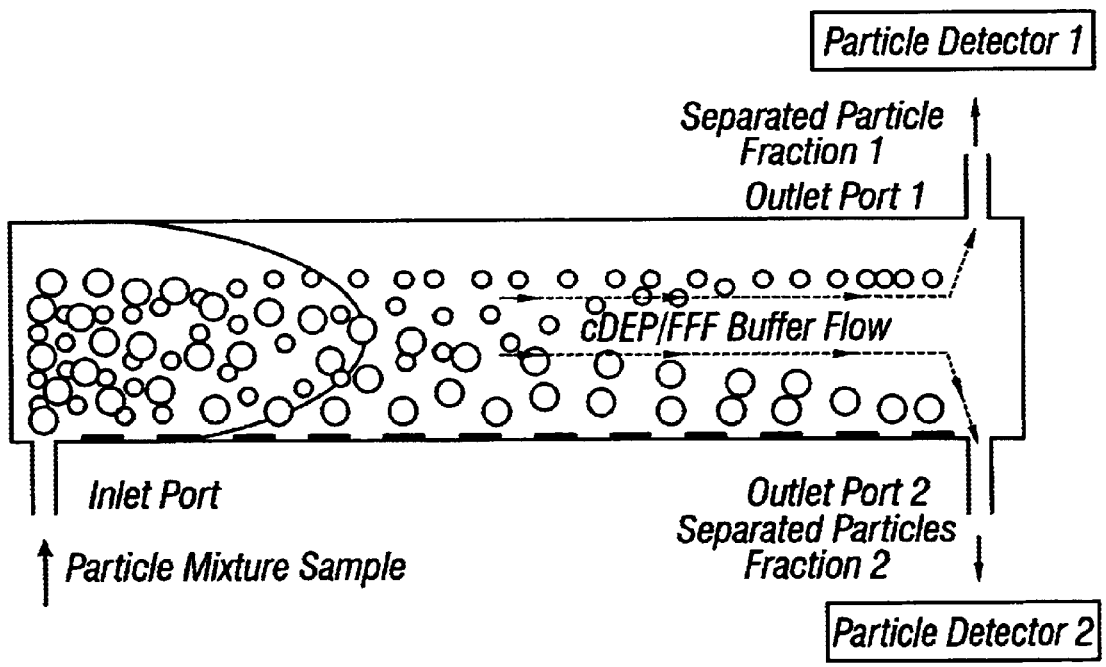
FIG. 12 shows continuous mode operation of a chamber having a top outlet port and a bottom output port according to one embodiment of the present invention. The particle mixtures may be continuously introduced into the chamber and may be transported through the chamber under the influence of the fluid flow. Simultaneously, particles may be subjected to dielectrophoretic forces generated by electrodes on the chamber bottom-surface and to gravitational forces and may move in the vertical direction. As particles reach the end of the chamber, smaller particles attain higher positions and exit the chamber from the top outlet port while larger particles attain lower positions and exit the chamber from the bottom outlet port.

Continuous DEP/FFF particle separation using DEP-FFF chambers with multiple outlet ports By increasing the fluid flow rate from the upper fluid outlet port of FIG. 10, particles may be withdrawn from the top. Indeed, by adjusting the ratio of flow rates through the top and bottom outlet ports appropriately, desired fractions of cells may be caused to exit through those respective ports. In this embodiment, the particle mixture need not be injected as a single batch and separated in time, but instead may be continuously introduced in the chamber (FIGS. 11 and 12). Particles are carried with the fluid flow. Simultaneously, they move in the vertical direction to reach equilibrium heights determined by their properties and the balance of forces such as dielectrophoretic levitation and gravitational forces (FIG. 12). If the fluid flow rate is controlled appropriately, particles may reach their equilibrium height positions before they arrive at chamber outlets. As fluid exits the chamber from both the top and the bottom outlet ports, the fluid from the bottom surface up to a certain height (a threshold height) in the chamber will exit the chamber through the bottom outlet port while fluid above the threshold height will exit through the top outlet port. Particle having equilibrium heights lower than the threshold height exit the chamber through the bottom outlet port (FIG. 12). On the other hand, particles having equilibrium heights above the threshold height exit the chamber through the top outlet port (FIG. 12). Separation may thus be achieved according to particle heights as particles reach the chamber outlet end. Such separation may be operated in a batch, or alternatively, a continuous mode as the height-differential between different particles are exploited for separation directly, without need for exploiting differential velocities created by the fluid flow profile.

Again, the height-differential between different particle types may be the basis of the differential velocity and exit time for batch-mode DEP-FFF operation, as described herein. Using the two port system of FIGS. 11–12 eliminates the need for a flow profile, and it enables continuous separation.

In the embodiment of FIGS. 11–12, particles do not have to reach their equilibrium positions as they arrive at the chamber outlet end. As long as there are sufficient differential heights between sub-populations of particles to be separated, the continuous DEP-FFF operation may separate particles. Because flow profile is not actively exploited in this embodiment, separation may be performed even for a "plug-like" flow profile—this opens the possibility that fluid flow may be generated by effects such as electro-osmosis or surface acoustic wave, rather than by a typical syringe pump. Nevertheless, flow profile does influence the time cells take to travel through the chamber the time that is available for particles to "move" in the vertical direction under the combined action of the dielectrophoretic levitation and sedimentation forces—so it may influence, in turn, the distribution of particle vertical positions as they exit the chamber.

FIGS. 11 and 12 show embodiments of the DEP/FFF principle of continuous separation with two outlet ports. In this embodiment, particle may be continuously fed into the DEP-FFF chamber and transported by fluid flow to the chamber outlet ports. As the particles are transported, they experience vertical DEP and gravitational forces that drive them up or down. Different particle types, possessing different dielectric properties and therefore experiencing different dielectrophoretic forces, attain different heights as they reach the end of the chamber. Because there are two outlet ports, some particles, depending on their height positions, exit the chamber at the bottom outlet port and others at the top outlet port. Although a typical parabolic profile is drawn in the figure for the fluid flow, those having skill in the art, with the benefit of the present disclosure, will recognize that the illustrated flow profile is not necessary.

In one embodiment, multiple outlet ports may be placed on the bottom or bottom plates of the chamber. Particles being separated may exit from such outlet ports, again, depending on their relative position in the chamber.

While chambers used for continuous separation may be similar to those used batch mode, important differences lie in the fact that flow rates through the top and bottom ports may be chosen in continuous mode so that particles of different types may exit the chamber through the top and bottom outlet ports. Thus the fluid flow rate, chamber thickness, the particle levitation properties may all have to be taken into account when designing separation protocol to ensure that a separation would work as desired.

In one embodiment of continuous DEP/FFF separation may include the use of a splitter at the outlet end of the chamber. Such a splitter may be several to tens of micrometers, and may be used to divide the fluid at the outlet end of the chamber into multiple fractionations.

Programming DEP Force Field for DEP-FFF Separation

In one embodiment, voltage signals at an amplitude $V_1$ and a frequency $f_1$ may be applied for a certain time period (any time ranging from about 10 seconds to about 60 minutes). During this signal mode, the difference in particle height and velocity may be maximized by reducing the velocity of one particle type as much as possible (ideally, down to zero) and increasing the velocity of other particle types to large values (typically 10 cm/min). After some time, sufficient separation between the particle in the chamber may be achieved or the fast-moving particle type will have already exited the chamber. Then, a different voltage signal at an amplitude $V_2$ and a frequency $f_2$ may be applied. In this case, the velocities of both particle types may be increased, so that both particle types are eluted quickly from the chamber while a good separation between the two populations is maintained.

In another embodiment, a signal having a constant amplitude but a sweeping frequency (for instance, frequency linear modulation by a triangular waveform) may be first applied to electrodes. Such a signal, while it may not affect the elution characteristics of certain particle types having relatively large polarization factors in the applied frequency range, may be important for particle types having a polarization factor close to zero. Such sweep-frequency signals may reduce the number of the particle that would be trapped on the electrode plane and ensure that these particles move slowly. Such a sweep-frequency voltage signal, after being applied for some time, may lead to separation of the particle subpopulations in the chamber. After such a frequency-sweep step, signals of fixed frequency may be applied to elute all the particle types remaining in the separation chamber.

In another embodiment, for separating particle mixtures (e.g., cell mixtures) having multiple subpopulations, electrical signals of constant amplitude may be applied with the signal frequency being changed in a step wise fashion. An example of this embodiment may involve a sample containing three subpopulations ($S_1$, $S_2$ and $S_3$), having different dielectric properties and different polarization factors. Signals of frequency $f_1$ would be applied to delute subpopulation $S_1$, whilst ensuring slow movement of subpopulations $S_2$ and $S_3$. After subpopulation $S_1$ is eluted from the chamber or is moved far ahead of the other two subpopulations, subpopulation $S_2$ may be eluted by changing the signal frequency to $f_2$ whilst still ensuring slow movement of subpopulation $S_3$. After another time period, subpopulation $S_2$ may be eluted or moved sufficiently ahead of $S_3$. Finally, a signal of frequency $f_3$ may be applied to rapidly elute subpopulation $S_3$. With the benefit of the present invention, those having skill in the art will recognize that such an approach may be modified in numerous ways to separate cells or particles having multiple subpopulations. Furthermore, alternative or additional step-wise changes in signal amplitude, amplitude and frequency, sweeping-frequency, or any other property of the signal may be used to improve separation as appropriate for each application. For instance, signals having two or more components (e.g., having frequency $f_1$ and $f_2$ and intensities $V_1$ and $V_2$) may be applied simultaneously and programmably for certain periods of time.

In the embodiments disclosed herein, programming a DEP force field as a function of time for DEP/FFF separation may not only maximize particle separation but also may allow for fast separation. The sweeping frequency has an important advantage in that it may allow many particles of the same type to be levitated slightly even though their dielectric properties are quite different. Without using such a sweep-frequency signal, some particles may be levitated, but others may experience positive DEP forces that cause them to be trapped on one or more electrodes (undesired effects).

As described above, the programming DEP force field as a function of time may allow the flexible control for the DEP-FFF separation process. For example, the frequency of the voltage signals may be gradually and step-wisely reduced to allow the elution of various cell sub-populations. The programming of a DEP force field may be readily achieved by controlling one or more signal generators with a computer or another suitable controller. In this way, optimal separation-conditions may be found by testing various signal combinations.

Two Outlet Ports for DEP-FFF Chambers

A DEP-FFF chamber was constructed, in accordance with one embodiment of the present invention, with two outlet ports, one each on the top and the bottom walls. Particles or cells exiting through the bottom outlet port were detected by flow cytometry. In one embodiment, the total fluid flow rate in the DEP-FFF chamber was between 0.5 and 2 ml/min, but it will be recognized that the rate may vary widely. In this embodiment, to ensure that the fluid flow rate through the flow cytometer was less than 0.1 ml/min., up to about 95% of the fluid exiting the chamber was drawn from the top outlet-port. So, for example, at a total fluid flow rate of 0.5 ml/minute, fluid was withdrawn from the top outlet port by a syringe pump at a rate of 0.4 ml/min, lowering a residual flow to the flow cytometer at 0.1 ml/min. Again, the inlet and two outlet flow rates may be programmed so that they vary with time.

In choosing operating conditions for a two outlet port system with one detector at the bottom outlet port, it may be important to make sure that all particles (or cells) exit from the bottom port. Otherwise, some particles (or cells) may go undetected or uncollected if they are eluted from the top outlet port. In this two-port DEP-FFF embodiment, the 2nd outlet port is used to reduce the fluid pressure at the bottom outlet port so that particles or cells may be detected using apparatus such as flow cytometer. Another benefit of such an embodiment is that the separated particles or cells are "concentrated", in that diluting fluid is withdrawn from the top outlet port.

Embodiments described herein allow for programmable DEP force fields via programmable voltage signals, multiple outlet ports, and continuous DEP-FFF particle separation. These embodiments, and R-combinations thereof, provide for several significant advantages. For instance, better-particle (or cell) separation may be achieved. In one embodiment, purity of separated populations was increased from 70% using a single-frequency field to greater than 99% with a sweep-frequency field. Separation may be performed faster and more flexibly. In one embodiment, a separation time was improved from 40 minute using a single-frequency field and a single outlet port to 5 minutes with a programmed DEP force field on a chamber having two outlet ports. A significant reduction of fluid pressure and flow requirements of any down-stream particle (or cell) detector or collector may be achieved with the two outlet port arrangement. In one embodiment, greater than a 10 fold reduction was achieved in fluid pressure. DEP-FFF separation may be operated at higher flow-rates so that fast separation may be performed. Two ports may allow for lower dilution factors for separated cells. In one embodiment, concentration was increased by a factor greater than ten. Continuous separation embodiments may allow for the processing of large quantities of cell samples and may be particularly applicable to the case where one cell type to be separated is of low concentration (such as separating metastatic cancer cells from mononuclear cells, or white blood cells from red blood cells).

Such advantages are applicable to all DEP-FFF separation problems, including synthetic particle separation (including surface activated beads) and cell separation (including, but not limited to, blood cell differential analysis, erythrocytes from leukocytes, nucleated erythrocytes from erythrocytes/leukocytes, fetal erythrocytes from maternal blood, activated cells from non-activated cells, malarial-infected cells from normal blood cells, metastatic cancer cells from blood, cancer cells from bone marrow, cancer cells from normal counterpart cells, and leukemia cells from blood).

The following additional examples are included to demonstrate illustrative embodiments of the invention. It should be appreciated by those skilled in the art that the apparatus and techniques disclosed in the examples which follow represent devices and techniques discovered by the inventor to function well in the practice of the invention, and thus can be considered to constitute preferred odes for its practice. However, those of skill in the art should, in light of the present disclosure, appreciate that many changes can be made in the specific embodiments which are disclosed and still obtain a like or similar result without departing from the spirit and scope of the invention. While the following examples use the term particle, the skilled artisan will realize that the present apparatus and methods are suitable to solubilized matter as well.

EXAMPLE 1

Figure 1A:
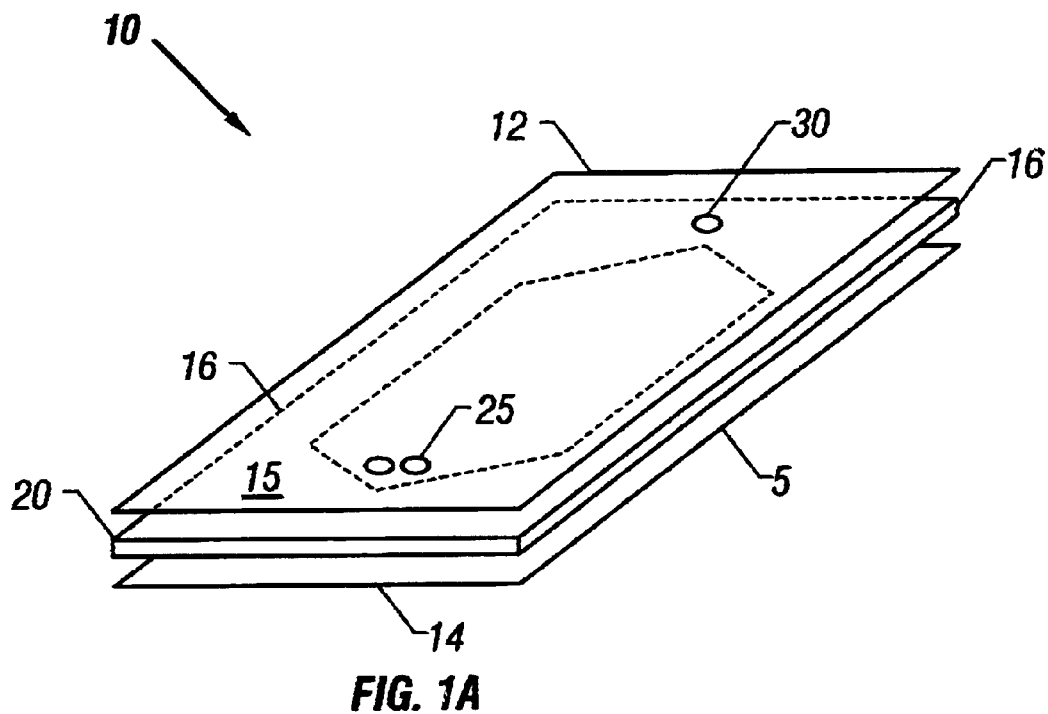
FIG. 1A is a block diagram of an apparatus according to the present invention.
Figure 1B:
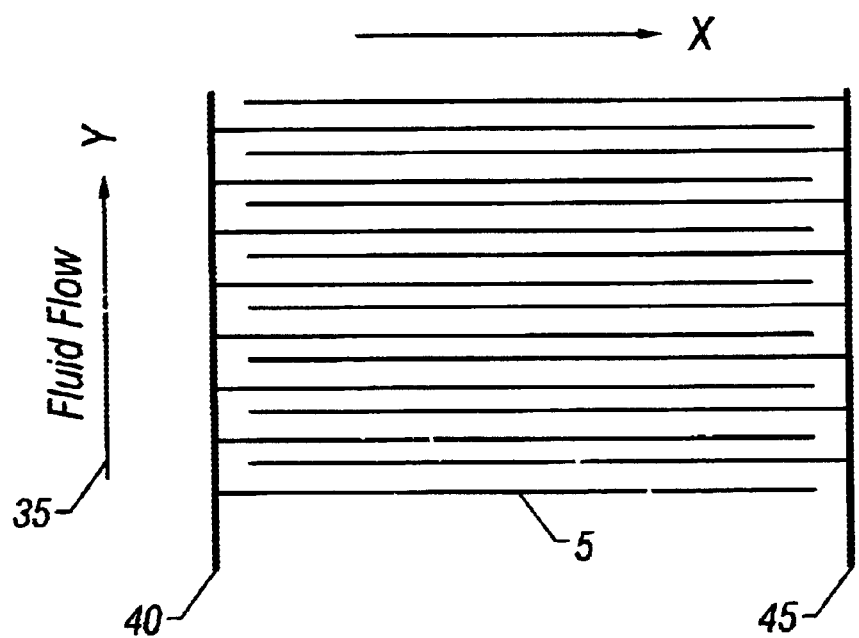
FIG. 1B is a diagram a parallel (interdigitated) electrode array is positioned normal to a fluid flow.

FIG. 1A shows one exemplary embodiment of an apparatus according to the present invention. In this figure, the electrode array 5 is placed on the bottom wall 14 of a chamber 10; however it is contemplated that the electrode array may be placed on the top wall 12 and/or bottom wall 14 and/or side walls 16 of a chamber constructed in accordance with the present invention. As shown in FIG. 1B, the electrode array 5 may be placed along a chamber wall in a position normal to a flow of fluid 35 through the chamber 10. It is to be noted that the array may be adapted at any angle with respect to the fluid flow, for example, parallel or at any other angle. In this embodiment, the walls are aligned to create a thin chamber. The walls are spaced apart by a spacer 20, which may be, for example, constructed of the same material as the chamber walls, or a TEFLON spacer, a sealing compound, or any other dielectric or conductive material. Electrical signals applied to the electrode array create an inhomogeneous alternating electric field that varies with the frequency and magnitude of the input signal. In a particular embodiment, the electrode element 5 may be adapted to be substantially normal to the fluid flow 35, as shown in FIG. 1B. Further electric conductors, which may be electrode buses 40 and 45 may provide electrical signals to alternate elements of electrode array 5. The strength of the electric field is dependent on the applied voltage, the position within the chamber, and the size and spacing of electrode elements. For manipulation of mammalian cells, the field strength may be on the order of or less than approximately $10^6$ V/m, although this may be much higher for matter placed in an oil medium. The particulate matter desired to be discriminated is introduced into the chamber in a carrier medium that flows into at least one inlet port 15. There may be more than one inlet port however, which permits input of the carrier medium. The carrier medium may be input by a digital syringe pump, a manual syringe, a peristaltic pump, a gravity feed catheter, or the like. As discussed above, the particulate matter may include, for example, biological molecules and non-biological molecules. Also, the matter may include solubilized matter. The carrier medium may be, for example, an eluate consisting of a cell-free suspension buffer, including a mixture of sucrose and dextrose, tissue culture medium, non-ionic or zwitter ionic solutes, or other suspension mediums or non-biological oils, solvents such as phenol alcohol, $CCl_4$, ethylene glycol, or others known in the art. Alternately, one or more ducts 25 may be provided to input a fluid which may be flowed through chamber 10.

The carrier medium is caused to flow through the chamber and thereby create a laminar flow profile in which the fluid flow velocity increases with increasing distance from the chamber top and bottom walls, and reaches its maximum at the center. However, by adjusting the shape of the chamber, for example, a flow profile may be created in which the maximum is at a location other than the center of the chamber. In an exemplary embodiment, the total flow rate through the chamber may be on the order of about 0.01 ml/mn. to about 5000 ml/min., and more preferably about 1 ml/min. to about 20 ml/min. The electric field applied to the electrode elements 5 creates dielectrophoretic forces on the particles in accordance with their dielectric and conductive properties as well as those of the carrier medium.

Figure 1C:
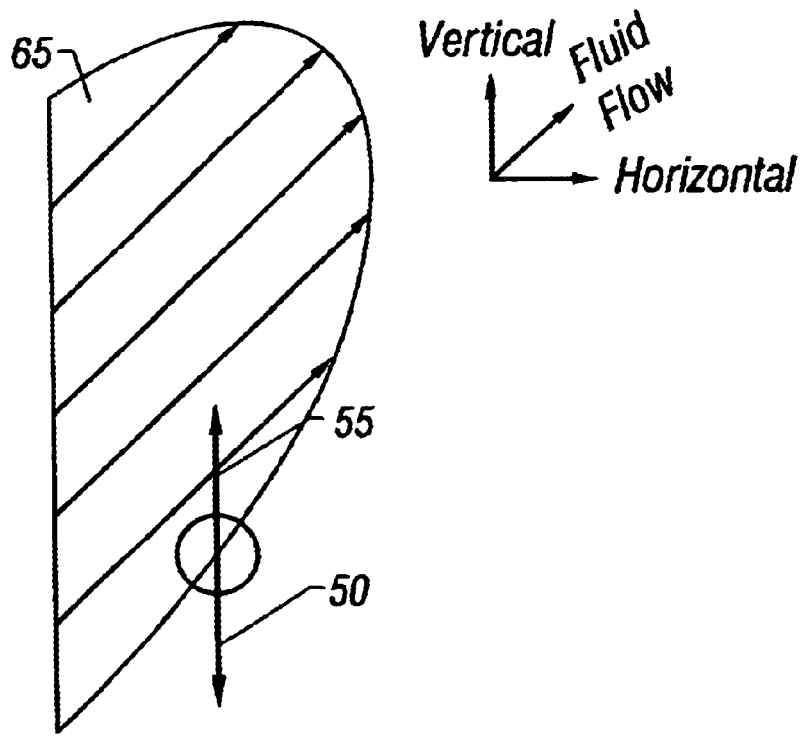
FIG. 1C is a force diagram of the apparatus of FIG. 1A.

By controlling the frequency and/or intensity and/or waveform of the applied electric signals, the component of the dielectrophoretic force that is normal to the flow direction of the carrier medium is controlled so as to cause the particles to equilibrate at characteristic distances from the electrode element 5 creating the electric field. These characteristic distances are referred as equilibrium heights at which the DEP forces in the vertical direction are balanced by gravitational forces and hydrodynamic lifting forces acting on the particles. The dielectrophoretic force operates in conjunction with the action of the combined hydrodynamic lifting forces and gravitational forces as shown in FIG. 1C. FIG. 1C shows how these forces act on matter within the chamber 10. Specifically, FIG. 1C shows the gravitational force 50 acting in a downward direction and the dielectrophoretic force 55 and hydrodynamic lifting force 52 acting in an upward direction. The flow velocity profile 65 along the vertical plane has a maximum at the center of the chamber, and a minimum velocity at the top and bottom of the chamber. Since the dielectrophoretic force acting on each individual particle depends upon its dielectric permittivity and electrical conductivity at the applied frequency, as well as upon its volume, particles having different properties will be positioned at different distances from the electrode element creating the electric field. Because the fluid at different heights above the chamber bottom wall flows at different velocities, particles having differing physical properties will travel through the chamber 10 at different speeds and emerge at an outlet port 30 at different times. It is to be understood that there may be more than one outlet port from which to collect the particulate matter which exits the chamber 10.

EXAMPLE 2

Figure 2E:
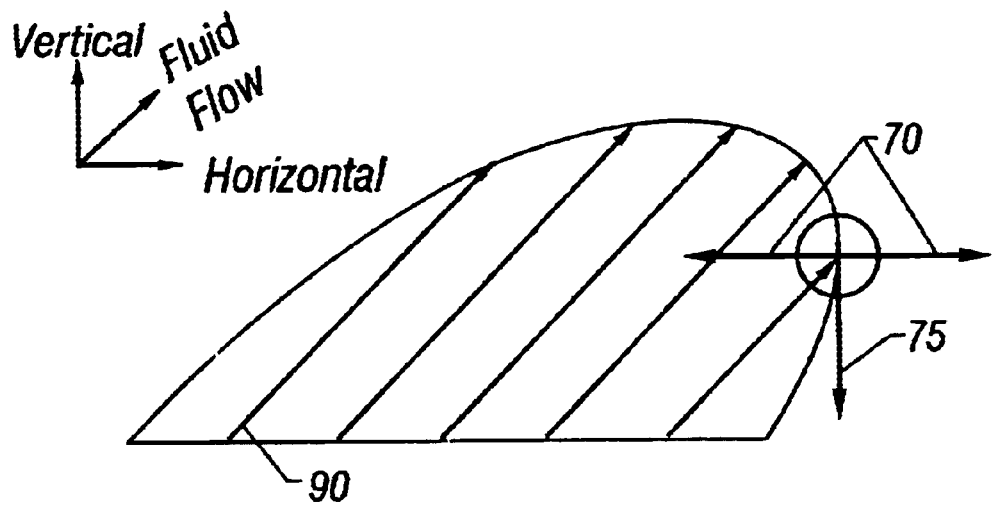
FIG. 2E is a force diagram of the apparatus of FIG. 2A.
Figure 2A:
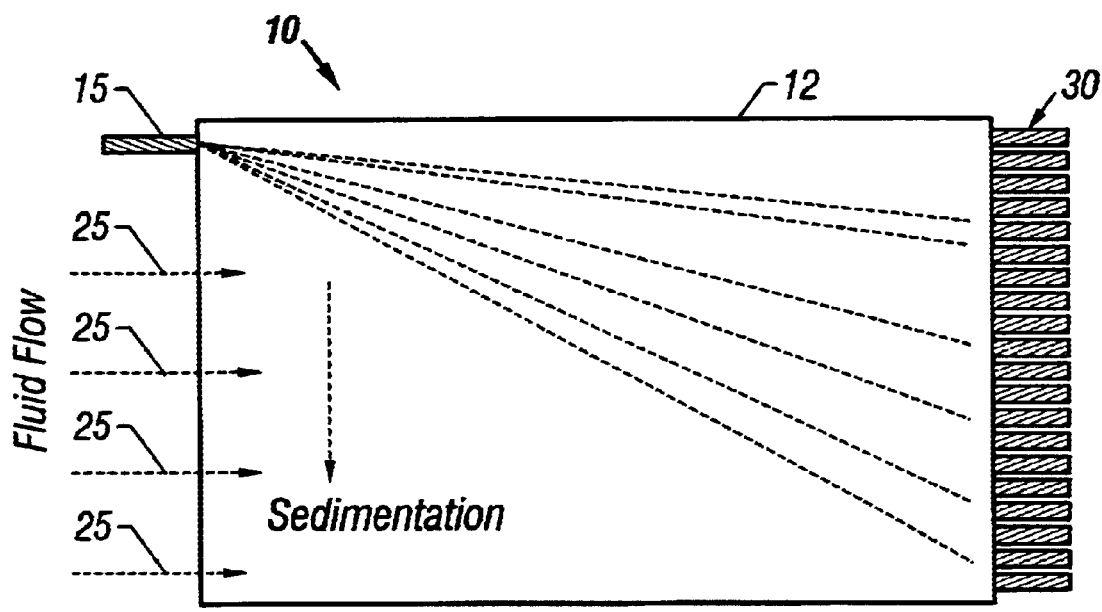
FIG. 2A is a side view of an apparatus according to the present invention which describes a typical trajectory of matter introduced into the apparatus.
Figure 2B:
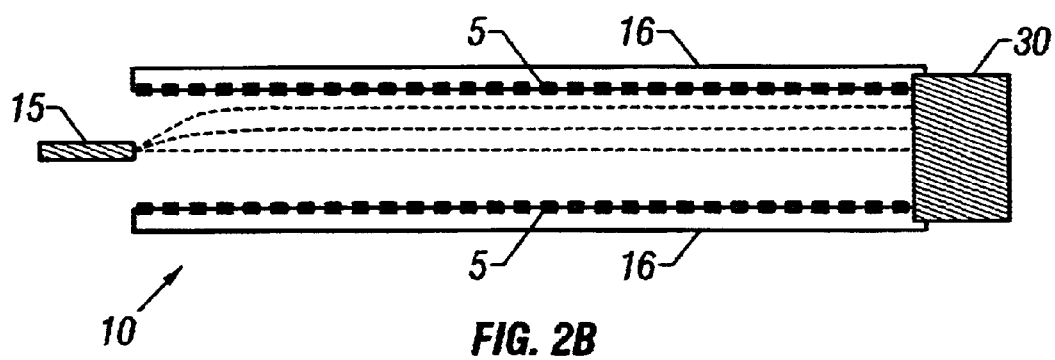
FIG. 2B is a top view of the apparatus of FIG. 2A which describes a typical trajectory of matter introduced into the apparatus.
Figure 2C:
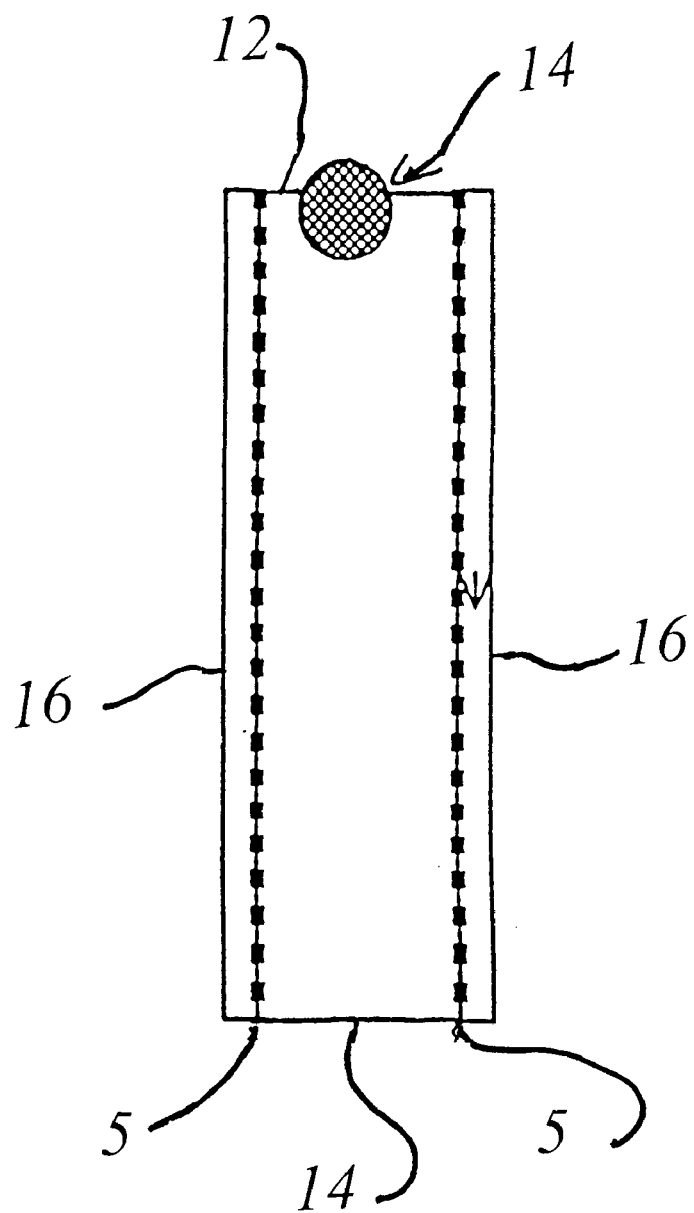
FIG. 2C is an end view of the apparatus of FIG. 2A.
Figure 2D:
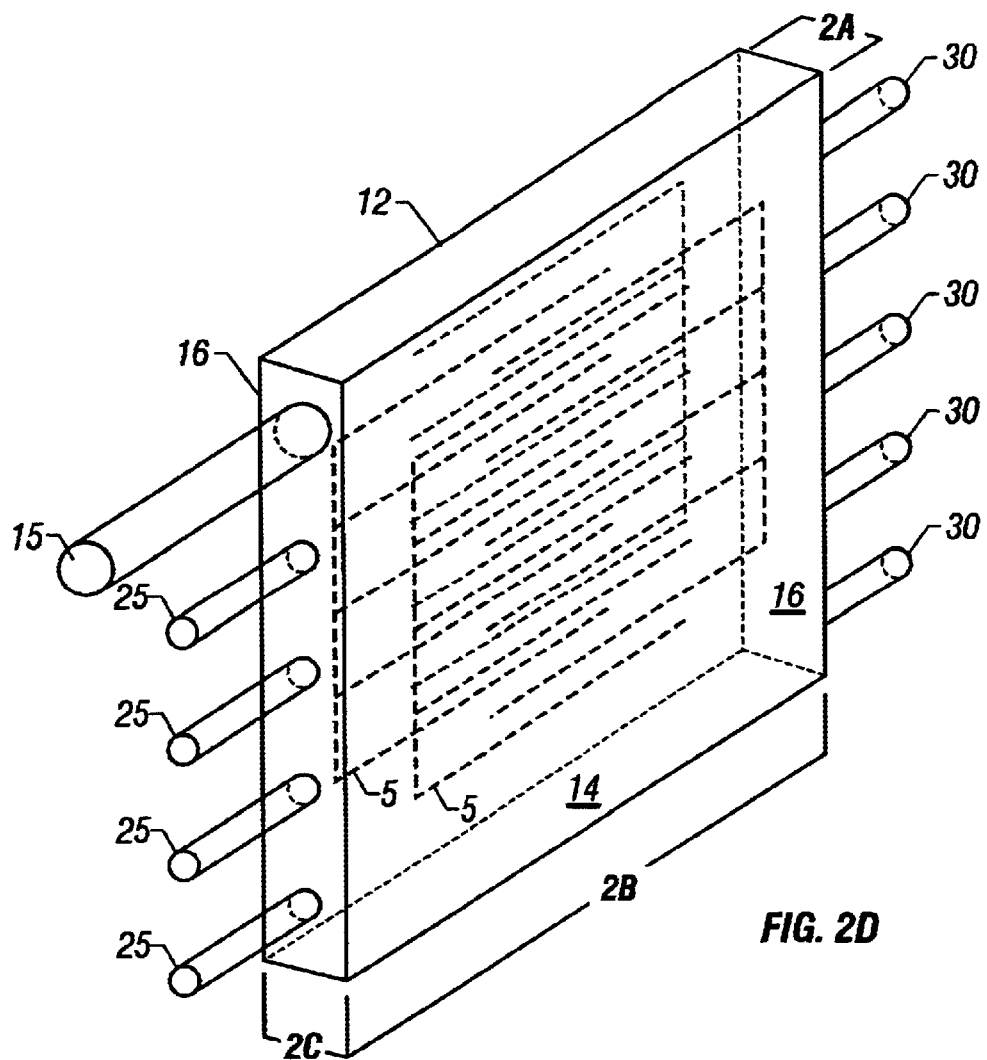
FIG. 2D is a three-dimensional view of the apparatus described in FIGS. 2A–2C.

FIG. 2D is a three-dimensional view of a second apparatus according to the present invention, as shown more fully in FIGS. 2A through 2C. FIG. 2A shows a second embodiment of an apparatus according to the present invention that includes a chamber 10 having two facing electrode arrays 5, as shown in FIGS. 2B and 2C, on opposite surfaces of the chamber. The chamber is turned so that the electrode planes 5 stand substantially vertical. In this embodiment, the chamber is arranged so that the thin sides of the chamber are vertically arranged. It is understood, however, that the electrode planes need not be only vertical, and the present invention contemplates adapting the apparatus at varying angles. Different electrical signals (frequency, magnitude and waveforms) are applied to the facing electrodes from the signal generator so that particles experience different DEP forces from the field produced by each array 5. Further, within each facing electrode array 5, different electrical signals may be provided by the signal generator to create an inhomogeneous alternating electric field.

This alternate apparatus may have, for example, a top wall 12, a bottom wall 14, and two side walls 16. Further, the apparatus may have one inlet port 15 adapted to receive the particulate matter to be discriminated. The inlet port 15 may be located, for example, close to the top of one end of the chamber 10. This apparatus may also include one or more ducts 25 to introduce a fluid that travels through the chamber 10. The ducts 25, which may be arranged substantially along the entire width of the input end of the chamber 10, serve to introduce a sheet of fluid that travels throughout the chamber 10 in a substantially linear direction.

The introduced fluid carries the particulate matter through the chamber 10. This fluid may be, for example an eluate, such as a cell-free suspension having a mixture of dextrose and sucrose, tissue culture medium, non-ionic or zwitterionic solutions, or other suspension mediums or non-biological oils, solvents such as phenol, alcohol, $CCl_4$, ethylene glycol, or others known in the art. Following transit through the chamber 10, fluid leaves at the opposite end through an exit port. This exit end of the chamber 10 may include, for example, one or more exit ports 30, which may be arranged in one or more arrays of ports as shown in FIG. 2A. In the absence of an applied field, that is, when no electrical signal is applied to the electrode elements 5, particles move through the chamber 10 under the influence of fluid flow. Further, based on the geometrical design of the fluid may exhibit, for example, a laminar flow-velocity profile, in which the speed of the flow is fastest towards the center of the chamber 10 as shown in FIG. 2E. That is, the hydrodynamic flow profile is along a horizontal plane. Simultaneous to the influence of the fluid flow, the particles undergo sedimentation due to gravitational forces on the particles, so that they exit the chamber 10 at characteristic heights determined by their sedimentation rates as shown in FIG. 2B.

When electrical signals are applied, however, the particles experience DEP forces that cause them to move to characteristic distances, known as an equilibrium position, from the side walls of the chamber 10 where the electrode arrays 5 are arranged. At equilibrium positions, DEP forces due to the electrical fields generated by the two facing electrode arrays balance each other. Interaction of the gravitational and dielectrophoretic forces on matter are shown on FIG. 2E. FIG. 2E shows that the dielectrophoretic forces 70 act in a horizontal direction and the gravitational force 75 in a vertical direction. The flow velocity profile 90 along the horizontal plane has a maximum at the center of the chamber, with the velocity diminishing at the sides of the chamber. In this embodiment, different electrical signals (frequency or magnitude or both or waveform) are applied to electrode elements 5 on each of the side walls. Particles having different dielectric and conductive properties equilibrate at different characteristic distances (or equilibrium positions) from the side walls of the chamber, based on the synergism of the differing electrical signals, which create an inhomogeneous electric field, causing DEP forces on the particles. Such particle equilibration positions with respect to the electrode elements on the chamber side-walls depends on the dielectric and conductive properties of the particles, the magnitude and frequency of the electrical fields applied to the electrodes on the facing chamber walls, and the fluid density, viscosity and flow rate as shown in FIG. 2B. Particles introduced into chamber 10 moves to different equilibrium positions from electrode array 5. The velocities of the different particles within the fluid are controlled by the velocity profile of the fluid and their positions within such a velocity profile. Because fluid flowing through a thin chamber sets up a velocity profile, particles that have equilibrated at different distances from the chamber walls will be carried at different velocities and therefore take varying amounts of time to traverse the chamber. The fluid flows at a maximum velocity towards the center of the chamber, with this velocity proportionately diminishing as distance to the side walls decreases. Depending on applications and chamber dimensions, the overall fluid flow rate through the chamber may be between about 0.01 ml/min. and about 5000 m/min., and more preferably between about 1 ml/min. and about 100 ml/min.

The skilled artisan will recognize, however that variations in the dimensions of the apparatus will affect the fluid flow rate, and that the indicated flow rates are illustrative for the dimensions of the present apparatus.

Gravity forces act on the particles during their transit through the chamber. The distance that particles sediment during their passage across the chamber will depend upon their transit time and the sedimentation rate (or velocity). Consequently different particles will sediment to different depths based upon the particle's transit time through the chamber 10 and the particle's sedimentation rate. Particle sedimentation rate may depend on particle characteristics, such as size, mass, and volume, for example. As described above, the time required for particles to travel across the entire length of the chamber is controlled by the fluid flow profile and the positions of particles within the flow-velocity profile. The placement of particles within the fluid flow profile is in turn determined by the synergism of the differing electrical signals. Thus, particles with different characteristics (e.g.: dielectric property, size) may be placed at different positions in the flow profile and therefore exhibit different transit times. The combination of differences in transit time and in sedimentation velocity between particles of different properties (e.g. dielectric property, density, size) may lead to different sedimentation depths for these particles. They may exit the chamber through different exit ports which are placed at different heights along the entire outlet end. Discrimination may be accomplished either in "batch-mode" or in "continuous mode." In batch mode, an aliquot of particles is injected and collected with respect to the time of transit for the particles and the height of exit at the outlet ports 30. In continuous mode, a constant stream of particles is injected into the inlet port, and particles emerging at different heights are continuously collected.

In an apparatus according to the present invention, it is possible to vary the carrier fluid characteristics at different heights with respect not only to flow rate but also to fluid density, dielectric permittivity, pH and conductivity. In this way additional particle characteristics may be exploited for particular separation applications.

In the general case, the device may be oriented at any angle to take advantage of discriminating aspects of the horizontal and vertical cases described above. In this generalized situation the particle density, sedimentation rate and dielectric properties, together with all components of the DEP force are utilized. Separation in continuous or batch mode is possible. Different embodiments of an apparatus according to the present invention may have additional components connected to the outlet ports 30. For example, particles emerging from the exit ports 30 of the apparatus of the present invention may be collected by one or more fraction collectors, or the like. Additionally, the matter may be measured by one or more measuring or characterizing structures, such as a cytometer, for example. Furthermore, when necessary, particles may be transferred to collection wells containing appropriate solutions or media, such as neutral salt buffers, tissue culture media, sucrose solutions, lysing buffers, solvents, fixatives and the like to trap cells exiting the chamber. The collected cells may be cultured for further analysis.

Methods of Operation

The following descriptions detail construction of an apparatus and methods of operation according to the present invention.

In one embodiment, an apparatus according to the present invention was constructed using two glass slides (1"–1.5", for example) as chamber walls. These walls may be spaced Teflon spacers; however other methods of separating chamber walls, such as glue, polymer gaskets, or mechanical precision clamps may be used, for example. The distance of separation between walls may be between about 0.1 microns and about 10,000 microns, and more preferably between about 10 microns and about 600 microns. In studies using the present apparatus, the distance of separation was 127 microns. One wall of the chamber supported a microelectrode array consisting of about 20 microns wide parallel electrode elements spaced about 20 microns apart. The electrode elements may run along the entire length of the chamber from the input port to the output port. It is understood that the length, width, thickness and spacing of electrode arrays may be altered to create electric fields of differing intensities and different inhomogeneity. It is also to be understood that an array of electrodes may be used with the present invention, or a single electrode element may be sufficient for certain applications, if combined with a ground plane. Further, it is to be understood that the electrode array may not be parallel, and other geometric configurations, such as interdigitated castellated electrodes, serially arranged electrodes, linear, polynomial, interleaved, three-dimensional and the like may be utilized.

In an exemplary embodiment, alternate electrode elements are connected to electrode buses along the two opposite long edges of the chamber wall. These electrode buses are connected to an electrical signal generator, which may be, for example, a function generator. Other suitable signal generators may include, for example, oscillators, pulse generators, digital output cards, klystrons, RF sources, masers, or the like. The electrode array may be fabricated using standard microlithography techniques, as are known in the art. For example, the electrode array may be fabricated by ion beam lithography, ion beam etching, laser ablation, printing, or electrodeposition. The electrode array of the exemplary embodiment described herein consisted of 100 nm gold over a seed layer of 10 nm chromium. It is understood that the present invention contemplates using electrical signals in the range of about 0 to about 50 V and about 0.1 kHz to about 180 MHz, and more preferably between about 10 kHz and about 10 MHz. In studies which are described below, the signals were provided by a HP 8116A function generator. The present invention may utilize a fluid flow of about 0.01 ml/min. to about 500 ml/min., and more preferably between about 1 ml/min and about 50 ml/min. In studies described below, fluid flow in the range of about 1–100 ml/min, was provided by a digital syringe pump.

Field Flow Fractionation

Cell mixtures in the studies discussed below consisted of blood cells (collected by venipuncture from healthy volunteers and diluted with 90 parts. $Ca^{2+}/Mg^{2+}$-free PBS containing 5 mM hemisodium EDTA) mixed in a ratio of 3:2 with HL-60 leukemia cells that had been cultured under standard conditions and harvested by centrifugation. Cell mixtures were washed twice in isotonic (8.5%) sucrose containing 3 mg/ml dextrose and resuspended at a final concentration of $2 \times 10^7$ malignant cells and $3 \times 10^7$ normal blood cells per ml in this same medium. The suspension conductivity was adjusted to 10 mS/m by addition of hemisodium EDTA to a final concentration of approximately 0.7 mM. It is contemplated by the present invention that other methods of obtaining and preparing samples are acceptable. Further, different ratios of the mixture may be used. For example, cell mixtures may be washed twice in an isotonic solution of 8.5% sucrose and 0.3% dextrose, resuspended at a final concentration of $1 \times 10^7$ malignant cells and $3 \times 10^7$ normal blood cells per ml in this same medium, and adjusted to a conductivity of 10 mS/m with a final concentration of ~0.7 mM hemisodium EDTA.

Figure 3:
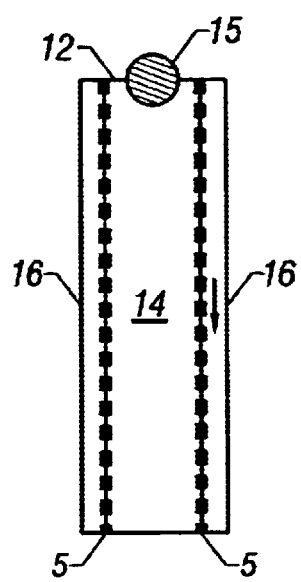
FIG. 3A is a graphical representation of the number of HL-60 cells exiting an apparatus according to the present invention under the influence of field flow fractionation, as a function of time (flow rate=200 ul/min).
FIG. 3B is a graphical representation of the number of HL-60 cells exiting an apparatus according to the present invention under the influence of field flow fractionation, as a function of time (flow rate=100 ul/min).
FIG. 3C is a graphical representation of the number of HL-60 and human-blood cells exiting an apparatus according to the present invention under the influence of field flow fractionation, as a function of time. The first and second peak corresponds to HL-60 cells and human blood cells, respectively. (flow rate=100 ul/min).
Figure 3A:
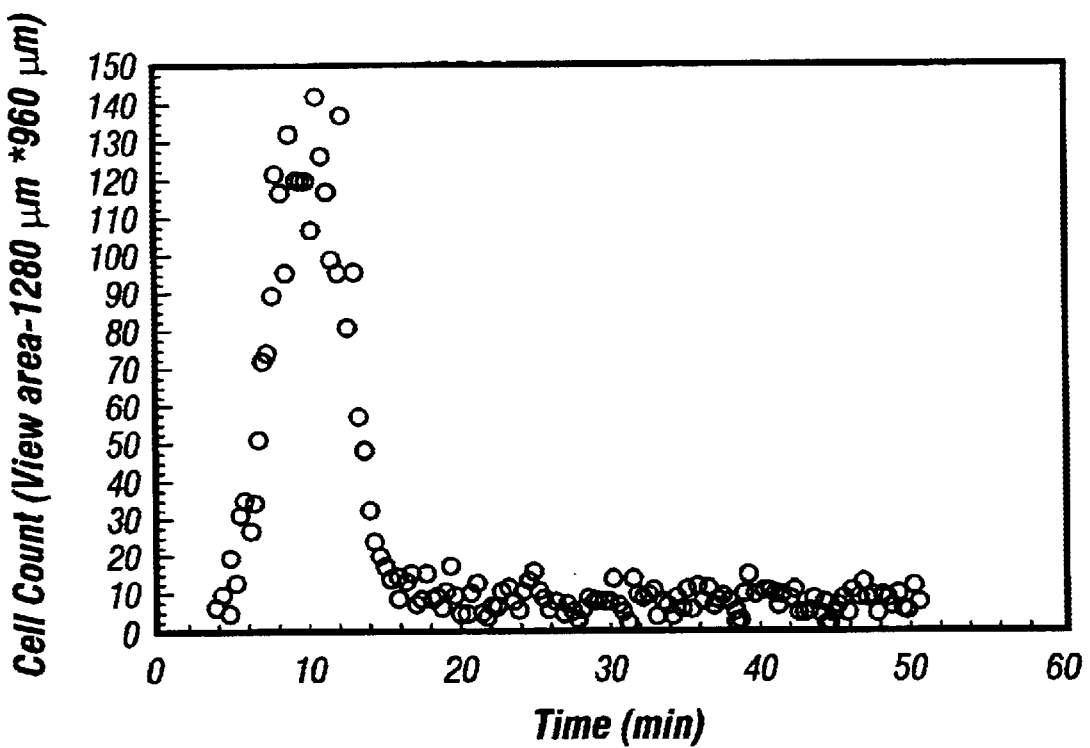
Figure 3B:
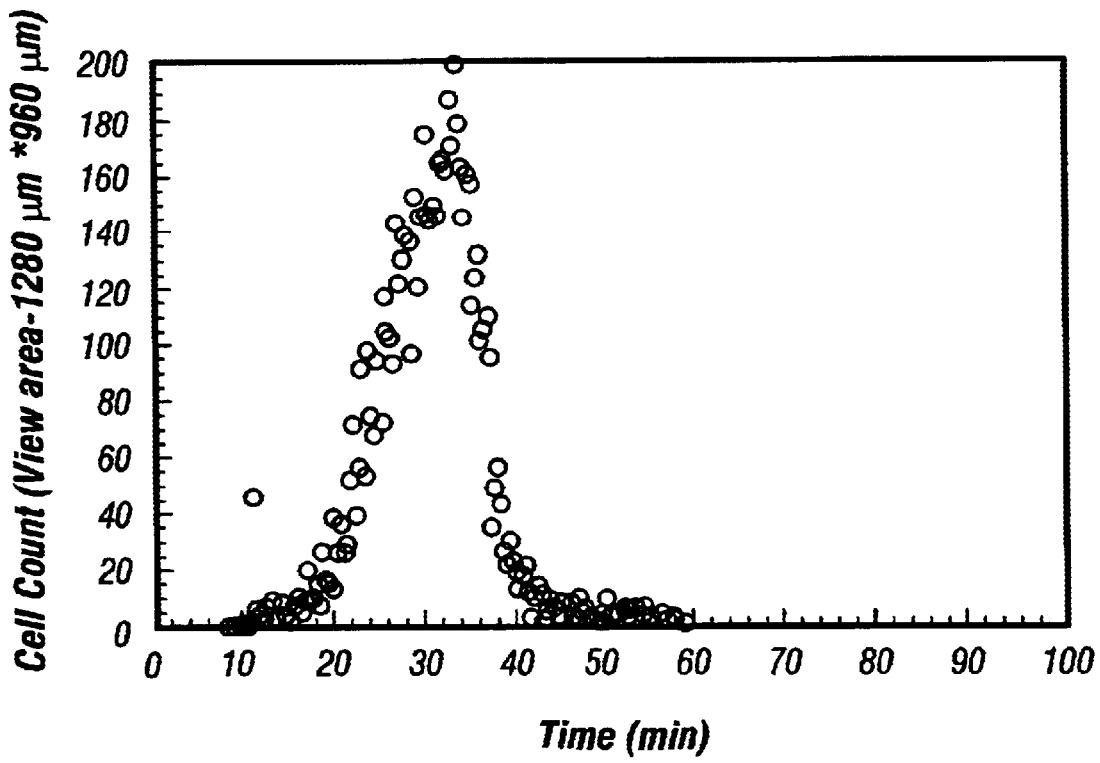

FIG. 3A shows the results of field flow fractionation on a sample of HL-60 cells (ATCC) cultured in a medium of RPMI 1640 10% FBS 22 mM HEPES in an apparatus as described above. The fractionation occurred at a flow rate of 200 ul/min. As shown in FIG. 3A, a sharp rise in HL-60 cells exiting the apparatus occurs at approximately 10 minutes after the flow of cells began. After this rise, the cell count rapidly tapers to a lower level which continues for approximately 50 minutes. FIG. 3B similarly shows the results of field flow fractionation of HL-60 cells at a flow rate of 100 ul/min. As shown in FIG. 3B, a sharp rise in HL-60 cells exiting the chamber occurs at approximately 30 minutes after the flow of cells began. Again, after this rise, the cell count rapidly tapers to a lower level which continues for approximately 30 minutes.

Figure 3C:
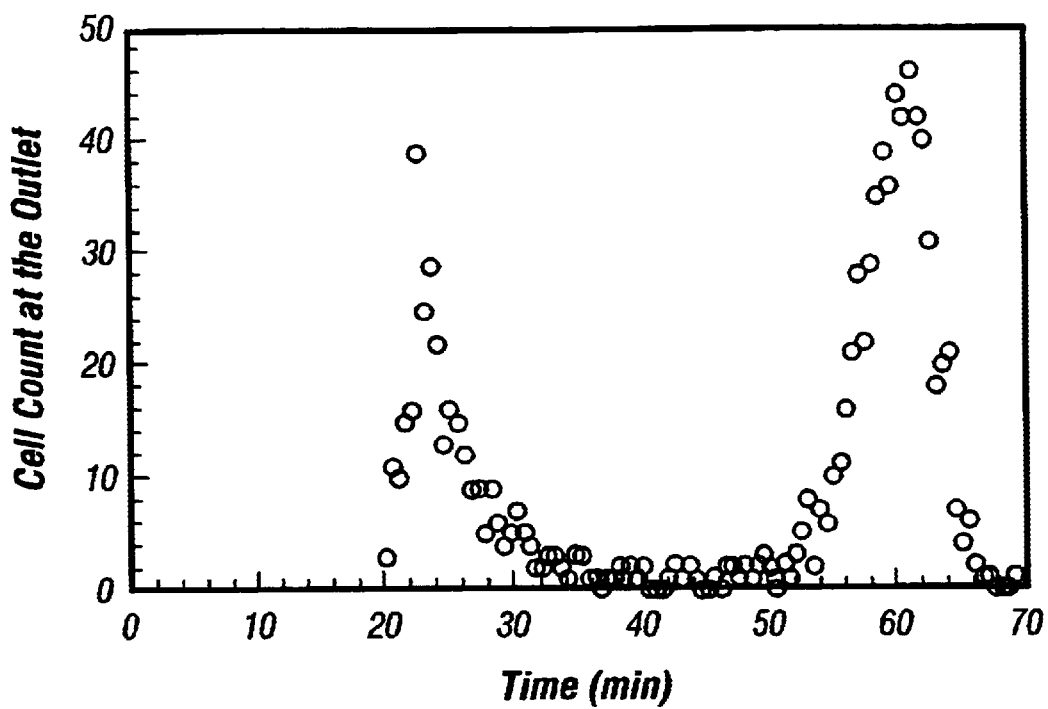

FIG. 3C shows the results of field flow fractionation on a mixture of HL-60 and human whole blood in a medium of 8.5% sucrose and 0.3% dextrose adjusted to a 10 mS/m conductivity, in an apparatus as described above. The fractionation occurred at a flow rate of 100 ml/min. As shown in FIG. 3C, a sharp rise in the HL-60 cells exiting the chamber occurred at approximately 20 minutes after the flow began. Thereafter, a second rise in the number of cells exiting occurred at approximately 60 minutes, which correlated to the exit of the human blood cells. However, it is noted that cells continue to exit before and after the peaks. Thus, separation by field flow fractionation is not capable of a complete separation. Therefore, FIGS. 3A, 3B, and 3C demonstrate that although field flow fractionation may discriminate and separate some particles of different characteristics, there is needed greater discrimination capabilities.

Three types of studies utilizing the apparatus of the present invention were performed that caused cDEP (conventional dielectrophoretic) forces on the particulate matter:

(1) Levitation of Cells Caused by cDEP Force

The levitation of DS-19 murine erythroleukemia cells (kindly supplied by M. Rifkind) supported in 8.5% sucrose+ 0.3% dextrose solution having a conductivity of 56 mS/m was investigated as a function of the frequency and voltage of signals applied to the electrode array in the absence of fluid flow. It is to be understood that various solutions having conductivities in the range of about 10 mS/m to about 2 S/m, such as tissue culture medium or the like, may be used. Further, it is possible to utilize a collection of cells only. Other solutions may be used so long as their electrical conductivity and osmolality are adjusted according to the particular application.

Figure 4A:
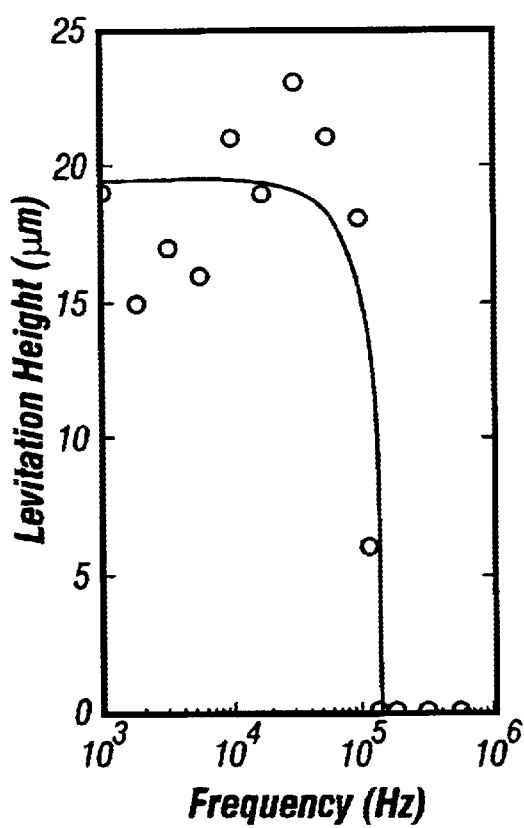
FIG. 4A is a graphical representation of DS19 cell levitation height under the influence of cDEP and gravitational forces as a function of frequency.
Figure 4B:
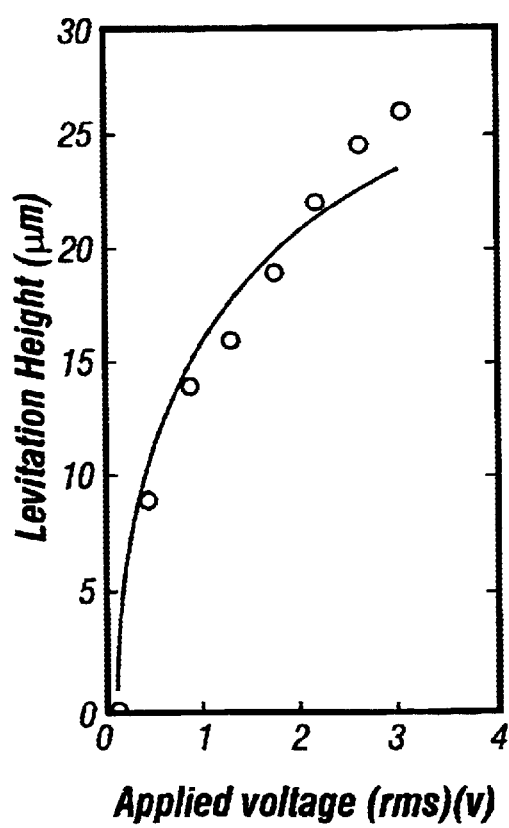
FIG. 4B is a graphical representation of DS 19 cell levitation height under the influence of cDEP and gravitational forces as a function of voltage.

The results of this study are shown in FIG. 4A and FIG. 4B. In the frequency range 1 kHz–40 kHz, DS 19 cells were levitated to about 20 microns at an applied voltage of 4V peak to peak (p-p), as shown in FIG. 4A. Above 40 kHz, the levitation height dropped rapidly, and when the frequency reached 140 kHz and above, cells were no longer levitated but were instead attracted to electrode edges by positive cDEP.

At an applied frequency of 50 kHz, levitation of DS19 cells occurred when the applied voltage was above about 0.5 V p-p, as shown in FIG. 4B. Above this threshold, the cells levitated and the height of levitation increased with increasing voltage. This behavior was consistent with that predicted by cDEP theory, the dielectric properties of the cells as measured using the technique of electrorotation, and the density of the cells and their supporting medium.

(2) cDEP/FFF studies

Figure 5A:
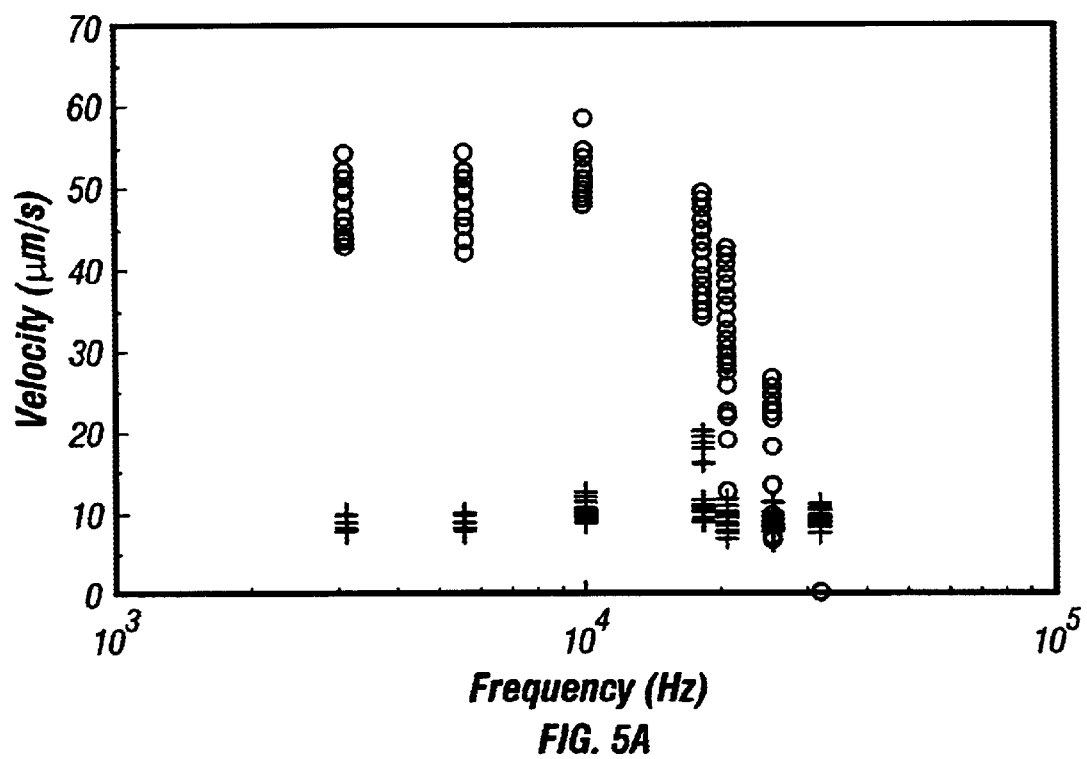
FIG. 5A is a graphical representation of velocity of HL-60 cells travelling through a cDEP-FFF apparatus according to the present invention as a function of frequency. (flow rate=10 ul/min).

A second study using the apparatus discussed above involved the velocity of HL-60 human promyelocytic leukemia cells supported in 8.5% sucrose+0.3% dextrose solution having a conductivity of about 10 mS/m with an established fluid flow in the chamber, as a function of the frequency of the voltage signals applied to the electrode array. When no voltage signal was applied, the cell velocity was about 10 microns per second as they were transported under the influence of an applied fluid flow rate of 10 ul/min (FIG. 5A). The fluid flow may be either the solution including the cells to be tested, or it may be another fluid, or the same fluid without the cells. Additionally the solution may be ramped over time to alter, for example, the pH, or conductivity of the solution.

Addressing the electrodes with voltage signals affected the height at which the cells traveled above the chamber bottom wall and thereby altered their position and velocity in the laminar flow. As shown in FIG. 5A, below 10 kHz, cell velocity increased to about 50 microns per second with an applied voltage of 3 V p-p. As the frequency was increased in the range of about 10 kHz to about 25 kHz, the cell velocity gradually fell as the levitation height was reduced. Above 30 kHz, these cells were attracted to the electrode and thus they ceased moving. This response with increasing frequency agreed with the behavior expected from the measured electrical properties of the cells.

Figure 5B:
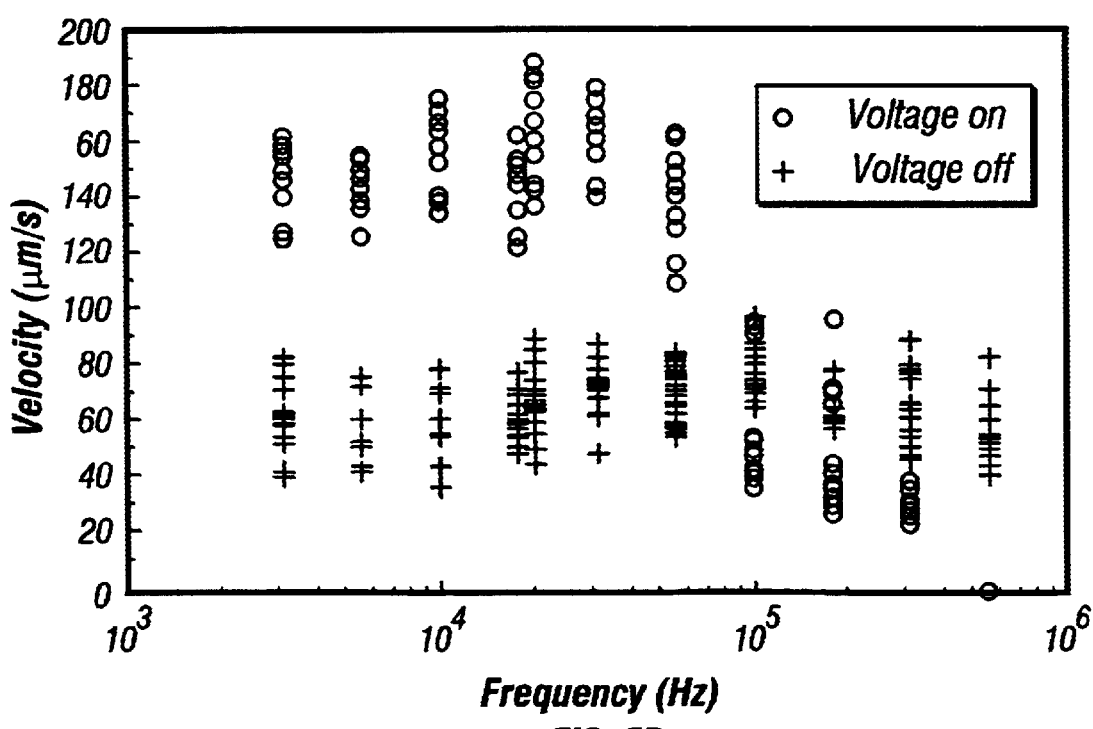
FIG. 5B is a graphical representation of velocity of MDA 468 cells travelling through a cDEP-FFF apparatus according to the present invention as a function of frequency. (flow rate=40 ul/min).
Figure 5C:
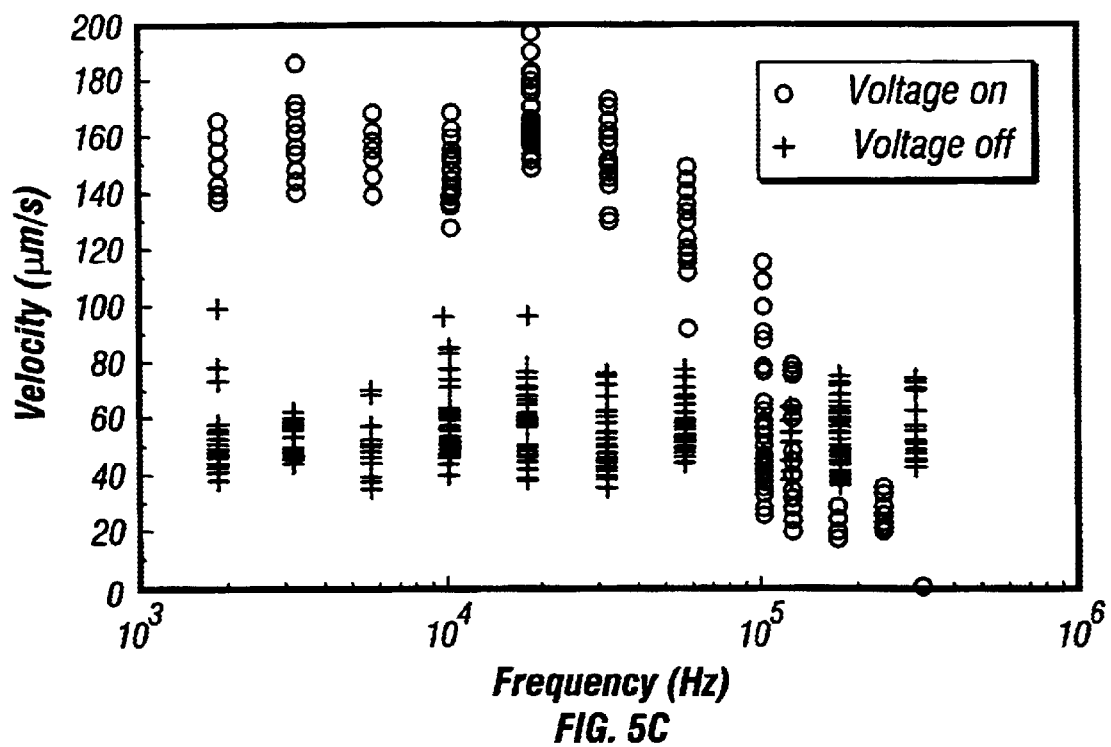
FIG. 5C is a graphical representation of velocity of MDA 435 cells travelling through a cDEP-FFF apparatus according to the present invention as a function of frequency. (flow rate=40 ul/min).
Figure 5D:
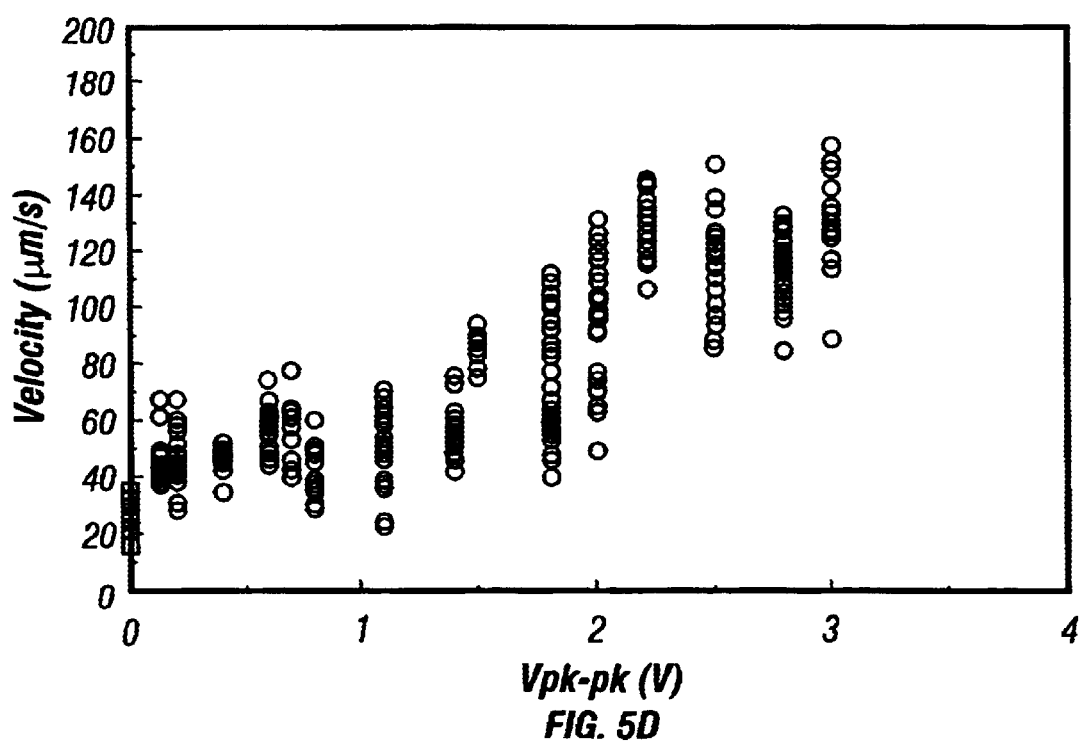
FIG. 5D is a graphical representation of velocity of MDA 435 cells travelling through a cDEP-FFF apparatus according to the present invention as a function of voltage. (flow rate=40 ul/min).

As shown in FIGS. 5B and 5C, similar results were obtained for studies using other cells having different cell properties. Specifically, FIG. 5B shows the results for MDA 468 cells (kindly supplied by Janet Price) in a solution of 8.5% sucrose 0.3% dextrose conductivity at 10 ms/m at a flow rate of 40 ul/min at 3 V p-p. FIG. 5C shows the results for MDA-435 cells (kindly supplied by Janet Price) in the same solution at a flow rate of 40 ul/min at 3 V p-p. FIG. 5D shows the results for MDA-435 cells at a flow rate of 40 ul/min at a frequency of 31.6 kHz. As noted in FIG. 5D, the velocity of cells increases approximately linearly with voltage.

(3) cDEP/FFF on Mixture of HL-60 and Human Blood Cells

The chambers of the apparatus were preloaded with a mixture of HL-60 and human blood cells in the ratio 1:10 at a total concentration of $5 \times 10^7$ cells/ml. The cells were supported in 8.5% sucrose+0.3% dextrose solution having a conductivity of 10 mS/m. A voltage of 3 V p-p at 40 kHz was applied to the electrodes and fluid flow at the rate of 10 ul/min was started. All of the HL-60 cells were trapped at the edges of the electrode elements, while the human blood cells (mainly erythrocytes) were levitated and were transported by the fluid. By adjusting the frequency in the range of 8–15 kHz, HL-60 cells were also released and their rate of transport controlled relative to the erythrocytes. When HL-60 cells were levitated to heights above or below the erythrocytes, they moved correspondingly more quickly or more slowly than these blood cells depending on their position in the field flow.

The following is an additional study performed according to the present invention. Fluids were injected and removed through slots at each end of the chamber. The outlet port was furnished with a well to trap cells exiting the chamber. Prior to performing studies, the chamber was soaked for 5 minutes with 20% (w/v) bovine serum albumin solution to render the glass surfaces less adherent to cells. Alternately the glass surfaces may be air blown, or washed and treated with silane. Dielectrophoretic forces were generated by connecting alternate electrodes to sinusoidal voltages of fixed or swept frequencies, and were monitored using an oscilloscope. Forces to remove cells from the separation chamber were provided by laminar flow of an eluate buffer, controlled by two digital syringe pumps connected in push-pull configuration between the inlet and outlet ports of the chamber. A bubble-free path of fluid was maintained between the pumps at all-times.

Following injection of approximately 30 ul of the cell mixture (about $1.2 \times 10^6$ cells) to half fill the chamber, a 200 kHz signal of 5 V peak-peak was applied to the electrode array for 30 sec to collect all cells by positive DEP at the high-field regions of the electrode tips. It is not required, however, to only half-fill the chamber, and a larger chamber may allow for better discrimination. Flow of eluate (consisting of cell-free suspension buffer, which may also be a mixture of 8.5% sucrose plus 3 mg/ml dextrose having a conductivity of 10 mS/m), was then started at 5 ml/min. This flow may be accomplished under the control of two digital syringe pumps operating in a push-pull configuration between the inlet and outlet ports of the chamber. Alternately, the flow may be controlled by a peristaltic pump, gravity flow, blood pressure, or the like. The frequency of the applied electric signal was lowered until the tumor cells were selectively retained while the blood cells were eluted and trapped in the collection well. After 20 minutes, cells were removed from the well by cross-flow between two additional syringe ports without disturbing the tumor cells still on the electrodes. The voltage was then turned off to release the cells held by DEP and these were eluted and collected separately.

EXAMPLE 3

Separation of Polystyrene Microbeads Using Dielectrophoretic Field-Flow-Fractionation The characterization of a dielectrophoretic/gravitational-field-flow-fractionation (DEP/G-FFF) system using model polystyrene (PS) microbeads has been achieved. Separations of PS beads of different surface functionalization (COOH and none) and different sizes (6, 10 and 15 $\mu$m in diameter) have been demonstrated. To investigate the factors influencing separation performance, particle elution times were determined as a function of particle suspension conductivity, fluid flow rate, and applied field frequency and voltage. Experimental data were analyzed using a theoretical model (Huang et al., 1997) and good agreement between theory and experiment was found. It was shown that separation of PS beads was based on the differences in their effective dielectric properties. Particles possessing different dielectric properties were positioned at different heights in a fluid-flow profile in a thin chamber by the balance of DEP and gravitational forces, were transported at different velocities under the influence of the fluid flow, and were separated. To explore hydrodynamic (HD) lift effects, velocities of PS beads were determined as a function of fluid flow rate in the separation chamber when no DEP field was applied. In this case, particle equilibrium height positions were governed solely by the balance of HD lift and gravitational forces. It was concluded that under the experimental conditions reported in this example that the DEP and gravitational forces were the dominant factors in controlling particle equilibrium height and that HD lift force played little role in DEP/G-FFF operation.

DEP-FFF technique reported in this Example exploits the balance between dielectrophoretic and gravitational (sedimentational) forces. In this method negative DEP forces are produced by microelectrodes on a chamber and levitate particles to equilibrium positions in a flow-velocity profile. Particles at different heights in the flow stream move at different velocities and can be fractionated based upon their different retention times in the chamber. We term this technique dielectrophoretic/gravitational-Field-flow-fractionation (DEP/G-FFF), a subtechnique of DEP-FFF. Balancing DEP forces with other types of physical forces (e.g. electrophoretic, crossflow or DEP forces generated from different electrodes in the chamber) results in other subtechniques such as DEP/electrophoretic-FFF.

The construction and characterization of a complete DEP/G-FFF system consisting of a syringe pump, a fluid-sample-injector, a DEP/G-FFF chamber and a particle detector at the chamber outlet has been achieved. The separations of model particles of polystyrene (PS) microbeads having different surface-functionalizations (COOH and none) and different sizes (6, 10 and 15 $\mu$m in diameter) have been demonstrated. Separation performance has been shown to be a function of the suspension conductivity, the fluid flow rate, and the voltage and frequency of the signals applied to the electrode. A theoretical analysis of the results has revealed that separation of PS microbeads is based upon the differences in the effective dielectric properties of different bead types.

METHODS AND MATERIALS

DEP/G-FFF system.

Figure 13:
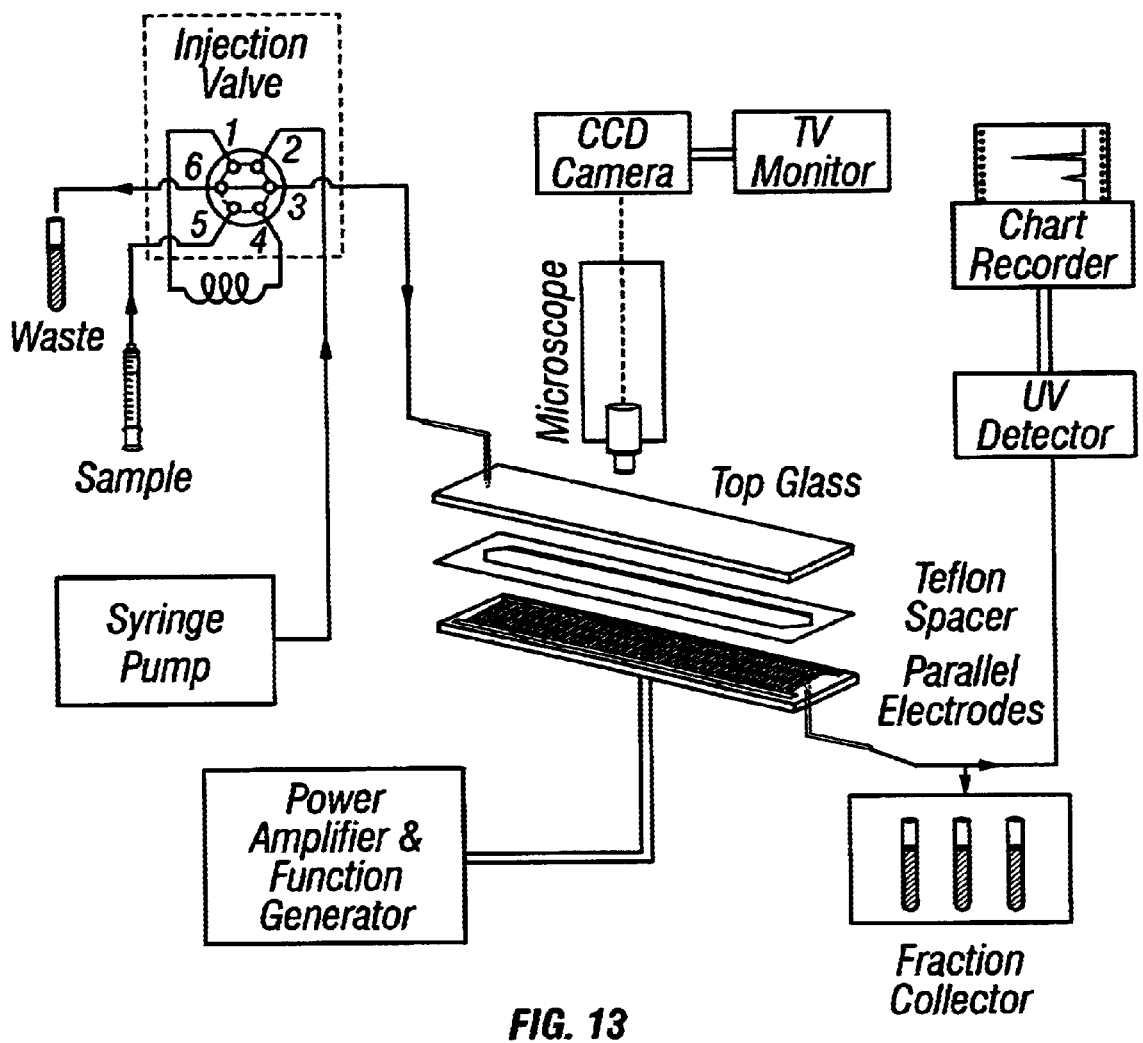
FIG. 13 is a schematic representation of a DEP/G-FFF system showing a chamber in exploded view. The microfabricated, interdigitated electrode array on the bottom surface of the chamber may be energized with voltage signals from the power amplifier to generate DEP levitation forces. Cell mixtures may be introduced into the chamber via the injection valve. The syringe pump may be operated to establish a fluid-flow profile in the chamber. Cell kinetic responses may be monitored through video microscopy. Cells exiting the chamber may be detected by a UV detector or collected by a fraction collector.

A schematic representation of the DEP/G-FFF system used in this example is shown in FIG. 13. FIG. 13 reveals a Teflon spacer with a flow-channel cut into it. The operation of the injection valve is as follows: the sample is first loaded into the loop through the path "syringe→5→4→loop→1→6→waste" with fluid flow in the second path; in the injection mode, the fluid flow path is "syringe pump→2→1→loop→4→3→chamber". Parallel microelectrode arrays having 50 $\mu$m widths and gaps were fabricated on 50×50 mm glass substrates using standard photolithographic methods. Eight 50×50 mm electrode plates were glued end-to-end onto a supporting glass plate to form an electrode of area 50×400 mm. A Teflon spacer (H 0.4×W 50×L 400 mm) was cut to provide an open channel with dimensions of 388 mm from tip to tip and 25 mm in width except at the tapered ends. This was sandwiched between the bottom electrode plate and a top glass plate to form the DEP/G-FFF chamber. The chamber was firmly assembled with 36 Nylon screw-clamps (Bel-Art Products, NJ). The top and bottom plates were drilled with 0.0625 in.-diameter holes to fit inlet and outlet tubing at positions coincident with the points of the tapered opposite ends of the cutout channel. Microelectrode arrays, each having two 4-mm wide electrical conductor buses running along the edges, were connected in parallel to a lab-built PA05-based power amplifier (Apex Microtechnology, AZ). The amplifier could deliver up to 10 W of power into a 2-ohm load with a bandwidth of DC to 400 kHz.

A digital syringe pump (KD Scientific, MA) was used to provide continuous flow of carrier medium through the DEP/G-FFF chamber at a rate selectable between 1 $\mu$l/min and 70 ml/min. A sample injection valve (Rheodyne Model 7010, CA) allowed measured sample introduction from a 10-$\mu$l loop. A 5 cm length of PEEK tubing (0.0625 in. O.D., 0.010 in I.D.) having a void volume of 2.5 $\mu$l served as the inlet connection between the injection valve and the chamber.

Two different methods were employed to characterize particle responses in the DEP/G-FFF chamber. The first approach was to manually gauge the dynamics of particle separation by counting particles that passed by several specific inspection locations along the length of the chamber as a function of time with the aid of video microscopy. The second method was to monitor particles exiting the chamber with an UV detector. To accomplish this, the chamber outlet was connected to the 3 $\mu$l flow cell of an UV spectroscopic detection system (ISCO Model UA-6, NE) via a 5 cm length of PEEK tubing (0.0625 in. O.D., 0.020 in I.D.). The detector was operated at a wavelength of 254 nm and its output voltage signal, proportional to light attenuation by particles in the flow-cell, was fed to a chart recorder (Goetz, Austria).

Polystyrene (PS) Bead Preparation

Two types of experiments were conducted: (1) separation of PS beads (Polysciences, PA) of similar density (1050 kg/m$^3$) and size (9.44±0.95 vs 10.57±1.03 $\mu$m in diameter) but possessing different surface functionalizations (COOH and none); and (2) separation of non-functionalized PS (NF—PS) beads of similar density (1050 kg/m$^3$) but of different sizes (6.14±0.45, 10.57±1.03 and 15.5±1.84 $\mu$m). Surface-carboxylated (COOH—PS) beads were characterized by the manufacturer as having a surface charge of 0.12 meq (COO$^-$)/g of polymer. While there are other methods suitable for the separation of PS beads, these belads were chosen as model particles in this Example to aid in the characterization and development of the DEP/G-FFF system because they were relatively homogeneous in terms of size, density and other structural and compositional characteristics.

A DEP buffer, consisting of 8.5% (w/v) sucrose and 0.3% (w/v) dextrose, was used as the FFF carrier fluid and particle-suspending medium. Electrical conductivity of the buffer was brought to 2.2 or 10 mS/m with aliquots of 300 mM EDTA (adjusted to pH 7.0 with NaOH). The final pH of the buffer was found to be ~6.8. To ensure that no air bubbles were present in the DEP/G-FFF chamber during separation, the sucrose/dextrose buffer was degassed under vacuum for several minutes. Sample mixtures were prepared by diluting aliquots of Polysciences-supplied microbead suspensions with the sucrose/dextrose buffer to achieve particle concentrations of 1.5×10$^7$, 3×10$^6$ and 4×10$^5$ particles per ml for PS beads of nominal diameter 6, 10 and 15 $\mu$m, respectively.

Bead Separation Protocol

The DEP/G-FFF chamber was first loaded with carrier medium (sucrose/dextrose buffer) using the syringe pump; precautions were taken to ensure that no air bubbles were introduced into the chamber. Appropriate voltage signals (between 0.5 and 1 V RMS at 50 kHz) were then applied to the microelectrodes so that PS beads would be levitated to equilibrium positions upon injection into the chamber, thereby minimizing contact and possible adherence of the beads to the electrode surface. Next, a mixture of PS bead types was introduced into the chamber. To accomplish this, the injection valve was first set in the "load" mode and the 10 $\mu$l loop was filled with sample using a manually operated syringe. The valve was then switched to the "injection" mode and 35 $\mu$l sucrose/dextrose buffer was pumped through the loop by the syringe pump operating at 50 $\mu$l/min to flush the beads into the DEP/G-FFF chamber. The valve was then switched back to the "load" mode, ready for the next sample loading.

After PS microbeads had been loaded into the inlet port of the chamber, they were allowed to relax for some minutes (up to 30 min.) in order to attain equilibrium height positions where the sedimentation and DEP levitation forces were balanced. Following relaxation, flow of the carrier medium was initiated in the chamber from the syringe pump which was operated at a desired flow rate in the range 20–2000 $\mu$l/min. As PS beads were carried along the chamber length, their kinetics were observed with video microscopy (Nikon Microphot-SA microscope, Hamamatsu XC-77 CCD camera) and results were recorded on a VCR (Panasonic: AG-7350). Finally, PS beads exiting the chamber were monitored by the UV detection system.

Results

Separation Dynamics

Figure 14:
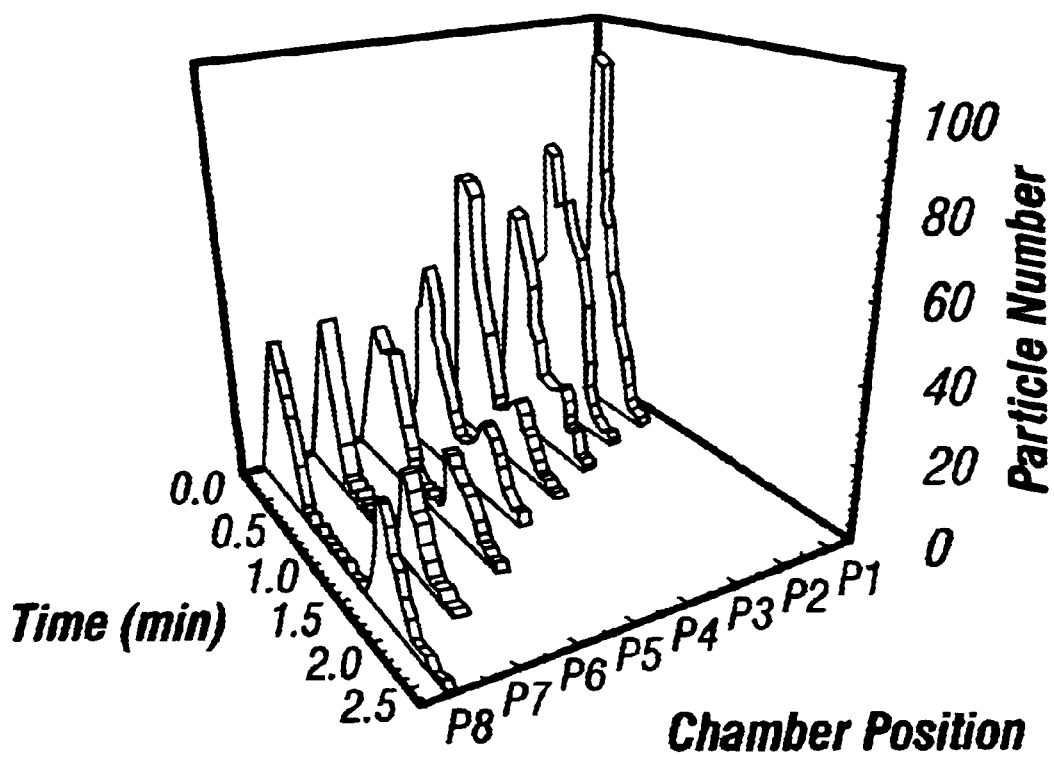
FIG. 14 is a three-dimensional representation of DEP/G-FFF fractionation of NF—PS (10.57±1.03 $\mu$m) and COOH—PS (9.44±0.95 $\mu$m) beads. Particle counts were plotted as a function of time at eight inspection locations having distances of 36, 64, 92, 132, 165, 225, 272, 360 mm from the chamber inlet. To show the progress of separation, the time after the emergence of the first bead at each position was used to define zero time for that location.

To examine the dynamic process of DEP/G-FFF separation, particle trajectories in the chamber were followed by monitoring the number of particles that passed by several inspection windows along the chamber as a function of time. From these data, we constructed three-dimensional representations were constructed of separation dynamics where the number (Z-axis) of particles was plotted as a function of time (X-axis) at different inspection positions (Y-axis) along the chamber. A typical example is shown in FIG. 14 for a DEP/G-FFF separation of NF—PS and COOH—PS beads. Conditions for FIG. 14 include: Voltage—1.6 V RMS at 50 kHz; parallel electrode arrays—50 $\mu$m electrode widths and gaps. After injection, beads were allowed to relax to their equilibrium height positions in the chamber for 10 minutes prior to the application of the fluid flow. To begin separation, flow of sucrose buffer of electrical conductivity 10 mS/m was initiated at 200 $\mu$l/min. Clearly, the two subpopulations of beads traveled at different velocities and became more and more separated as they moved further along the chamber. A single peak was only visible at Position #1. Thereafter bifurcation of the peak occurred until two distinct (non-overlapping) peaks were observed at Position #5 (165 mm from the chamber inlet). This indicates that complete separation of the two bead subpopulations may be achieved with a chamber only 165 mm long. By the time the beads reached Position #8 (close to the chamber outlet and 360 mm from the inlet), the two subpopulation peaks were separated by a time interval of >1 min.

DEP/G-FFF Fractograms

Figure 15A:
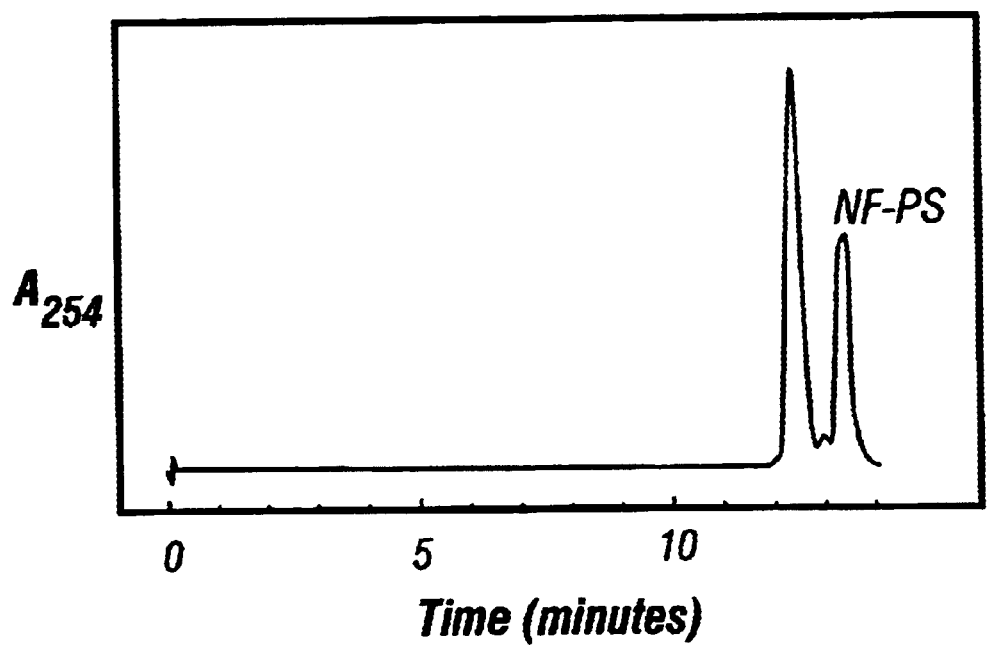
FIG. 15A is a DEP/G-FFF Fractogram showing the separation of NF—PS (10.57±1.03 $\mu$m, the second peak) and COOH—PS (9.44±0.95 $\mu$m, the first peak) beads.
Figure 15B:
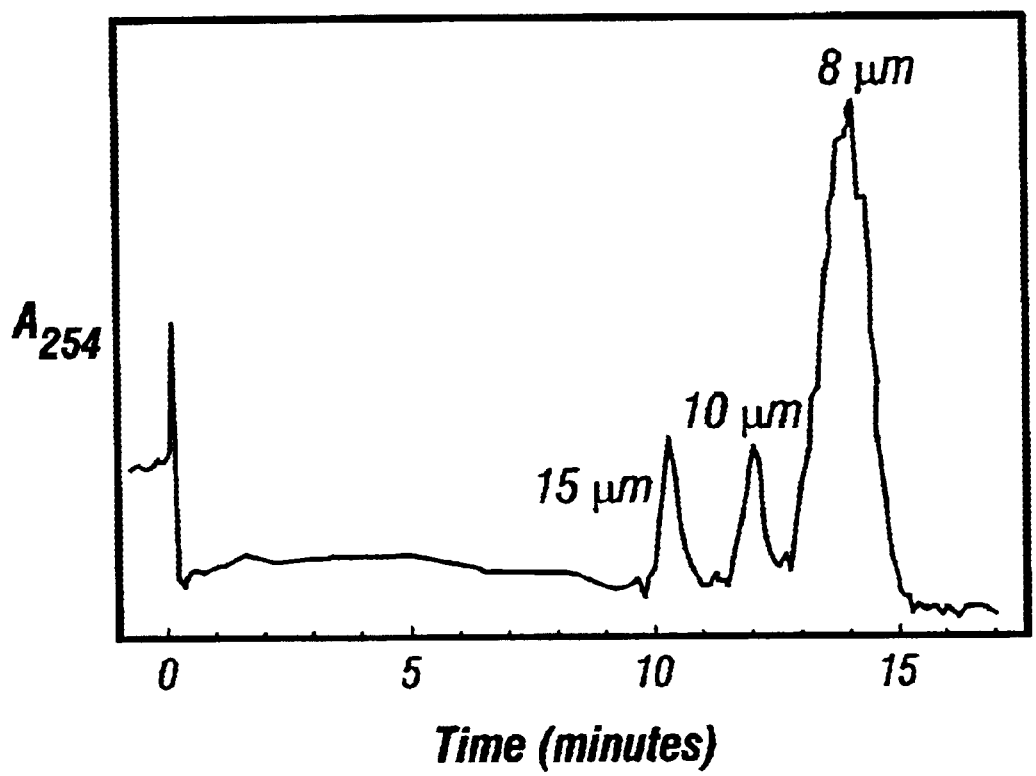
FIG. 15B is a DEP/G-FFF Fractogram showing the separation of NF—PS beads of different sizes (6.14±0.45, 10.57±1.03 and 15.5±1.84 $\mu$m in diameter).

To characterize the separation performance, particles exiting the DEP/G-FFF chamber were monitored using the UV detector. Typical fractograms displaying the time dependence of the UV absorbance are shown in FIGS. 15A and 15B. FIG. 15A depicts the separation of COOH—PS and NF—PS beads with the two peaks occurring 11.7–12.4 and 12.8–13.4 minutes after the initiation of fluid flow, respectively. Conditions for FIG. 15A include: Voltage—1.24 V RMS at 50 kHz; parallel electrode arrays—50 $\mu$m electrode widths and gaps. Beads were allowed to relax to their equilibrium height positions in the chamber for 10 minutes after injection and prior to the application of fluid flow. Sucrose buffer of electrical conductivity 10 mS/m was pumped through the chamber at 800 μl/min. In order to associate elution times with specific microbead types, DEP/G-FFF experiments were performed on pure NF—PS or COOH—PS beads and then on several mixtures of these bead types at different concentration ratios. By comparing the elution peak times in these experiments, it has been determined that the COOH—PS beads eluted ahead of the NF—PS beads. FIG. 15B shows the separation of NF—PS beads of three different sizes (nominal diameters 6, 10 and 15 μm). Conditions for FIG. 15B include: Voltage—0.53 V RMS at 100 kHz; parallel electrode arrays—50 μm electrode widths and gaps. Beads were allowed to relax for 25 minutes after injection and prior to the application of fluid flow. Sucrose buffer of electrical conductivity 2.2 mS/m was pumped through the chamber at 800 μl/min. Direct observation of particle motion under the microscope revealed that larger beads moved faster than smaller ones. Thus, the three elution peaks in time range of 9.9–10.8, 11.6–12.4 and 12.7–15 minutes corresponded to populations of 15, 10 and 6 μm diameters, respectively.

Separation of PS and COOH—PS Beads

Figure 16A:
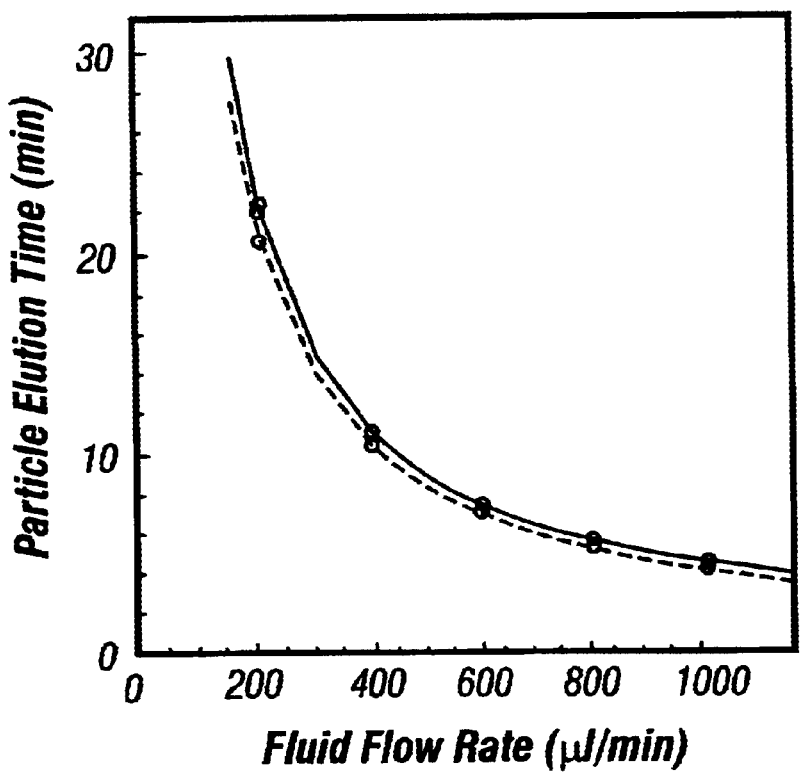
FIGS. 16A–16B (A) Dependency of elution peak times for NF—PS (10.57±1.03 $\mu$m, solid curve) and COOH—PS (9.44±0.95 $\mu$m, broken curve) beads on the fluid flow rate in a DEP/G-FFF separation. (B) Plot of elution peak times for NF—PS (upper line) and COOH—PS (lower line) beads versus the reciprocal of the fluid flow rate. The solid line is a linear fit to the experimental data.
Figure 16B:
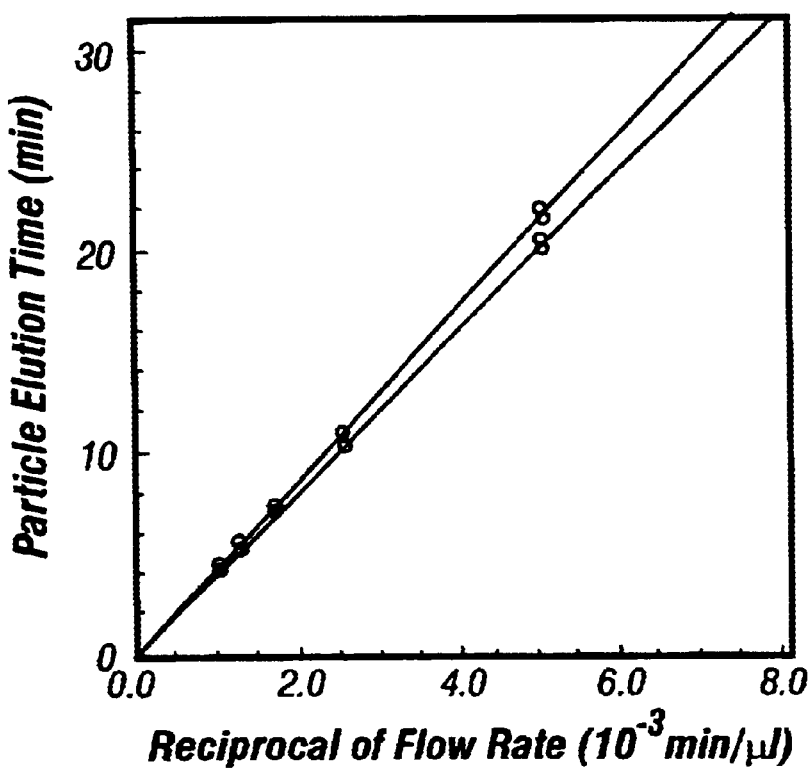

We (Huang et al., 1997) and others (Williams et al., 1992) have previously reported that particles experience a hydrodynamic (HD) lifting force that pushes them away from the chamber walls as they are carried along in a fluid flow profile. This lifting force was shown to increase with the fluid flow rate (Williams et al., 1992). To determine the influence of the HD lifting force on overall particle kinetics, separation experiments were conducted as a function of the fluid flow rate for a specified DEP field condition. As shown in FIGS. 16A and 16B, the elution peak times for NF—PS and COOH—PS beads were inversely proportional to the flow rate in the range of 100 to 1000 μl/min. Separation effectiveness, as characterized by the ratio of the elution peak times for two PS bead populations, was not compromised even at the high flow rate of 1000 μl/min. These results indicate that the hydrodynamic lifting force for played little role in the separation process for the flow rate range investigated here.

Figure 17A:
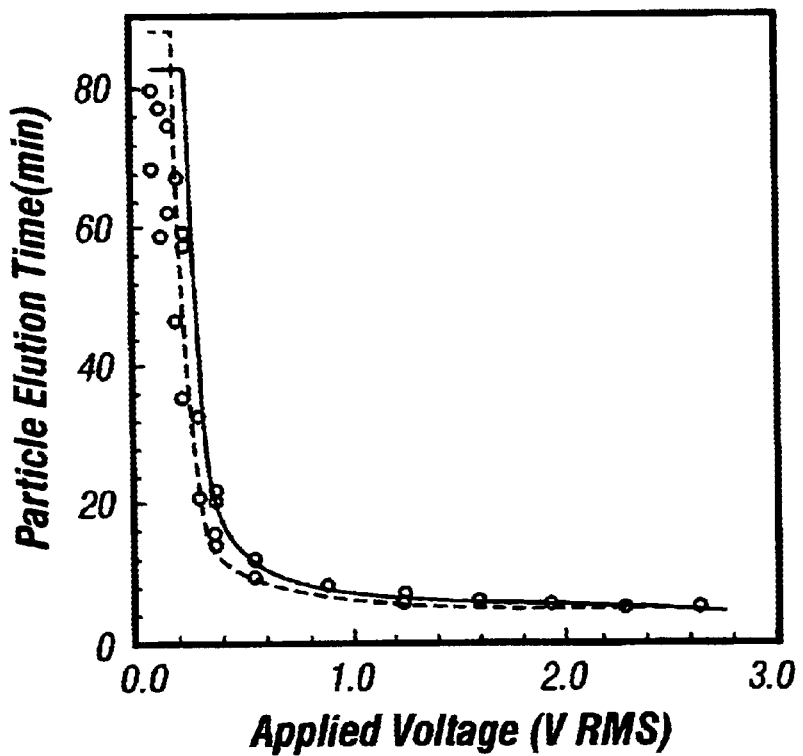
FIGS. 17A–17B (A) Dependency of elution peak times for NF—PS (10.57±1.03 $\mu$m, solid curve) and COOH—PS (9.44±0.95 $\mu$m, broken curve) beads on the voltage (50 kHz) applied to the microelectrodes. (B) Plot of the ratio of the two elution-peak times for NF—PS and COOH—PS beads versus the applied voltage. Particles were allowed to relax in the chamber for 10 minutes after injection and prior to the application of fluid flow. Sucrose buffer of electrical conductivity 10 mS/m was pumped through the chamber at a rate of 800 $\mu$l/min.
Figure 17B:
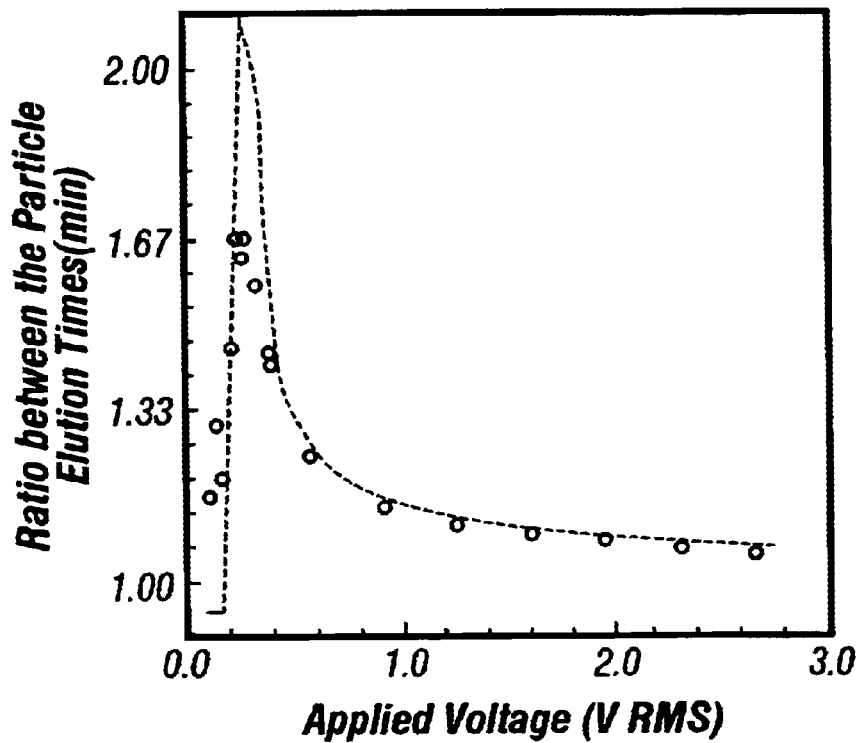

The importance of DEP forces in DEP/G-FFF separation is illustrated in FIG. 17A where elution peak times for NF—PS and COOH—PS beads are shown as a function of the applied DEP voltage signals. Increasing the applied voltage from 0.07 V to 2.65 V RMS resulted in faster elution of both NF—PS and COOH—PS beads. This is expected when it is considered that larger.applied voltages levitate particles to higher equilibrium position the flow velocity profile (Gascoyne et al., 1996; Huang et al., 1997). Separation effectiveness was observed to be a function of the applied voltage (FIG. 17B). The best separation of the two bead populations, as characterized by a maximum value of ~1.65 for the ratio of the two elution peak times, was attained at an applied voltage of 0.21 V RMS. Increasing or decreasing the applied voltage resulted in a gradual convergence of the two elution-peaks.

Separation of NF—PS beads of three different sizes

Figure 18:
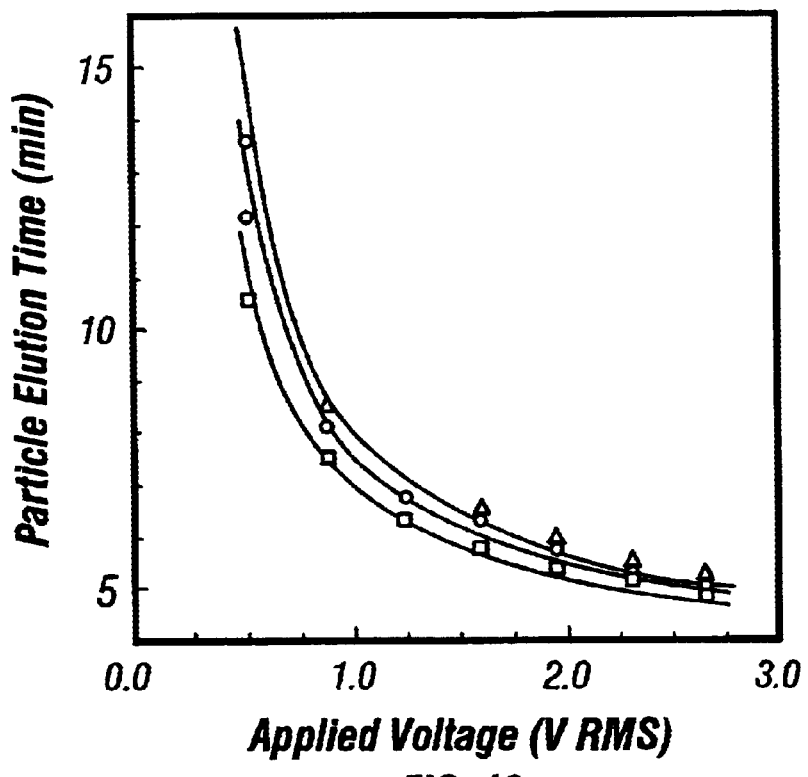
FIG. 18 Dependency of elution peak times for NF—PS beads of 6 (triangle), 10 (circle) and 15 (square) $\mu$m diameter on the voltage (50 kHz) applied to the microelectrode array. Particles were allowed to relax to equilibrium height positions in the chamber for 25 minutes after injection and prior to the application of fluid flow. Sucrose buffer of electrical conductivity 2.2 mS/m was pumped through the chamber at a rate of 800 $\mu$l/min.
Figure 19:
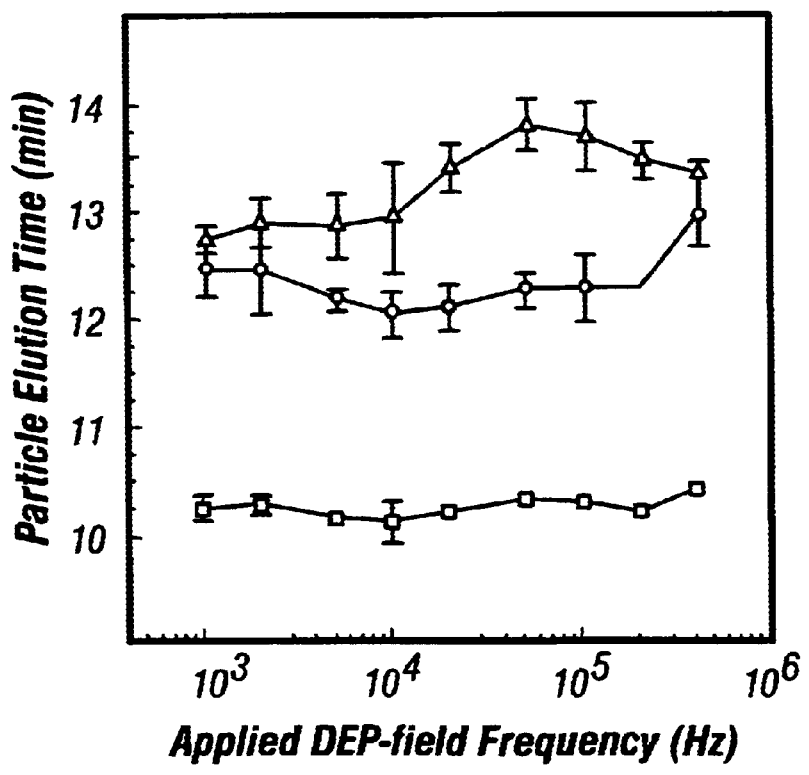
FIG. 19 Dependency of elution peak times for PS beads of 6 (triangle), 10 (circle) and 15 (square) $\mu$m diameter on the applied field frequency. The voltage of the applied electrical signals was 0.53 V RMS. Particles were allowed to relax to their equilibrium height positions in the chamber for 25 minutes prior to the application of fluid flow. Sucrose buffer of electrical conductivity 2.2 mS/m was pumped through the chamber at a rate of 800 $\mu$l/min.

The dependence of elution times on the applied DEP voltage is shown in FIG. 18 for PS beads of nominal diameter 6, 10 and 15 μm. As for the separation of NF—PS and COOH—PS beads, an increase in the applied voltage resulted in decreased bead elution times and decreased separation between the three elution-peaks. Separation of NF—PS beads of 6, 10 and 15 μm was also studied as a function of the applied field frequency for constant fluid flow and applied voltage conditions (FIG. 19). The elution-peak time for 15 μm beads remained nearly constant in the frequency range 1 to 400 kHz. For 10 μm beads, the elution time was nearly constant in the frequency range 5 to 200 kHz but became larger at lower (1–2 kHz) or higher (400 kHz) frequencies. 6 μm beads exhibited a strong frequency dependency with a maximum elution time at 50 kHz. Optimum separation of these beads was achieved for this example at ~50 kHz.

Bead Relaxation

A common feature for most FFF operations (Liu et al., 1991) is the relaxation process in which particles to be separated are allowed to relax to their equilibrium positions with respect to the two major surfaces of the separation chamber before the fluid-flow is applied. The equilibrium positions are determined by the balance of physical forces acting on the particles. The relaxation process ensures that the differential positions of the particles in the fluid-flow profile and the corresponding particle velocities and transit times across the chamber depend only on the physical properties of the particles, not on their initial positions after introduction into the chamber. Therefore, PS beads were allowed to sediment to their equilibrium heights with appropriate DEP electrical fields applied after they were introduced into the DEP/G-FFF chamber. The time ($t_r$) required for a particle of radius r and density pp to sediment a distance H can be readily derived from the formula $$t_r = \frac{9H\eta}{2(\rho_p - \rho_m)r^2 g} \tag{16}$$

where g is the acceleration due to gravity, $\rho_m$ and η are the density and viscosity of the suspending medium, respectively. Equation 16 reveals that small particles take longer to relax than larger particles. For example, the relaxation times for PS beads of 6, 10 and 15 μm diameter (density 1.05 g/cm³) are about 4, 9 and 25 minutes, respectively, for a relaxation distance of 400 μm in a medium of density 1.033 g/cm³ and viscosity 1.26'10⁻³ kg/(m·s).

DEP/G-FFF Chamber Surface Treatment

Figure 20:
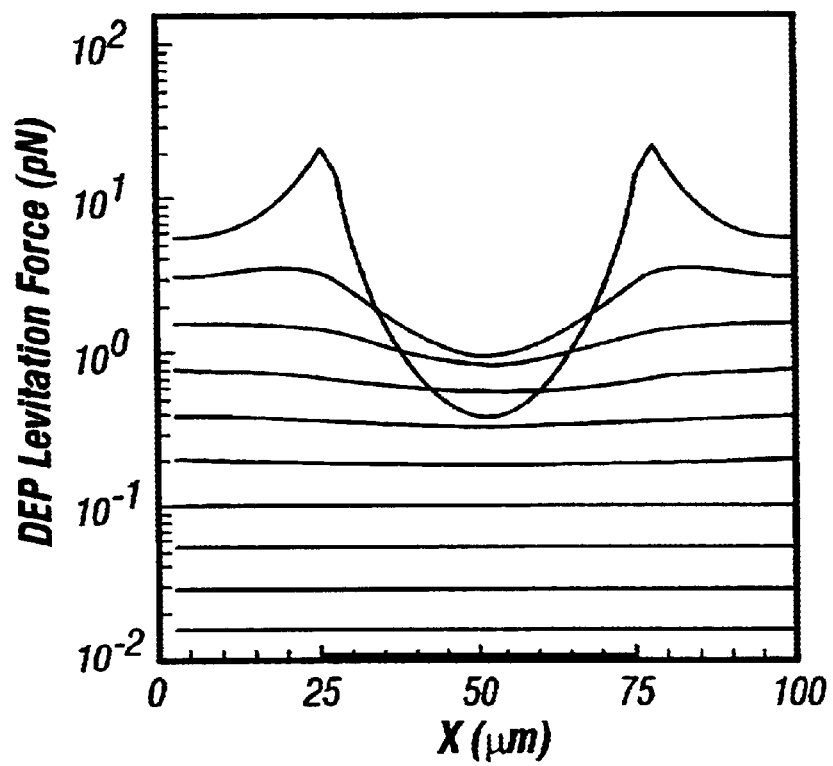
FIG. 20 Dependencies of vertical (levitation) DEP forces on the particle position relative to electrode edges for a parallel electrode array of 50 $\mu$m width and spacing. The bold line on the X-axis represents an electrode element. The electrical field simulation was performed using the Green's theorem-based analytical method (Wang et al., 1996). For the force calculation, a particle of radius r=5 $\mu$m and Re[$f_{CM}$]=−0.5 was subjected to an applied field of 1 V RMS. DEP levitation forces were calculated for particle heights between 5 (largest force) and 95 $\mu$m (smallest force) at 10 $\mu$m increments above the electrode plane.

As discussed above, PS beads should theoretically settle to their equilibrium height positions as determined by the balance of sedimentation and applied DEP forces during relaxation. However, the DEP levitation force is larger above the electrode edges of the electrode array and smaller over the centers of the electrodes and gaps (FIG. 20). As a result of this as well as certain imperfections such as occasional open circuits in electrode elements, some PS beads may settle to the chamber bottom surface. These may adhere to the chamber wall, where they can disturb the laminar flow profile when fluid flow is started, and impair the separation performance. Therefore, after several experiments, we realized that, in this example, an appropriate conditioning of the chamber bottom surface to inhibit particle adherence was critical to achieving optimum separation results.

The following procedures were developed for chamber surface treatment. Electrodes were first washed in 1% (w/v) Alconox detergent (Alconox Inc., NY), rinsed thoroughly with deionized water and air-dried before chamber assembly. To remove any residual water in the chamber, it was filled with ethanol and then dried with filtered, low pressure $N_2$. The chamber was then filled with Sigmacote (Sigma, MO) for 15 minutes and dried again with $N_2$. Each Sigmacote treatment, which applied a hydrophobic coating to the chamber walls, lasted for about twenty experiments. After each day's usage, the chamber was flushed with 60 ml of 1% (w/v) Alconox plus 0.05% (w/v) NaOCl (Clorox Inc., CA) solution at a flow rate 2 ml/min for 30 min. For overnight storage, the chamber was filled with this solution to ensure there was no growth of microorganisms. It has been found that the chamber can be used for many hundreds of experiments without noticeable changes in its separation performance, provided the electrode surface treatment described above is performed regularly.

Particle Kinetics

Figure 21:
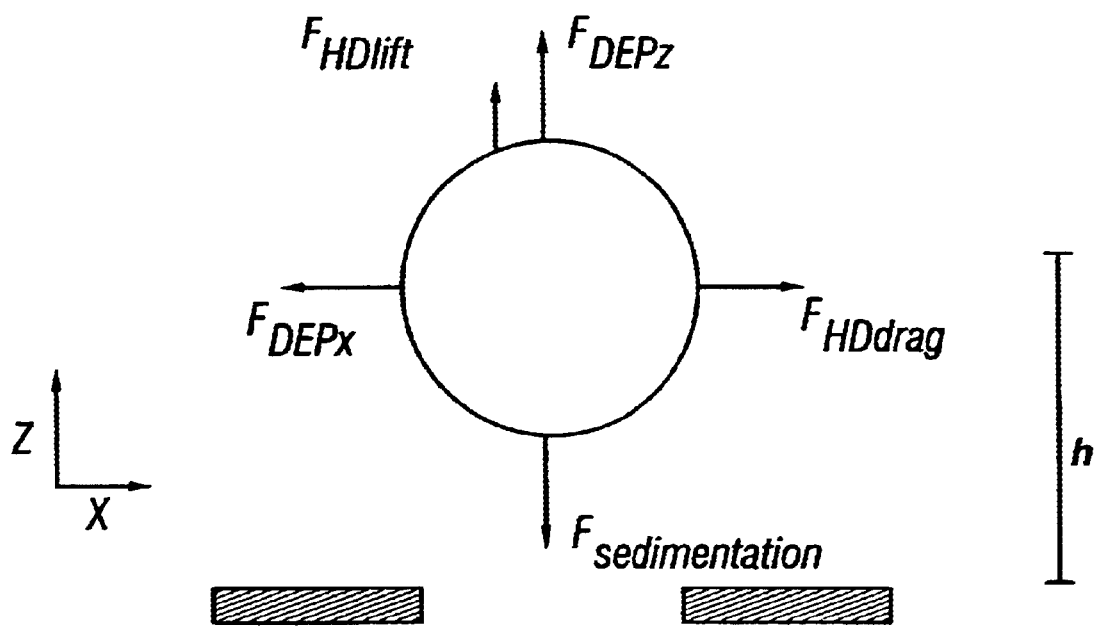
FIG. 21 Schematic representation of the instantaneous forces acting on a particle in a DEP/G-FFF chamber according to the present disclosure.

As illustrated in FIG. 21, a particle traveling in a DEP/G-FFF chamber experiences several forces. In the vertical direction, DEP levitation, sedimentation (gravitation) and HD lift forces act to determine the particle height in the fluid-flow profile. As a particle travels across the electrode array, the net force it experiences in the vertical direction alternates around zero. As a result, the particle will move up and down, and the magnitude of these height perturbations will depend on the instantaneous DEP levitation forces, the fluid viscosity, and the rate of travel across the electrode elements. We found that the oscillation of particle heights was quite small (<2 $\mu$m) at moderate or high fluid flow rates (>200 $\mu$l/min) because particles had a short time. (<20 ms) to respond to the variations in the vertical DEP force component.

In the fluid flow direction, a particle experiences fluid drag as well as a horizontal component of DEP forces from the electrodes (Wang et al., 1998). Although the net fluid drag would be zero if a particle moved at constant velocity at a fixed height in the fluid flow profile in the absence of an applied electrical field, the horizontal DEP force component causes the particle velocity to suffer perturbations. Nevertheless, because of the electrode periodicity, the average horizontal DEP force over a complete electrode/gap period is zero FIG. (Wang et al., 1998). Thus horizontal DEP forces have no effect on the average velocity of the particle. As a corollary, the velocity of particles depends only on their equilibrium height positions in the flow profile as determined by the balance of the average DEP levitation force and the sedimentation and HD lift forces; the horizontal DEP component does not influence particle velocities. This is one of the major differences between DEP/G-FFF and the early separation approach of DEP-retention. In that case, the horizontal DEP force component was used to compete with the fluid flow forces and thereby determine the particle elution rate (Becker et al., 1995; Markx et al., 1994; Talary et al., 1995).

Hydrodynamic (HD) Lift Forces

To investigate the HD lift effect, we conducted gravitational field-flow-fractionation experiments where no DEP forces were applied so that particle equilibrium positions were determined solely by sedimentation and HD lift forces. In these cases, based on experimental particle elution data and a theoretical analysis (Wang et al. 1998), we found that particle heights were essentially independent of the fluid flow rate and HD lift forces levitated PS beads only slightly and distances between particle peripheries and the chamber bottom wall were between only 0.4 and 0.7 $\mu$m. On the other hand, experimental particle elution data demonstrated that DEP forces can levitate particles much higher (up to 2 orders of magnitude) equilibrium positions that HD effects. We therefore conclude that hydrodynamic lift forces play little or no role in the DEP/G-FFF separations described here.

Optimization of DEP/G-FFF Separation

We have found that that the particle elution time may be determined by a number of operational parameters including the chamber height H and length L; the average fluid flow rate <$V_m$>; the electrode periodic distance d; the applied voltage U, the particle radius r, the particle dielectric polarization parameter Re($f_{CM}$), and the particle and suspension densities $\rho_p$ and $\rho_m$. Separation by DEP/G-FFF can therefore exploit differences in particle size, density and dielectric properties.

As in most FFF applications, we have assumed that a parabolic flow profile exists in the vertical direction of the DEP/G-FFF chamber and that the shape of this profile is determined by the chamber height H. For achieving better separation performance, we have found that the chamber height H should be chosen so as to maximize the fluid velocity gradient, given by, $$dV_m/dh = \frac{6\langle V_m \rangle}{H^2}(H - 2h). \tag{17}$$

The gradient $dV_m/dh$ increases as the particle height h is decreased in the flow profile so that better velocity differentiation may be achieved for particles equilibrated closer to the chamber bottom surface. For particles having a maximum levitation height $h_{max}$, the choice of the chamber height H may depend on the specific optimization criteria. For example, to maximize the average velocity gradient between 0 and $h_{max}$ the chamber height should be $2h_{max}$; to maximize the gradient at $h_{max}$ the chamber height should be $4h_{max}$.

The particle elution time and the degree of separation between different particle types are proportional to the chamber length L, thus better separation may be achieved by increasing L. The particle elution time is inversely proportional to the averaged fluid velocity <$V_m$> so that increasing the flow rate may result in faster separation. Nevertheless, at sufficiently high values of the fluid flow rate, the HD lift may impair particle separation. Other undesirable effects may also come into play at very high flow rates.

Electrode arrays with large d values may be preferred for increasing the resolution of dielectric discrimination. Electrodes having large d values may, however, require a much higher field strength (E) to generate sufficiently strong DEP levitation forces (proportional to $E^2/d$). A higher field strength may cause, in turn some undesirable effects such as Joule heating of the suspending medium.

As shown in FIGS. 17A, 17B, and 18 the applied voltage U is an important variable for DEP/G-FFF operation. Generally, large voltages levitate particles to higher equilibrium positions where the gradient of the fluid velocity is reduced. To exploit the region of large velocity gradient in the fluid flow profile for better particle separations, small voltages may be preferred. On the other hand, HD lift effects at low positions in the profile may complicate particle kinietic behaviors and small voltages also result in longer separation times. Clearly the applied voltages should be optimized for each application.

The density $\rho_m$ of suspending medium is another important variable for DEP/G-FFF. For stable positioning of particles in the flow profile, negative dielectrophoretic forces and negatively buoyant particles should be used. $\rho_m$ should therefore be smaller than the densities ($\rho_p$) of the particles (Gascoyne et al., 1996; Huang et al., 1997). The value for $\rho_m$ may be chosen based on the following criteria. If $\rho_m$ is much smaller than $\rho_p$, then a large voltage and field strength may have to be applied to levitate the particles. On the other hand, if $\rho_m$ is just slightly below $\rho_p$, then a long time may be necessary for particles to relax to their equilibrium positions after introduction into the chamber.

The applied field frequency f and the dielectric properties (electrical conductivity and permittivity) of suspending medium are important factors in determining the dielectric polarization factor Re($f_{CM}$) of the particles (Gascoyne et al., 1997; Wang et al., 1997), and should be optimized by maximizing the differences in $Re(f_{CM})$ the real component of the Clausius-Mossotti factor that reflects the magnitude and direction of field-induced polarization in the particle at frequency f, between particles to be separated. As long as the applied DEP levitation forces (a function of the field frequency f and dielectric properties of suspending medium) are effective in controlling particle equilibrium heights in the flow profile, the DEP/G-FFF system may be used for particle characterization and separation. In contrast to particle separations using DEP-retention (Wang et al., 1993, Becker et al., 1995) where different particles must have different polarities for $Re(f_{CM})$, DEP/G-FFF separations require that different particles have different negative $Re(f_{CM})$ values. As shown previously in DEP/G-FFF (Huang et al., 1997), particle velocity (and therefore the retention time) is very sensitive to $Re(f_{CM})$, suggesting considerably higher particle discriminations for DEP/G-FFF than for the DEP-retention method.

Conclusions

This example has shown that dielectrophoretic/gravitational field-flow fractionation is an effective method for particle separation. It may be readily applied for the separation of particles of ~1 µm to several hundred micrometers. It exploits not only differences in particle size and density, as in a number of other FFF techniques, but also, and most significantly, the particle dielectric properties. For biological cells, DEP/G-FFF separation may be based on differences in cell size, membrane capacitance and conductance (Gascoyne et al., 1997; Huang et al., 1997) and cell interior dielectric properties. For colloidal particles such as polystyrene beads, DEP/G-FFF separation may utilize differences in particle size, particle surface properties (such as surface charge) and bulk dielectric properties.

DEP levitation forces, generated by applying a relatively small AC voltage (<10 V p-p) to microelectrodes on the bottom surface of the separation chamber, may be used to balance the gravitational (sedimentation) forces acting on the particles so as to position them in a flow velocity profile. Particles possessing different dielectric and density properties equilibrate at different heights and are carried at different velocities in a flow profile. As a result different particles elute from the separation chamber at different times. The separation method is flexible because it depends on a number of operational parameters including the density and dielectric properties of the particle suspending medium and the voltage and frequency of the applied DEP field. These parameters may be varied to optimize separation performance for specific applications. The operational field frequency is typically above 1 kHz. This minimizes several undesired effects including electrode polarization and water electrolysis at electrode surfaces. The separation chamber may be readily miniaturized for applications demanding the use of even minute quantities of samples. Finally, DEP/G-FFF can be used to study the physical properties of particles. For example, the particle dielectric properties can be derived by determining the dependencies of their elution times on the frequency and voltage of the applied DEP field.

EXAMPLE 4

Cell Separation on Microfabricated Electrodes Using Dielectrophoretic Field-Flow-Fractionation Dielectrophoretic/gravitational field-flow-fractionation (QEP/G-FFF) was used to separate cultured human breast cancer MDA-435 cell's from normal blood cells mixed together in a sucrose/dextrose medium. An array of microfabricated, interdigitated electrodes of 50 um widths and spacings, and lining the bottom surface of a thin chamber (0.42 mm H×25 mm W×300 mm L), was used to generate DEP forces that levitated the cells. A 10-uL cell-mixture sample containing ~50,000 cells was introduced into the chamber, and cancerous and normal blood cells were levitated to different heights according to the balance of DEP and gravitational forces. The cells at different heights were transported at different velocities under the influence of a parabolic flow profile that was established in the chamber and were separated. Separation performance depended on the frequency and voltage of the applied DEP field and the fluid-flow rate. It took as little as 5 min to achieve cell separation. An analysis of the dependency of cell elution-time and equilibrium height on the DEP field frequency revealed that the separation exploited the difference in dielectric and density properties between cell populations. The significance of DEP/G-FFF technique for cell processing has been recognized, particularly in relation to the development of integrated microfluidic systems.

Experimental Details

The DEP/G-FFF System

The experimental setup for the DEP/G-FFF system is similar to that shown in FIG. 13 and has been described in detail in the article by Yang et al (1999a). Briefly, \interdigitated microelectrodes, 50 µm in width and gaps, were fabricated on 50×50-mm glass substrates using standard photolithography. Six electrodes were glued end-to-end onto a supporting glass plate to form one electrode plate. The DEP/G-FFF chamber was constructed by sandwiching a Teflon spacer (0.42 mm H×50 mm W×300 mm L) between a top glass plate and the bottom electrode plate with 36 Nylon screw-clamps (Bel-Art Products, Paquannock, N.J.). The spacer was cut to provide an open channel with dimensions of 288 mm from tip to tip and 25 mm in width except at the tapered ends. The microelectrodes, each having two 4-mm wide electrical conductor buses running along the edges, were connected in parallel to a lab-built PA-05 based power amplifier (Apex Microtechnology, Tucson, Ariz.). The signals to the amplifier were produced from a function generator (model 33120A, Hewlett-Packard, Santa Clara, Calif.) and monitored by an oscilloscope (model RDS 320; Tektronix, Pittsfield, Mass.).

The top and bottom plates were drilled with 0.0625 in-diameter holes to fit inlet and outlet tubing at positions coincident with the points of the tapered ends of the DEP/G-FFF channel. To allow sample introduction, PEEK tubing, having a void volume of 2.5 µL, served as the connection between an injection valve (model 7010 equipped with a 10-(L loop; Rheodyne, Rohnert Park, Calif.) and the chamber inlet port. A digital syringe pump (Daigger, Wheeling, Ill.) was used to provide a continuous flow of carrier medium through the channel. Cells exiting the outlet tubing of the chamber were collected with a fraction collector (model Cygent 68-2170; Isco, Lincoln, Nebr.). The fraction collector can operate by collecting sample fractions at fixed time intervals or fixed drop number intervals. Cell kinetic behaviors in the chamber were monitored under a microscope (model Microphot-SA; Nikon, Melville, N.J.) equipped with a CCD camera (Hamamatsu, Bridgewater, N.J.) and a video monitor. Cell equilibrium heights were determined by differences in the microscope focal positions of the electrode plane and the cells, multiplied by the refractive index of the fluid in the chamber.

Cell Preparation

Cultured human breast cancer MDA-435 cells mixed with normal human peripheral blood cells (mainly erythrocytes)

were used as a model system in this study. MDA-435 cells, derived from a pleural effusion of a patient with metastatic breast cancer (Cailleau et al. 1978; Zhang &Fidler 1991), were cultured in minimum essential/F12 medium supplemented with 10% fetal bovine serum, 1 mM glutamine, and 20 mM HEPES (Life Technologies, Gaithersburg, Md.), plus 0.5% penicillin and streptomycin (Sigma Chemical Co., St. Louis, Mo.), and were maintained in 75-cm² plastic flasks under a 5% $CO_2$/95% air atmosphere at 37° C. in a humidified incubator. The cells were harvested at ·80% confluence 48 h after seeding by brief exposure to 0.25% trypsin-0.02% EDTA followed by approximately 15 min recovery in complete medium. Cell mixtures were prepared by adding an aliquot of fresh EDTA-anticoagulated human blood to a suspension of harvested MDA-435 cells, and then washed twice in an isotonic 8.5% (w/v) sucrose plus 0.3% (w/v) dextrose buffer. The electrical conductivity of the sucrose buffer was adjusted to 56 mS/m with minimum essential medium, as determined with a conductivity meter (EC19101-00; Cole-Parmer Instrument, Chicago, Ill.). The final concentration of cells in the sucrose/dextrose buffer was $5 \times 10^6$ cells/mL at a nominal ratio of 2:3 for cancer to normal blood cells. It is noted that the above cell preparation procedure removed the human blood plasma from the cell mixture. However, removal of the plasma components is not critical for the DEP/G-FFF separation described in this work. Separation experiments were conducted in which the cell mixture was prepared by adding diluted human blood to a suspension of breast cancer cells. The separation performance was not affected, provided the electrical conductivity of the final cell suspension was maintained at an appropriate value.

Specific density values were determined for erythrocytes and MDA-435 cells as 1.095 and 1.072 $kg/dm^3$, respectively, with a centrifugally generated continuous Percoll density gradient (Pharmacia, Uppsala, Sweden) calibrated by density marker beads.

Cell Separation Protocol

The DEP/G-FFF chamber was first loaded with the isotonic sucrose/dextrose buffer. The cell mixture sample was then introduced into the inlet port of the chamber through the injection valve. To accomplish this, the 10 $\mu$L-loop on the injection valve was first loaded with cell sample using a manually operated syringe. The valve was then switched to the "injection" mode and 35 $\mu$L sucrose/dextrose buffer was flushed through the loop by the syringe pump operating at 50 $\mu$L/min to move all the cells into the DEP/G-FFF chamber. Appropriate voltage signals were applied to the microelectrodes during the sample introduction so that the cells would be levitated in the chamber by DEP forces, thereby preventing possible adherence of the cells to the bottom surface of the chamber. Following injection, cells were allowed 5 min to attain equilibrium heights at which the opposing DEP and gravitational forces acting on them were balanced. Flow of carrier medium through the chamber was then started using the syringe pump, and, because of geometrical characteristics, a parabolic hydrodynamic flow profile was established inside the chamber. Under the influence of fluid drag, cells were caused to move at different velocities according to their relative positions in the flow profile. Cells were collected as they exited the chamber using a fraction collector and then characterized. To evaluate separation performance, cell fractograms were obtained by counting cells under video microscopy as they passed through a detection window at the outlet end of the chamber. The different cell types were identified by size (MDA-435 cells and erythrocytes are ~15 $\mu$m and 7 $\mu$m in diameter, respectively).

Based on their fractograms, two parameters were defined for each cell type to describe the elution characteristics of the cells, namely, the elution-time and the elution-peak width. These parameters were determined from the integral of cell number with time, the accumulated count of cells as they passed through the detection window. Elution-time was taken as the time at which the integral reached 50% of its maximum. Elution-peak width was defined as the time taken for the integral to increase from 12.5% to 87.5% of its maximum. The elution-peak width definition corresponded to the width at half-height for peaks having triangular or normal distributions in time.

Theory

DEP/G-FFF Principle

Figure 22:
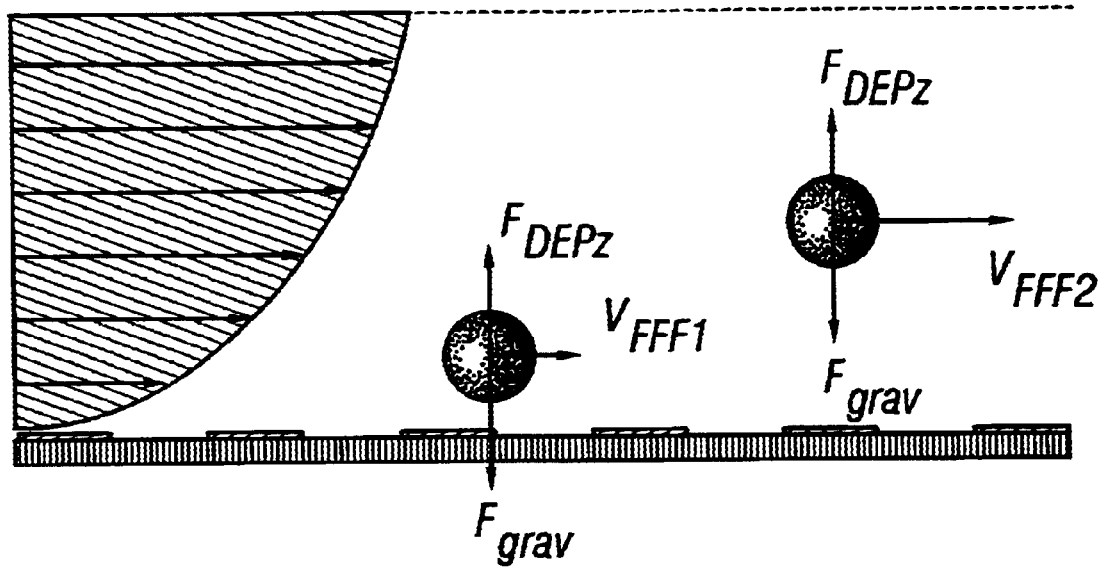
FIG. 22 Schematic drawing of dielectrophoretic/ gravitational field-flow-fractionation principle. Cell equilibrium height in the fluid-flow profile may be determined by the balance of DEP levitation forces ($F_{DEPz}$) generated by the microelectrodes and the sedimentation force ($F_{grav}$). Cells that are farthest from the bottom electrode plane are carried faster by the fluid ($V_{FFF2}>V_{FFF1}$) and exit the chamber earlier than those at lower positions.

FIG. 22 gives a schematic representation of dielectrophoretic/gravitational field-flow-fractionation principle. The bottom surface of the chamber is lined with an interdigitated microelectrode array. The DEP levitation force caused by the interdigitated electrodes acting on an elliptical cell of volume V is given by (Huang et al, 1997, Wang et al., 1998)

$$F_{DEPz} = 1.5 V \in_m \alpha_{DEP}(f) U^2 p(f) A \exp(-2\pi h/d) \tag{18}$$

where U is the applied RMS voltage at a frequency f, $\in_m$ is the dielectric permittivity of the medium, and $\alpha_{DEP}(f)$ (=Re($f_{CM}$)) is a factor characterizing the field-induced polarization in the cell. The parameter p(f) is included to correct for electrode polarization (Schwan, 1992). DEP forces fall approximately exponentially with height h above the electrode plane, with a decay constant that is characterized by the periodic distance d of the electrode array and a unit-voltage force coefficient A. The gravitational force is given by $-V(\rho_c - \rho_m)g$. Here $\rho_c$ and $\rho_m$ are the densities of the cell and its suspending medium, respectively, satisfying the relationship $\rho_c > \rho_m$. The balance of gravitational and DEP levitation forces positions the cell at a stable equilibrium height, $$h_{eq} = \frac{d}{4\pi} \ln\left( \frac{3\varepsilon_m U p(f)}{2g} \frac{A \alpha_{DEP}(f)}{(\rho_c - \rho_m)} \right). \tag{19}$$

Equilibrium heights are dependent on the dielectric property (as characterized by the dielectric polarization factor $\alpha_{DEP}$) and density ($\rho_c$) of the cell, of the electrode dimensions (A and d), of the applied DEP field strength (U) and frequency (f), and of the electrode polarization parameter p(f).

The velocity with which a cell located at a height $h_{eq}$ from the chamber bottom surface is carried along by the parabolic flow profile in the chamber is given by (Williams et al., 1992)

$$V_c = K_r \cdot 6\langle V_m \rangle \frac{h_{eq}(H - h_{eq})}{H^2} \tag{20}$$

where H is the chamber thickness, and $\langle V_m \rangle$ is the mean fluid velocity. $k_r$ (<1) is a coefficient that characterizes a retardation effect (Williams et al, 1992) that occurs when particles are close to the chamber wall. Thus, by careful selection of the DEP field conditions, cells having different dielectric and density properties can be levitated to different heights above the electrode surface and thereby be caused to move at different velocities under the influence of the flow profile.

Cell Dielectric Modeling

For an elliptical particle, the dielectric polarization factor $\alpha_{DEP}(f)$ along the j-axis of the ellipsoid is given by (Kakutani et al, 1993)

$$\alpha_{DEP}(f) = Re\left(\frac{(\varepsilon_c^* - \varepsilon_m^*)}{(3(\varepsilon_c^* - \varepsilon_m^*)A_j + 3\varepsilon_m^*)}\right) \quad (21)$$

where $\in_c^*$ and $\in_m^*$ are the frequency-dependent complex dielectric permittivities of the cell and its suspending medium, respectively, and $A_j$ is the depolarization factor along the j-axis (j=x, y, z). In this work, human breast cancer MDA-435 cells are modeled as spherical particles ($A_j$= 0.333) consisting of an internal homogeneous dielectric sphere (radius r) surrounded by a poorly conducting plasma membrane of thickness d. The effective complex permittivity is then given by (Fuhr & Hagedorn, 1996; Irimajiri et al, 1979; Huang et al, 1992)

$$\varepsilon_c^* = \varepsilon_{mem}^* \left(\frac{\frac{(r+d)^3}{r^3} + \frac{2(\varepsilon_{int}^* - \varepsilon_{mem}^*)}{\varepsilon_{int}^* + 2\varepsilon_{mem}^*}}{\frac{(r+d)^3}{r^3} - \frac{\varepsilon_{int}^* - \varepsilon_{mem}^*}{\varepsilon_{int}^* + 2\varepsilon_{mem}^*}}\right) \quad (22)$$

where $\in_{mem}^*$ and $\in_{int}^*$ refer to the complex permittivities of the cell membrane and interior, respectively. Erythrocytes are modeled as single-shell oblate ellipsoids having semi-axes of a, b, and c, satisfying the relationship a=b>c. The shell and interior refer to the cell membrane and cytoplasm, respectively. The cell effective permittivity for such ellipsoids is given by (Kakutani et al, 1993)

$$\varepsilon_c^* = \varepsilon_{mem}^* \left(\frac{\varepsilon_{mem}^* + (\varepsilon_{int}^* - \varepsilon_{mem}^*)(A_j + \upsilon(1 - A_j))}{\varepsilon_{mem}^* + (\varepsilon_{int}^* - \varepsilon_{mem}^*)(A_j - \upsilon A_j)}\right). \quad (23)$$

where v is the volume fraction of the cell interior v=(c-d)(a-d)²/ca². The depolarization factor is given by $$A_j = 0.5(e^2 a \tan(e^2-1)^{0.5}-(e^2-1)^{0.5})/(e^2-1)^{1.5} \quad (24)$$

where e=a/c>1. Therefore, with the knowledge of the cell dielectric parameters in the shell models, it is possible to calculate their complex permittivities using Equations (22) and (23).

Results

Figure 23:
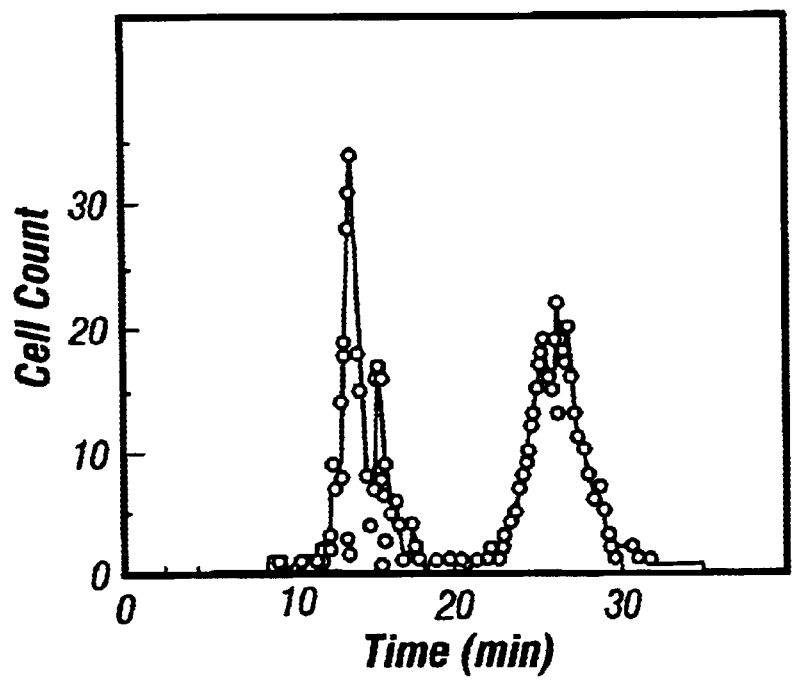
FIG. 23 Time dependency of the numbers of MDA-435 cells (first peak, square) and erythrocytes (second peak, circle) passing by an inspection widow at the chamber outlet port for a DEP field of 1.4 V RMS at a frequency of 5 kHz. MDA-435 cells moved ahead of erythrocytes, and the two populations were well separated. The cells were suspended in an isotonic sucrose/dextrose buffer that had an electrical conductivity of 56 mS/m. The flow rate was 0.5 mL/min, corresponding to a mean fluid velocity of 780 $\mu$m/sec.

A typical cell fractogram illustrating the time dependency of the number of MDA-435 cells and erythrocytes passing through the detection window is shown in FIG. 23 for an applied DEP field frequency of 5 kHz. The two cell-populations were well separated with an elution-time difference of 12 min. This result was in agreement with the visual inspection of cell motion under video-microscopy, revealing that MDA-435 cells moved almost twice as fast as erythrocytes. The elution-peak widths for MDA-435 cells and erythrocytes depended on several factors. The elution-time for each cell depended on its velocity and travel distance through the DEP/G-FFF chamber. Since it was not possible to ensure that all the cells were positioned the same distance from the chamber outlet port during sample loading, a small spread in elution-times was expected even for the cells having the same velocity. Furthermore, different cells of the same type exhibited different velocities because of inherent population heterogeneity in the cell dielectric properties caused by differences in cell composition, morphology, and structural organization (**Huang et al., 1996; Fuhr & Hagedorn, 1996; Pethig & Kell 1987; Becker et al, 1995; Gascoyne et al, 1997). The apparent double-peak for MDA-435 cells appears to be associated with a real distribution of cell dielectric parameters.

Figure 24A:
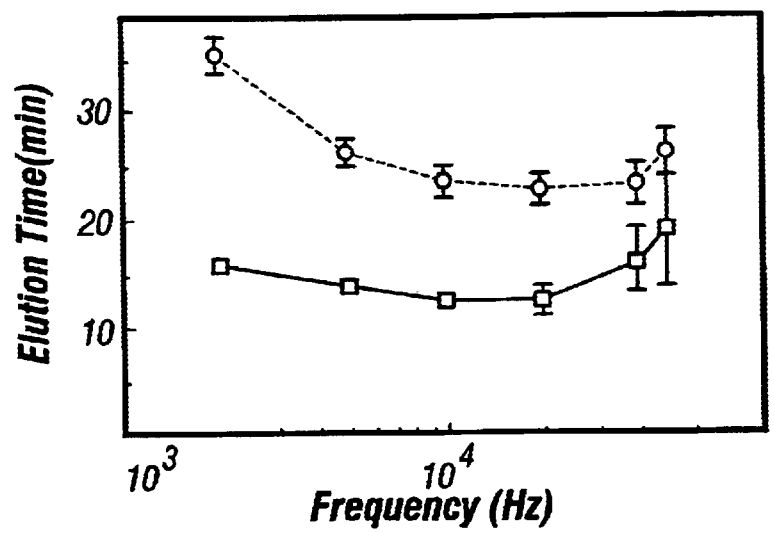
FIG. 24A Frequency dependency of the elution-time for MDA-435 cells (square) and erythrocytes (circle), with the error bars representing the elution-peak width. The two cell populations were well separated at frequencies below 20 kHz. The elution-time and elution-peak width were derived from the cell fractograms like those shown in FIG. 23 according to the method described in the Experimental Section. Cell suspension, DEP field, and fluid-flow conditions are the same as in FIG. 23.

The dependency of cell elution-time on the frequency of the applied DEP field is shown in FIG. 24A. At 2 kHz, MDA-435 cells and erythrocytes were well separated with an elution-time difference of ~20 min. In the frequency range of 2 to 10 kHz, the elution-time difference between the two cell-populations was between 11 and 20 min. The elution-peak widths were quite narrow (1.7–3.5 min.), leading to good cell separation even though the two elution peaks were closer together at 10 kHz. Elution-time decreased with increasing frequency, reflecting an increase in cell velocities. As the frequency was increased to 50 kHz, elution-times and elution-peak widths increased slightly for erythrocytes, and much more for MDA-435 cells, indicating that the velocities of MDA-435 cells not only dropped but also exhibited a wide distribution. The two populations were not well separated at 40 and 50 kHz because of a broadening of the peaks.

Figure 24B:
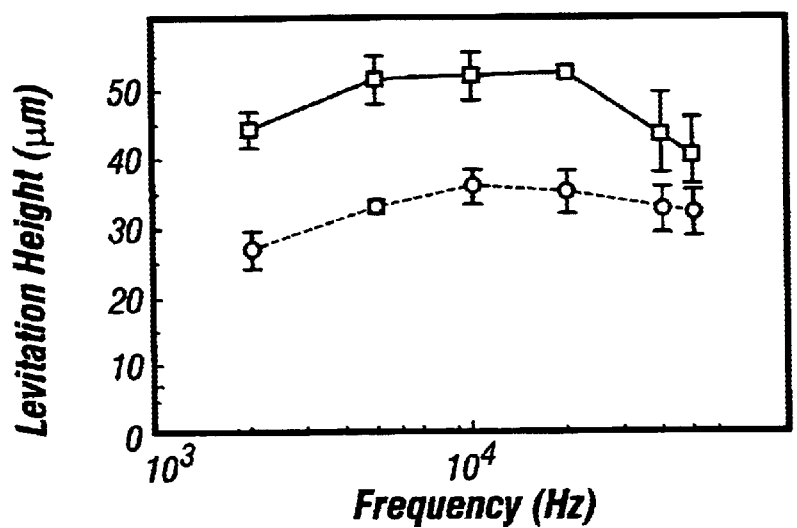
FIG. 24B Frequency dependencies of equilibrium levitation height for MDA-435 cells (square) and erythrocytes (circle) under a fluid flow of mean velocity 16 $\mu$m/sec. MDA-435 cells were levitated higher than erythrocytes with height difference up to 15 $\mu$m. The heights are averages for at least 10 cells. Error bars indicate the standard deviations of the measured heights. Cell suspension and DEP field conditions are the same as for FIG. 23.

Differences in elution-time between the two populations resulted from the differential velocities of the cells, which in turn reflected the differences in the cell equilibrium heights in the fluid-flow profile. To verify the height-velocity relationship in the DEP/G-FFF chamber, equilibrium heights for individual MDA-435 cells and erythrocytes were measured under light microscopy for a slow flow ($<V_m>$=16 µm/sec) at a number of DEP field frequencies (FIG. 24B). As anticipated from their larger velocities, MDA-435 cells were found to be levitated to higher positions than erythrocytes. Depending on the frequency, the difference in the mean cell height between MDA-435 cells and erythrocytes was as large as 15 micrometers. For each cell population, the dependency of equilibrium height on DEP field frequency was in qualitative agreement with the peak-time data shown in FIG. 24A. For example, low equilibrium heights with a large deviation for MDA-435 cells at 50 kHz accounted for the large elution-time and elution-peak width observed under these conditions.

Figure 24C:
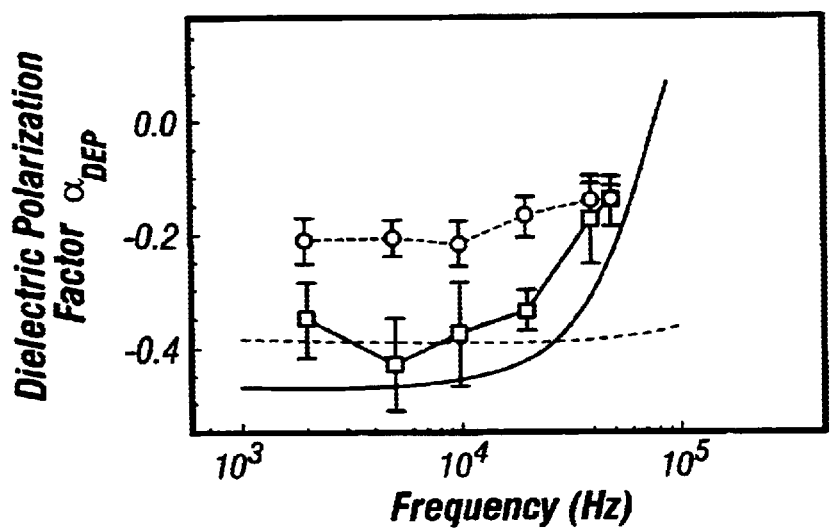
FIG. 24C Frequency dependencies of the polarization factor $\alpha_{DEP}$ for the MDA-435 cells (square) and erythrocytes (circle) derived from levitation height curves in (B) using Equation (19) with the following parameters.

Cell equilibrium heights were determined by the balance of DEP levitation forces and gravitational forces. To understand the basis for the difference in equilibrium heights between MDA-35 cells and erythrocytes, we calculated the frequency-dependency of the dielectric factor $\alpha_{DEP}$ (FIG. 24C) for the two cell populations from observed levitation heights using standard equations with the knowledge of DEP field conditions and cell density values. Whereas $\alpha_{DEP}$ for erythrocytes exhibited little variation over the frequency range of 2 to 50 kHz, the magnitude of $\alpha_{DEP}$ for MDA-435 cells displayed a frequency dependency. The difference in $\alpha_{DEP}$ between the two cell types at frequencies below 20 kHz indicated that the greater levitation (and correspondingly larger velocity) exhibited by MDA-435 cells were caused not only by their smaller density (1.072 vs 1.095 kg/dm³) but also by their larger polarization factors (−0.36 vs−0.21).

To illustrate the basis for the difference in dielectric properties of MDA-435 cells and erythrocytes, the dielectric factor $\alpha_{DEP}$ was calculated by cell dielectric modeling. Based on their geometry, we modeled MDA-435 cells and erythrocytes as single-shell spheroids and oblate ellipsoids, respectively, where the outer shells corresponded with the plasma membranes. Compared with erythrocytes, $\alpha_{DEP}$ for MDA-435 cells was larger in the frequency range of 2 to 20 kHz and exhibited a frequency dispersion above 40 kHz. These differences originated from the fact that the size and membrane capacitance of MDA-435 cells were larger than those of erythrocytes and that MDA-435 cells were spherical, whereas erythrocytes were double-discoid. Therefore, we have concluded that the DEP/G-FFF separation of MDA-435 cells and erythrocytes reported here exploited differences in cell density, size, shape, and membrane electrical properties as separation criteria.

Cells exiting the DEP/G-FFF chamber were collected with a fraction collector. At a DEP field frequency of 10 kHz and a fluid-flow rate of 1 mL/min, the cells were collected into 15 fractions at a time interval of 2 min. Fractions 5 to 7 and 9 to 13 included >98% of MDA-435 cells and >99% of erythrocytes, respectively. Furthermore, Trypan blue staining of the collected cells revealed that >99% of the cells excluded the stain, demonstrating that membrane integrity was maintained during DEP/G-FFF separation.

Operational conditions such as DEP field voltage and fluid-flow rate were changed to examine their influences on separation performance. FIG. 25A shows the voltage dependency of the elution-time for the MDA-435 cells and erythrocytes at 20 kHz. Evidently, the larger the applied voltage, the shorter the elution-time. This result was predicted because larger voltages increased DEP levitation force and thereby caused cells to be positioned higher in the fluid-flow profile where they were carried faster. FIG. 25A further shows that the elution-peak width increased significantly with decreasing applied voltage. An important factor influencing the elution-peak width is the heterogeneity in cell dielectric properties. Individual cells of the same type having different dielectric properties were positioned at different heights in the flow profile and therefore traveled through the DEP/G-FFF chamber at different velocities. With decreasing voltage, the cells were positioned lower in the fluid-flow profile where larger velocity gradients existed. Thus, the cells with slightly different dielectric properties were carried by the fluid flow at velocities with larger differences, leading to increased elution-peak widths.

FIG. 25B demonstrates the effect of the fluid-flow rate on cell elution-time. The elution-time was found to be inversely proportional to the flow rate, indicating that the cell equilibrium heights were not affected by the change in the flow rate. Efficient separations of the two populations could be achieved in less than 8 min at a flow rate of 2 mL/min. FIG. 25B further shows that the elution-peak width increased with decreasing fluid-flow rate. Nevertheless, the ratio of the elution-peak width to elution-time remained almost unchanged for different flow rates, supporting the conclusion that the flow rate did not influence cell equilibrium heights.

We have found that the cell equilibrium heights in the DEP/G-FFF chamber were almost independent of the flow rate, which confirms that the applied DEP levitation forces were much stronger than this hydrodynamic lift force. This finding is in agreement with theoretical analyses of the hydrodynamic lift force (Yang et al, 1999a).

To further demonstrate the general applicability of DEP/G-FFF to cell-separation problems, experiments were conducted in which cultured human leukemia HL-60 cells were separated from a mixture with normal blood cells and MDA-435 cells were separated from a mixture with purified human T-lymphocytes (unpublished data). The results achieved were consistent with those in our MDA-435/erythrocyte study, indicating that this method may have applications to a number of cell separation needs.

When the cells were initially loaded into the chamber, they exhibited a wide distribution of heights. In order for the cells to reach equilibrium positions, they were allowed 5 min to sediment before the fluid flow was applied. Allowing sufficient time for this initial sedimentation (the so called relaxation time) was important for ensuring good separation performance.

We were able to sort ~50,000 cells in each experiment at a rate of several thousands per minute. Because the electrode array has no moving parts and a single amplifier can be used to power it, the DEP/G-FFF device may easily be scaled up as necessary for routine cell separation in biological and clinical labs, handling $10^6$ or more cells in each separation. Furthermore, the DEP/G-FFF principle may be readily implemented in microfluidic systems for processing cell samples in the volume range of nanoliters to microliters. The only issue associated with miniaturization of the DEP/G-FFF device is that the chamber has to be long enough to provide sufficient resolution for the desired cell separation. Our work (unpublished data in the lab) has shown that the total length may be as short as 5 cm and that under our flow conditions, this may be achieved in a space-efficient serpentine configuration. The miniaturized DEP/G-FFF device may be interfaced to other microflume components including micro PCR and capillary electrophoresis devices, cell counters, and electrochemical detectors. In addition, the DEP/G-FFF method exploits cell dielectric and density properties, adding a new dimension to cell separation. The capability of DEP/G-FFF separation according to density properties suggests that it may be used in integrated microflume systems as a substitute for centrifugation, which is currently used as a basic step in cell sample preparation. Finally, the technique is noninvasive and does not rely on the interaction of antibodies with cell-surface antigens, making it potentially attractive for applications such as the separation of leukocyte subpopulations without the potential problems of cell activation inherent in immuno-selective methods.

EXAMPLE 5

The principle of cell characterization and separation by dielectrophoretic field flow fractionation has been achieved. The operational device in this example took the form of a thin chamber in which the bottom wall supported an array of microelectrodes. By applying appropriate AC voltage signals to these electrodes, dielectrophoretic forces were generated to levitate cells suspended in the chamber and to affect their equilibrium heights. A laminar flow profile was established in the chamber so that fluid flowed faster with increasing distances from the chamber walls. A cell carried in the flow stream attained an equilibrium height, and a corresponding velocity, based on the balance of dielectrophoretic, gravitational and hydrodynamic lift forces it experienced. We have described a theoretical model (Huang et al., 1997) for this system and have shown that the cell velocity is a function of the mean fluid velocity, the voltage and frequency of the signals applied to the electrodes, and, most significantly, the cell dielectric properties. The validity of the model has been demonstrated using human leukemia (HL-60) cells subjected to a parallel electrode array, and the application of the device in separating HL-60 cells from peripheral blood mononuclear cells has been achieved.

The operational principle of DEP-FFF may be summarized as follows: by applying appropriate voltage signals to electrodes, particles having different dielectric and/or density properties may be levitated to different heights and thereby caused to move at different velocities under the influence of the flow profile. Particles preloaded at the chamber inlet will then exit the chamber at different times where they can be collected separately. In this way, the times taken for particles to transit the chamber directly reflect their dielectric and density properties, and this dependency can be utilized for particle characterization and separation. In DEP-FFF, particles are positioned in different planes throughout the hydrodynamic flow profile above the electrode surface as a result of the balance between sedimentation, vertical DEP, and hydrodynamic-lift forces. Thus particles may be eluted in a continuous fashion at different velocities under the influence of horizontal fluid drag acting in their respective planes. In this way, DEP-FFF utilizes the full range of fluid velocities within the flow profile, and more importantly, exploits the three dimensional capacity of the separation chamber.

Material and Methods
Cells

The human leukemia HL-60 cell line was used as a model system in this study. Cells were cultured in RPMI 1640 medium supplemented with 10% fetal bovine serum, 1 mM glutamine and 20 mM HEPES (Life technologies, Gaithersburg, Md.), 0.5% penicillin and streptomycin solution (Sigma, St. Louis, Md.), and were maintained in 75 cm$^2$ plastic flasks under a 5% $CO_2$/95% air atmosphere at 37° C. in a humidified incubator. HL-60 cells were harvested at a density of 2×10$^6$/ml in the exponential growth phase by gently rocking the flask 48 h after seeding. Cell suspensions were found to have >98% viability by Trypan blue dye exclusion. Cells were harvested from complete medium by centrifugation at 100 g for 10 minutes and were then resuspended at a density ~10$^6$/ml in isotonic 8.5% (w/v) sucrose plus 0.3% (w/v) dextrose buffer. The conductivities of the final suspensions were adjusted with culture medium to a nominal value of 50 mS/m, and were then measured with a conductivity meter (EC19101-00, Cole-Parmer Instrument, Chicago, Ill.). Peripheral blood mononuclear (PBMN) cells were prepared from a buffy coat by standard density gradient separation. In order to quantify cell levitation effects, the specific densities of HL-60 cells were assessed to be 1.071±0.003 g/cm$^3$ with centrifugally-generated continuous Percoll density gradients (Pharmacia, Uppsala, Sweden) calibrated by Percoll density marker beads. The specific density of the cell suspending medium was measured as be 1.033 g/cm$^3$ with a hydrometer (VWR Scientific, Greenbelt, Md.).

Electrode chambers

Parallel electrode arrays, shown in FIG. 26, were fabricated using standard photolithography. In brief, gold-coated (thickness 250 Å over a 100 Å titanium seeding layer) glass blanks (Thin Film Technology, Buellton, Calif.) were spin-coated at 3000 rpm with S1830 photoresist (Shipley, Marlborough, Mass.) to ~1 $\mu$m thickness. The photoresist was polymerized by baking on a hot-plate at 110° C. for 1 minute and then exposed to UV light through a positive mask image (Process Technologies, Oak Creek, Wis.) of the electrode array using a mask aligner (AB Manufacturing, San Jose, Calif.). The exposed photoresist was developed with MF351 developer and the exposed gold and titanium region was then etched. Finally, the photoresist covering the unetched regions of the electrodes was removed with acetone. Arrays of parallel electrode elements having equal widths and gaps of 20 and 50 $\mu$m were both used in this study.

Chambers of dimensions 200 $\mu$m (H)×25 mm (L)×17 mm (W) were constructed of parallel top and bottom glass plates separated by a Teflon spacer, as shown in FIG. 26. The arrays of parallel electrodes were on the inner surface of the bottom plates. Polyethylene tubes (I.D.: 0.87 mm; O.D.: 1.22 mm) glued into holes drilled through the top glass plate with a diamond drill allowed for the introduction and removal of cell suspensions and eluate buffer.

Cell DEP-FFF Kinetics

After introduction of a cell sample into the chamber inlet, cells were allowed to settle onto the electrode plane for about 20 s prior to the application of electrical signals. Sinusoidal voltages between 10 kHz and 1 MHz and up to 3 V (RMS) from a function generator (HP33120, Hewlett Packard, Santa Clara, Calif.) were then applied to the electrode elements through co-axial cables, and fluid flow was started by pumping the sucrose/dextrose buffer through the inlet port using a digital syringe pump (Daigger, Wheeling, Ill.) at flow rates of 20, 40 or 80 $\mu$l/min. Cell kinetic behaviors were viewed by looking upwards through the chamber bottom with a Nikon (Melville, N.J.) TMD inverted microscope equipped with a Hamamatsu (Bridgewater, N.J.) CCD video camera and recorded on video tape. Long working length objective lenses of 4× to 40× provided final magnifications of between 140 and 1400 on the TV monitor. Cell velocities were analyzed by measuring the time taken for individual cells to move at least 120 $\mu$m ($\geq$3 electrode+gap periods). In cell levitation experiments, the fluid flow was stopped and heights of the cells above the electrode plane were measured to an accuracy ±2 $\mu$m by subtracting the corresponding readings on the focusing dial when focusing first on the electrode plane and then on the cells and correcting for the refractive index (1.33) of the suspending medium.

Experimental Results
DEP Levitation

FIG. 27 shows the typical frequency dependency of levitation height for HL-60 cells at a suspension conductivity of 56 mS/m for an applied voltage of 1.06 V (RMS). As the frequency of the voltage was increased from 2 to 30 kHz, the cell levitation height steadily rose. However, increasing the frequency above 30 kHz, led to a sharp drop off in levitation height until above 300 kHz the cell became trapped at the electrode edges. The levitation characteristics of other cell types including murine erythroleukemia DS19 and human breast cancer MDA-MB-231 cells (data not shown) exhibited qualitatively similar frequency dependencies except that the sharp transition from cell levitation to trapping occurred in characteristically different frequency ranges for each cell type. FIG. 28 shows the typical voltage dependency of HL-60 levitation at a frequency of 17.8 kHz. Clearly, the levitation height exhibited a sublinear, monotonic relationship to the applied voltage.

DEP-FFF Velocity

The effectiveness of applying DEP forces to control particle velocities in a fluid flow profile was studied by measuring the velocities of HL-60 cells in a DEP-FFF chamber as a function of the frequency and magnitude of the signals applied to the electrode array. It was not possible to measure these dependencies for single cells due to the impracticality of tracking them throughout an entire experiment. Instead, the velocities of about 20 individual cells chosen at random were determined for each experimental condition. FIG. 29 illustrates the frequency dependencies of the mean velocity of HL-60 cells for three different rates of fluid flow. Cells moved faster with increasing the flow rate, thus at an applied frequency of 17.8 kHz, the mean velocity increased from 77 (±4.1) to 292 (±32) $\mu$m/s as the flow rate was varied from 20 to 80 $\mu$l/min. The overall frequency dependency did not appear to change with the flow rate, and application of voltage signals caused HL-60 cells to move at either higher or smaller velocities. For a flow rate of 20 $\mu$l/min, in the applied frequency range of 10 to 50 kHz cell velocities were about four times higher than with no field applied. In the narrow frequency band from 100 to 300 kHz, cell velocities decreased sharply to those observed with no field applied. At 100 kHz, individual HL-60 cells exhibited vastly different velocities and fast-moving cells traveled five times faster than the slowest ones. Under these conditions, the variance of cell velocities was ~30% in contrast to ~10% for frequencies below 100 kHz. Increasing the field frequency above 300 kHz resulted in a further decrement in mean velocity to values much smaller than those observed in the absence of an electrical field. For example, at 1 MHz, the mean velocities were about 40% and 73% of the zero-field values for flow rates of 20 and 80 μl/min, respectively. For the small flow rate of 20 μl/min, some HL-60 cells were even trapped on electrode edges.

The voltage dependencies of the mean velocity are shown in FIG. 30 for HL-60 cells at a fixed frequency of 31.6 kHz for three different flow rates, and as in FIG. 29, increasing the flow rate led to aster cell elution. For a given flow rate, the mean velocity increased steadily with applied voltage.
Separation of HL-60 Cells from Peripheral Blood Mononuclear (PBMN) Cells Two approaches, namely DEP retention and DEP-FFF, were used to separate HL-60 cells from a mixture with PBMN cells using a parallel electrode chamber. The device was the same as in FIG. 26, except that it had dimensions of 375 μm (H)×150 mm (L)×24 mm (W) and electrode widths and spacings of 50 μm. Cell mixtures in the ratio of 1:5 for HL-60:PBMN cells (predominately lymphocytes) were prepared in isotonic sucrose/dextrose buffer containing $10^6$ HL-60 cells/ml at a conductivity 10 mS/m. About 250 μl of cell mixture was loaded into the chamber with a syringe for each separation experiment and cells were allowed to settle on to the electrode plane for about 20 s. For DEP retention, signals of 0.88 V (RMS) at 50 kHz were then applied to the electrode arrays while the sucrose/dextrose eluate buffer was pumped through the chamber at a flow rate of 160 μl/min. All HL-60 cells were trapped at the electrode edges whilst PBMN cells were carried away with the fluid and were collected at the chamber outlet. The voltage was then switched off to release the HL-60 cells which were subsequently collected.

For DEP-FFF, voltage signals of 25 kHz of 0.88 V (RMS) were applied to the electrode arrays and an eluate flow in the chamber was established at a rate 160 μl/min. Almost all the PB MN cells and HL-60 cells were levitated and were caused to move under the influence of the fluid. Using the significant difference in cell size as the basis for identification, it was observed that PB MN cells were levitated to higher positions and traveled at about twice as fast as HL-60 cells. Therefore PBMN cells were eluted from the chamber in about (15 min) half the time (26 min) taken by HL-60 cells and excellent separation was thereby obtained.

Conclusions

In this example, an inhomogeneous dielectrophoretic-levitation force acted to balance the homogeneous gravitational force, and provided an effective mechanism for controlling positions of cells and their corresponding velocities in a fluid flow profile. Cell velocities and their corresponding transit time across a DEP-FFF chamber directly reflected their individual dielectric characteristics and may be exploited for both characterization and separation purposes.

Using HL-60 cells in thin chambers equipped with parallel electrode arrays on their bottom walls, we demonstrated the validity of a theoretical model for DEP-FFF system. The cell levitation height and corresponding velocity in an eluate flow profile were shown to be very sensitive to cell dielectric properties. This ability is significant for biological and clinical problems where cell subpopulations having subtle differences must be separated. Finally, we demonstrated that HL-60 cells could be separated from normal PBMN cells using both DEP-FFF and DEP retention approaches.

We found that the electric field distribution critically determines the sensitivity of the dependence of cell levitation height, and thus traveling velocity, on cell dielectric properties.

EXAMPLE 6

Purging Human Breast Cancer Cells from CD34+ Stem Cells by Dielectrophoretic Field-Flow-Fractionation In this Example, the purging of cultured human breast cancer MDA-435 cells from $CD34^+$ cells using a dielectrophoretic-field flow fractionation (DEP-FFF) technique that separates cells according to cell dielectric properties is demonstrated. An array of interdigitated microelectrodes lining the bottom surface of a thin chamber was used to generate dielectrophoretic forces that levitated the cell mixture in a fluid flow profile. $CD34^+$ stem cells were levitated higher, were carried faster by the fluid flow, and exited the separation chamber earlier than the cancer cells. Using on-line flow cytometry, efficient separation of the cell mixture was observed in less than 12 min, and $CD34^+$ stem cell fractions with a purity >99.2% were obtained. The method of dielectrophoretic field-flow-fractionation is potentially applicable to many biomedical cell separation problems including microfluidic-scale diagnosis and preparative-scale purification of cell subpopulations.

Several important features of this Example include the following. First, there were two outlet ports on the chamber top and bottom plates. The separated cells exited the chamber from the bottom outlet port while the majority of the carrier medium exited the chamber from the top outlet port. Secondly, the separated cells were detected by on-line flow cytometry. Because of the two outlet port arrangement, the fluid pressure and flow rate at the flow cytometry were decreased but the concentration of the cells at the flow cytometry was increased compared with typical one outlet port arrangement such as those shown in FIGS. 13 and 26. Furthermore, this allows the separation being operated at relatively higher flow rates, that are not limited by the maximum flow rate at the flow cytometer. Thirdly, two separation protocols, namely, trap-and-release and sweep-frequency DEP-FFF have been explored, and their separation performance in terms of purity, speed and recovery rate have been examined. Each of the separation protocol consisted of several segments during which electrical signals of different amplitude, frequency or waveforms were applied to the microelectrode array.

Materials and Methods

Cell Preparation

MDA-435 cells, originally derived from a pleural effusion of a patient with metastatic breast cancer (Cailleau et al., 1978; Zhang and Fidler, 1991), were maintained under standard tissue culture conditions in minimum essential/F12 medium containing 10% fetal bovine serum (FBS), 1 mM glutamine, and 20 mM HEPES, plus 0.5% penicillin and streptomycin. The cells were harvested at 80% confluence 48 hr after seeding by a brief exposure to 0.25% trypsin/0.02% EDTA, washed once and re-suspended in a isotonic 8.5% (w/w) sucrose plus 0.3% (w/w) dextrose buffer at a concentration of 6×10⁶ cells/mL. The electrical conductivity of the sucrose buffer was adjusted to 10 mS/m with RPMI 1640 medium.

Mobilized peripheral blood samples were collected from leukapheresis products of patients after mobilization using rhG-CSF (Neupogen, Amgen Corp., Thousand Oaks, Calif.) at a dose of 5 µg/kg subcutaneously twice daily. Leukapheresis were performed using the COBE Spectra Version 4.7 cell separator (COBE BCT, Inc., Lakewood, Colo.) for mononuclear collection. $CD34^+$ cells were then obtained using magnetic-activated cell-sorting system with CD34 isolation kit according to the protocol provided by the company (Miltenyi Biotech). The purified $CD34^+$ (>99%) cells were washed once and re-suspended in a PBS buffer containing 2% FBS, 0.1% sodium azide at $2×10^7$ cells/ml. For flow cytometry detection, the $CD34^+$ cells were stained with phycoerythrin (PE) -conjugated CD34 antibodies (anti-HPCA-2, Becton Dickinson, San Jose, Calif.) by adding 20 µL antibody to every 50 µL cell-suspension and incubating the mixture for 30 min at 4° C. in dark. The labeled $CD34^+$ cells were then washed once and re-suspended in above sucrose buffer. The final cell mixtures were prepared by adding MDA-435 to $CD34^+$ cells in the sucrose buffer for a total concentration of $6×10^6$ cells/ml at a ratio of 1:1 for MDA-435 to $CD34^+$ cells.

DEP-FFF System Setup

The experimental DEP-FFF used in this Example is shown in FIG. 31. Interdigitated microelectrodes, 50 µm in width and gaps, were fabricated on 50×50 mm glass substrates using standard photolithography. Eight electrodes were glued end-to-end onto a supporting glass plate to form one electrode plate. The chamber was constructed by sandwiching a Teflon spacer (H 0.42×W 50×L 400 mm) between a top glass plate and the bottom electrode plate with 36 Nylon screw-clamps. The spacer was cut to provide an open channel with dimensions of 388 mm from tip to tip and 25 mm in width except at the tapered ends. The microelectrodes, each having two 4-mm wide electrical conductor buses along the edges, were connected in parallel to a lab-build power amplifier. The voltage signals were monitored on an oscilloscope. The top and bottom plates were drilled with 0.0625 in-diameter holes to fit inlet and outlet tubing at positions coincident with the points of the tapered ends of the chamber. A 5 cm length of PEEK tubing, having a void volume of 3 µL, served as the inlet connection between the chamber and an injection valve equipped with a 50 µL loop. A digital syringe pump was used to provide continuous flow of carrier medium through the chamber. At the outlet end, the cells exited the chamber through the tubing fitted to the bottom plate and were fed to a flow cytometer (BRYTE HS, Bio-Rad, Hercules, Calif.) for detection. To reduce the fluid pressure to the flow cytometer, a second syringe pump was connected to the tubing from the top-plate hole and was operated to pull 95% of the fluid out of the chamber.

DEP-FFF Operation Protocol

The DEP-FFF chamber was first loaded with the sucrose buffer. The cell mixture sample was then introduced into the inlet port of the chamber through the injection valve, as described previously (Wang et al., 1998). Total injection volume was 60 µL. Voltage signals (4 V p-p) at an appropriate frequency were applied to the electrodes during the sample introduction so that cells would be levitated in the chamber by the DEP forces, preventing possible adherence of the cells to the bottom surface of the chamber. After injection, cells were allowed 5 min to attain equilibrium heights at which the DEP and gravitational forces acting on them were balanced. Flow of the carrier medium at the rate of 2 mL/min through the chamber was then started using the syringe pump, and because of the geometrical characteristics, a parabolic hydrodynamic flow profile was established inside the chamber. Under the influence of the fluid drag, cells were transported at different velocities according to their relative positions in the flow profile. Cells exiting the chamber were detected by the flow cytometry. Four-parameter measurements were performed on individual cells, including time, fluorescence (PE filter set), and forward and side size scatter.

Two protocols of DEP field application were developed for the separation of MDA-435 and $CD34^+$ cell mixtures. In the trap-and-release DEP-FFF protocol, the DEP field was first applied for certain time at a frequency to trap MDA-435 cells at the electrodes but simultaneously to levitate and elute $CD34^+$ cells. The field was then changed to a frequency to release and elute the previously trapped MDA-435 cells. In the second protocol, the frequency of the DEP field was swept over a range repetitively to maximize the differences in equilibrium levitation heights (and thus the velocities) between MDA-435 and $CD34^+$ cells. After certain time, a single-frequency DEP field was applied to speed up the elution of all the cells.

Results

Cell DEP-FFF Responses

To determine separation conditions, DEP-FFF responses of MDA-435 and $CD34^+$ cells were studied separately as a function of the frequency of the applied field. FIGS. 32–33 shows the DEP-FFF fractograms for the two cell types at different frequencies. For MDA-435 cells at 10 kHz, cell elution spanned between 3 and 8 min and peaked at 6 min. With increasing frequency, the response was characterized by rapid broadening of the fractogram with no obvious elution peak observed at frequencies above 15 kHz. The total eluted cell number decreased at 20 kHz, indicating that some cells were trapped in the chamber by DEP forces. The cell trapping was confirmed by microscopic inspection of the chamber and by detecting cells when the frequency was switched back to 10 kHz. In contrast to MDA-435 cells, $CD34^+$ cells exhibited DEP-FFF fractograms having single and narrow peaks. Between 10 and 40 kHz, $CD34^+$ cells eluted the chamber from 4 to 7 min with peaks at ~4.5 min. With increasing frequency, the elution fractogram gradually broadened with the peak position shifted to ~8 min at 60 kHz.

To quantify these differences between MDA-435 and $CD34^+$ cells, two parameters were defined to describe the elution characteristics of the cells at different frequencies, namely, the elution time and the elution peak width. These parameters were determined from cell fractograms based on the integral of cell number with time, as described previously in Yang et al., 1999a. FIG. 34 shows the frequency dependency of these parameters for MDA-435 and $CD34^+$ cells, providing the information for choosing the DEP-field frequency range to promote the separation of these two types of cells. Both elution time and elution peak width increased much more rapidly with frequency for MDA-435 cells than $CD34^+$ cells, reflecting significant differences in their DEP-FFF responses.

Separation of MDA-435 Cells from $CD34^+$ Cells

Two separation protocols, namely, trap-and-release and sweep-frequency DEP-FFF, were developed. Following the introduction to the chamber, the cells were allowed 5 min to attain equilibrium height positions under a 10 kHz DEP-field prior to the initiation of the fluid-flow. In the trap-andrelease protocol, as the fluid-flow started, the DEP-field frequency was changed to 40 kHz at which CD34+ cells were levitated by DEP forces and transported under the influence of the fluid-flow, simultaneously, MDA-435 cells were trapped by DEP forces. This field condition was maintained for 7 min during which majority of CD34+ cells eluted the chamber. The DEP-field frequency was then switched to 5 kHz to allow the levitation and elution of the previously trapped MDA-435 cells. A typical fractogram for this separation is shown in FIG. 35, where the first and second peak corresponded to CD34+ and MDA-435 cells, as identified by the fluorescence measurement and size-scatter in flow cytometry. Flow cytometry detection further indicates that the CD34+ peak between 4.5 and 5.5 min contained 99.5% CD34+ cells, and 0.5% MDA-435 cells. MDA-435 peak between 9 and 12 min contained 96% MDA-435 cells and 4% CD34+ cell. In the sweep-frequency protocol, the DEP-field frequency was swept between 15 and 40 kHz repetitively at a 5 sec period when the fluid-flow was commenced. The sweep-frequency field was applied for 7 min. during which CD34+ cells were levitated and majority of them eluted the chamber whilst MDA-435 cells were levitated slightly and moved slowly through the chamber. As in the trap-and-release protocol, the frequency was then switched to 5 kHz to elute all the remaining MDA-435 cells. A fractogram for the separation is depicted in FIG. 36 showing that the separation was completed within 12 min and the elution-peak difference between the two cell types was >5 min. Flow cytometry detection further indicates that the CD34+ peak between 3 and 4 min contained 99.2% CD34+ cells, and 0.8% MDA-435 cells. MDA-435 peak between 7 and 10 contained 99% MDA-435 cells and 1% CD34+ cell.

A contour plot fluorescence vs. time for all the cells, as measured by the flow cytometry, is shown in FIG. 37. Clearly, CD34+ cells, having large fluorescence signals because of staining with CD34-PE, exited ahead of the unstained MDA-435 cells. The small cluster of unstained cells that exited before CD34+ cells were dead cell debris (based on smaller light scatter).

Discussion
Dependency of Cell DEP-FFF Responses on Their Membrane Dielectric Properties According to DEP-FFF theory, the balance between DEP levitation force and gravitational force positioned cells at equilibrium heights in the fluid-flow profile, and thus determined their velocities and elution times (Huang et al., 1997; Wang et al., 1998; Yang et al., 1999a). Cell elution time is a function of the voltage of the applied DEP-field, of an electrode geometry factor, and of cell dielectric polarization factor $\alpha_{DEP}$ and cell density. Since MDA-435 and CD34+ cells have similar cell densities, the difference in frequency dependencies of elution time (FIG. 34) between MDA-435 and CD34+ cells reflected their different $\alpha_{DEP}$ values. For CD34+ cells, the gradual-increase in elution time in the frequency range of 10 to 60 kHz indicated a steady-drop in the polarization factor $\alpha_{DEP}$. On the other hand, elution time for MDA-435 cells increased rapidly with frequency, suggesting a sharp decrease in $\alpha_{DEP}$.

To confirm these, cell dielectric properties were determined from electrorotation (ROT) measurements. In ROT, cells were subjected to a rotating electrical field and were induced to rotate as a result of the interaction between field-induced polarization and the rotating field. Cell rotational rate was measured as a function of the field frequency (FIG. 38A) and the spectra were fined with appropriate models to derive cell dielectric parameters. The frequency dependency of aDEP, calculated using the mean dielectric parameters (Table 1), is given in FIG. 38B for MDA-435 and CD34+ cells. Between 5 and 40 kHz, REP varied from −0.5 to −0.3 for CD34+ cells. On the other hand, $\alpha_{DEP}$ changed from −0.4 to 0 between 5 and 15 kHz for MDA-435 cells. These results are in general agreement with the above discussion regarding the frequency dependency of $\alpha_{DEP}$ for the two cell types.

It is well established that the dielectric polarization factor $\alpha_{DEP}$ below several hundred kHz is determined by the cell membrane electrical properties (Wang et al., 1994; Pethig and Kell, 1987; Arnold and Zimmerman, 1988). Indeed, the observed difference in $\alpha_{DEP}$ between MDA-435 and CD34+ cells is related to their different membrane capacitances (10.7 and 23.0 mF/m$^2$ for CD34+ cells and MDA-435, respectively). Thus the DEP-FFF separation of MDA-435 and CD34+ cells described here exploited the difference between their membrane dielectric properties.

Another important difference in DEP-FFF responses between the two cell types is the large elution-peak-width for MDA-435 cells at 20 kHz (FIG. 34), as evidenced by the broad elution fractogram (FIGS. 32–33). The elution peak widths depended on these factors. The elution time for individual cell depended on its velocity and travel distance through the DEP-FFF chamber. Since it was not possible to ensure that all the cells were positioned the same distance from the chamber outlet port during sample loading, a small spread (<10%) in elution time was expected even for the cells having the same velocity. Secondly, different cells of the same type exhibited different velocities because of inherent population heterogeneity in the cell dielectric parameters (see Table 1 for standard deviations of dielectric parameters). Indeed, at 15 kHz, $\alpha_{DEP}$ for MDA-435 cells was around zero, and small variations in $\alpha_{DEP}$ could lead to significant difference in cell velocity (and thus elution time) between individual cells because of the extreme sensitivity of cell velocity for small $\alpha_{DEP}$ values. Thus, the widespread of the elution fractogram for MDA-435 cells at 15 kHz was related to the heterogeneity in their dielectric properties.

Flow Cytometry Detection of Cells

Individual cells exiting the chamber were analyzed using a flow cytometer and cell elution fractogram was constructed. To operate DEP-FFF separation at a high flow rate (>0.1 mL/min, the maximum flow rate for the cytometer) and achieve an increased cell concentration at the cytometer, a second outlet port was introduced at the top plate of the chamber to elute cell suspension buffer. In such a configuration, it is important to ensure that no cells elute from the top outlet port by varying the flow rates at the inlet and outlet ports. Under a typical operating condition, a syringe pump drove the fluid flow in the chamber from the inlet port at a flow rate 2 mL/min. A second syringe pump was operated at 1.8 mL/min, pulling the fluid out of the chamber from the top outlet port. Thus, only 10% of the fluid, corresponding to a height of 80 $\mu$m in the parabolic flow profile from the chamber bottom, was eluted into the cytometer. The maximum equilibrium heights for individual MDA-435 and CD34+ cells measured under light microscope for a slow rate (10 $\mu$L/min) were less than 65 $\mu$m. Thus, no cells exited from the top outlet port. This was further confirmed experimentally, as the total cell number detected by the cytometer for such a 10% elution was the same as that for a 20% elution.

Separation Approaches

Separation between cell populations using DEP-FFF approach exploits differential cell velocities. According to FIG. 32, all the CD34+ cells eluted the DEP-FFF chamber in <10 min at 40 kHz, whilst <10% of MDA-435 cells eluted the chamber at the time 12 to 18 min. Thus, separation of the two populations can be achieved at 40 kHz. Indeed, as shown in FIG. 38B, the DEP mean crossover frequencies were found to be 10 kHz and ~60 kHz for MDA-435 and CD34+ cells, respectively. Thus, at 40 kHz, MDA-435 cells experienced positive DEP forces, tending to trap them at the electrode edges, whilst CD34+ cells were still levitated by negative DEP forces and released. After all the CD34+ cells were eluted, the frequency of the voltage signals were changed to 5 kHz to cause a fast elution of the MDA-435 cells in the chamber. Thus, the inventors effectively programmed the DEP field condition in order to improve the separation performance. And as MDA-435 cells were "trapped" and "released" in the two time segments of the DEP field application, the inventors termed this approach trap-and-release protocol.

While the trap-and-release protocol achieved a desired separation between the two populations, a disadvantage associated with this is that during the "trap" voltage segment, many MDA-435 cells were trapped on the electrode edges. Such a direct cell-electrode contact may not be ideal for certain applications. For example, cells may nonspecifically bind to the electrodes, and are not eluted even if a negative DEP force is applied. Also, MDA-435 cells may experience large AC field as a result of a direct cell-electrode contact. Furthermore, because of cell heterogeneity, some MDA-435 cells adhered to electrodes whilst others were caused to move under the fluid flow. Thus a large spread-out may occur during the application of the "trap" voltage segment. Such a spread out would result in a broadening of the final elution peak for MDA-435 cells.

For these reasons, a sweep-frequency protocol was developed. Thus, a signal having a fixed voltage and linearly sweeping frequency (10 to 40 kHz) was applied. Under the application of such a DEP field, CD34+ cells were eluted very similarly to the condition of a fixed 10 kHz. On the other hand, such a signal, effectively averaging DEP force across the sweep-frequency-band, should greatly reduce the number of the MDA-435 cells being trapped at the electrodes, and allow most MDA-435 cells slightly levitated and moved slowly under the influence of the fluid flow. Furthermore, because of the force averaging, large differences in kinetic responses between individual MDA-435 cells observed during single "trap" frequency application should be reduced, leading to a small spread out. After all the CD34+ cells were eluted, the voltage signals were switched to a lower frequency, at which MDA-435 cells were levitated and eluted (with tight and clean elution peaks).

TABLE 1

Dielectric Parameters for MDA-435 and CD34+ Cells

| Cell Type | $C_{specific}$, mF/m² | $\sigma_{int}$, S/m | $\epsilon_{int}$ |
|---|---|---|---|
| MDA-435 | 23.0 ± 7.1 | 0.55 ± 10.10 | 107.0 ± 29.5 |
| CD34+ | 10.2 ± 1.5 | 0.71 ± 0.11 | 141.2 ± 28.0 |

EXAMPLE 7

Dielectrophoretic field-flow-fractionation (DEP-FFF), which exploits differences in cell dielectric properties, was applied to several clinically-relevant cell separation problems. These included the purging of human breast cancer cells from normal T-lymphocytes, the separation of the major leukocyte subpopulations, and the enrichment of leukocytes from blood. Cell separations were achieved in a thin chamber equipped with a microfabricated, interdigitated electrode array on its bottom wall that was energized with AC electric signals. Cells were levitated by the balance between DEP and sedimentation forces to equilibrium heights that were dependent on cell density and dielectric properties. When carrier medium was flowed through the chamber, the resulting flow velocity profile transported cells that had been levitated to different heights at different velocities and thereby separated them. Cell separations achieved by DEP-FFF were evaluated by on-line flow cytometry, revealing high separation performances. For example, for a starting mixture of 2:3 for breast cancer cells:T-lymphocytes, DEP-FFF separation produced fractions of the two populations having purities of 99.2% and 92%, respectively. This bulk-separation technique adds dielectric properties to the catalog of physical characteristics that can be applied to cell discrimination. It is applicable not only to existing clinical and biomedical cell separation problems but also to the sample preparation needs of microfluidic devices for diagnostic and environmental detection purposes.

Materials and Methods

Cell Preparation

Human breast cancer MDA-435 cells were cultured in MEM supplemented with 10% fetal bovine serum under standard tissue culture conditions (Becker 1995; Wang et al 1994). Leukocyte subpopulations (T-, B-lymphocytes, monocytes and granulocytes) were derived from buffy coat preparations (Gulf Coast Regional Blood Bank, Houston, Tex.) using density-gradient centrifugation, MACS sorting and erythrocyte lysis, as described previously (Yang et al, 1999a). To allow for flow cytometry detection of the cells eluted from DEP-FFF chamber, B-lymphocytes, and monocytes were labeled with PE- or FITC-conjugated CD3, and CD14 antibodies (Becton Dickinson, San Jose, Calif.), respectively, by incubating the cell suspension with the antibody solution (volume ratio 5:2) for 30 min at 4° C. in the dark. Labeled cells were then washed once and re-suspended in an isotonic buffer (8.5% w/v sucrose plus 0.3% w/v dextrose) buffer having an electrical conductivity of 10 mS/m, which was adjusted by adding culture medium. Appropriate cell populations were then mixed in the sucrose buffer. Cell mixtures included MDA-435 cells with T-lymphocytes, B-lymphocytes with monocytes. The final cell concentration was $1.2 \times 10^6$/mL.

For DEP-FFF enrichment of leukocytes from blood, human blood was taken from healthy volunteers and stained with PE-CD45 antibody solutions to label leukocytes. The cell samples were then diluted in the isotonic sucrose buffer to achieve the final cell concentration ~$5 \times 10^6$/mL.

DEP-FFF System Setup

The DEP-FFF chamber and experimental setup are shown in FIG. 39. Interdigitated microelectrodes having 50 μm width and spacing were fabricated on 50×50 mm glass substrates using standard photolithography. A Teflon spacer, which was cut in the center to provide a separation channel (H 0.42×W 25×L 388 mm), was sandwiched between a top glass plate and a long electrode plate (consisting of eight electrode substrates in series). The microelectrodes were connected in parallel to a lab-built PA05-based power amplifier (Apex Microtechnology, Tucson, Ariz.). The top and bottom plates were drilled with 1.6-mm-diameter holes to fit inlet and outlet PEEK tubing (0.0625 in. OD, 0.010 in. ID, Upchurch Scientific, Oak Harbor, Wash.). An infusion syringe pump (Daigger, Wheeling, Ill.) was connected to the chamber through an injection valve (Rheodyne Model 7010, Rheodyne, Cotati, CA) equipped with a 50-μL loop to provide continuous flow of the carrier medium in the chamber. A second syringe pump was connected to the top outlet port of the chamber and was operated to withdraw the cell-free portion of the carrier fluid that constituted up to 95% of the total flow through the chamber. Cells exited the chamber through the bottom outlet port and were fed directly to the injection needle of a flow cytometer (BRYTE HS, Bio-Rad, Hercules, Calif.) for detection, bypassing the normal cytometer sample handling fluidics.

DEP-FFF Operation Protocol

The DEP-FFF chamber was first loaded with sucrose buffer. An aliquot of the cell mixture (50 $\mu$L) was then introduced into the inlet port of the chamber through the injection valve, as described previously (Wang et al, 1998). A DEP signal (4 V p-p) at 10 kHz was applied to the electrodes during sample injection so that cells were levitated in the chamber by DEP forces and thereby prevented from adhering to the bottom surface of the chamber. Different operation protocols were then applied for separating different cell mixtures after sample injection. The protocols for separating MDA435 cells from T-lymphocytes consisted of the following steps:

(1) Prior to the application of the fluid flow, a 10 kHz field was applied for 10 min to allow the cells to reach their equilibrium height positions.

(2) A flow velocity profile was established in the chamber by starting the injection and withdrawal syringe pumps at rates of 2 and 1.6 mL/min, respectively. The DEP field was switched to 40 kHz (or swept between 15 and 35 kHz at a cycle period of 5 sec). This condition was maintained for 5 or 7 min so that all the T-lymphocytes were eluted from the chamber and identified and counted by the on-line flow cytometer.

(3) The DEP field was changed to 5 kHz so that the previously retained MDA-435 cells were now levitated, eluted from the chamber and detected by the flow cytometer.

For separating other cell mixtures, different DEP field conditions were applied during the $2^{nd}$ segment of the protocol and are summarized in Table 1.

Results

Separation of Breast Cancer Cells from Normal T-lymphocytes

The isolation and enumeration of cancer cells circulating in peripheral blood is potentially an important screening tool for early detection of cancer and allows for the genetic and biochemical characterization of cancer cells for diagnosis and prognosis. Current methods, which can detect one cancer cell per ~$10^6$ mononuclear cells, involve separation of mononuclear cells from the blood, enrichment of cancer cells, and finally flow cytometric or PCR detection. To demonstrate the usefulness of the dielectrophoretic approach to this problem, we investigated the DEP-FFF separation of cultured, human breast cancer MDA-435 cells from T-lymphocytes, which constitute approximately 80% of peripheral blood mononuclear cells.

Cell dielectric properties and DEP behaviors depend sensitively on the frequency of the applied electrical field (Becker et al, 1995; Fuhr et al, 1996; Pethig, 1996; Gascoyne et al, 1997). Therefore, to establish suitable cell separation conditions, we measured the DEP-FFF responses of breast cancer cells and T-lymphocytes separately as a function of frequency. FIG. 40 shows cell elution fractograms for the two populations. While both cell types exhibited narrow, single elution peaks at 5 kHz, the fractogram for the breast cancer cells quickly broadened as the field frequency was increased above 10 kHz. At 20 kHz, only ~35% of the breast cancer cells were eluted; the rest were retained in the chamber by positive DEP forces. In contrast, the elution peak width for T-lymphocytes changed more gradually, and almost all were eluted at frequencies up to 50 kHz. These differences suggested that the two cell types should be separable at frequencies between 20 and 50 kHz.

To examine this possibility under demanding conditions, we prepared a cell mixture at a ratio of 2:3 (breast cancer:T lymphocyte) at a concentration of $1.2 \times 10^6$ cells/mL and applied DEP field frequencies around 30 kHz. As the DEP-FFF fractograms in FIG. 41 show, the mixture was separated in 11 min and purities above 92% for the two populations, and a total cell recovery of ~70% were achieved (Table 2). The separation occurred because at frequencies around 30 kHz, T-lymphocytes were levitated well above the chamber bottom wall by DEP forces and transported under the influence of the fluid flow. Meanwhile, breast cancer cells were either barely levitated (and, therefore, carried slowly by the slower-moving fluid near the chamber bottom wall) or were trapped at the electrodes and immobilized by positive DEP forces. After T-lymphocytes were eluted from the chamber, DEP field was switched to 5 kHz and breast cancer cells were then levitated and quickly eluted.

Separation of the Major Leukocyte Subpopulations

Purification of major leukocyte subpopulations (i.e. T- and B- lymphocytes, monocytes and granulocytes) is important in many clinical and biomedical applications. The differential diagnosis of bacterial, viral and parasitic infections, and of mononucleosis and leukemia, for example, require the enumeration of leukocyte subtypes. In research, purified leukocyte subpopulations are required for the study of molecular signaling between leukocyte subpopulations by the interleukins and for the analysis of immunological capacities of distinctive cell types.

The major leukocyte subpopulations have significantly different dielectric properties (Yang et al, 1999b). To determine the feasibility of purifying them by DEP-FFF, we mixed T- (or B-) lymphocytes with monocytes, T- (or B-) lymphocytes with granulocytes, and monocytes with granulocytes. To illustrate the DEP-FFF separations, we will consider the mixture of B-lymphocytes and monocytes, which was typical of all the blood cell mixtures. To obtain these cells, B-lymphocytes and monocytes were purified from a leukocyte-enriched buffy-coat preparation using the MACS method (Yang et al, 1999b). The DEP-FFF characteristics of the individual cell subpopulations suggested that a swept frequency field between 25 and 45 kHz would be a suitable separation condition and this was applied for DEP-FFF to a cell mixture (1:2 for monocytes:B-lymphocytes) at a total concentration of $1.2 \times 10^6$ cells/mL. A typical DEP-FFF fractogram is shown in FIG. 42 under these conditions. DEP-FFF separation resulted in monocyte and B-lymphocyte fractions having purities of 94% and 92%, respectively (Table 2).

Enrichment of Leukocytes from Blood

Separation of erythrocytes and leukocytes from blood, typically performed using centrifugation or filtration, is a basic requirement for many biomedical procedures such as erythrocyte transfusion. We therefore attempted to use DEP-FFF to enrich leukocytes (and erythrocytes) from blood diluted 1:1000 in a sucrose buffer. Based on the DEP-FFF characteristics of erythrocyte and leukocyte subpopulations, a DEP field at 10 kHz was applied for DEP-FFF. A typical fractogram is shown in FIG. 43, leukocytes were enriched 35-fold and erythrocyte purity was increased from 99.8% in the blood sample to >99.99% in the final erythrocyte fraction. In this case, we believe that the differential cell velocities exploited in the DEP-FFF separation arose not only from levitation height differences between leukocytes and erythrocytes but also from differences in cell-hydrodynamic interactions caused by different cell shapes since erythrocytes are double-discoid while leukocytes are generally round.

DEP-FFF separation of the two populations. It follows that cell membrane dielectric properties, determined by membrane composition and morphological structures (Wang et al, 1994; Huang et al, 1999), were DEP-FFF separation criteria exploited here.

Over the last 15 years, the dielectric properties of many normal and cancerous cell types have been shown to be

TABLE 2

DEP-FFF separation performance summary

| Experimental systems (Protocol)[a] | Cell types | Purity after separation[d] | Total-cell recovery[f] | Separation time (min) |
|---|---|---|---|---|
| MDA-435 vs T-lymphocytes (2:3)[b] (40k Hz, 5 min; 2/1.6 mL/min)[a] | MDA-435 T-lymphocytes | 99.2% 92% | 69% | 11 |
| MDA-435 vs T-lymphocytes (2:3)[b] (15–35 kHz, 5 min; 2/1.6 mL/min)[a] | MDA-435 T-lymphocytes | 98% 92% | 75% | 11 |
| Monocytes vs B-lymphocytes (1:2)[b] (20–40 kHz, 7 min; 2/1.9 mL/min)[a] | Monocytes B-lymphocytes | 94% 92% | 73% | 15 |
| Enrichment of leukocytes from blood (10 kHz, 25 min; 0.5/0.4 mL/min)[c] | Leukocytes Erythrocytes | 5%[e] 99.99% | 55% | 25 |

[a]Single frequency or swept frequency (cycle period 5 s) of DEP-field used during the $2^{nd}$ segment of the protocol (see Materials and Methods). The two flow rates correspond to the infusion and withdrawal syringe pumps at the chamber inlet and outlet ends, respectively.
[b]The ratio between the two cell populations in initial mixtures.
[c]The enrichment of leukocytes from blood used a DEP field at 10 kHz for 25 min.
[d]Purity after separation was determined by the flow cytometry for the corresponding elution peaks.
[e]Leukocyte to erythrocyte ratio was increased from 1:700 to 1:19 after DEP-FFF enrichment.
[f]Cell recovery was defined as the ratio of the total cell number detected by flow cytometry at the DEP-FFF chamber outlet end to the targeted total cell number that was calculated based on the cell concentration and the injection loop volume.

Discussion
Cell Dielectric Separation Criteria

The DEP-FFF method exploits cell dielectric and density properties as the basis of separation. In the frequency range used for the separations described here, cell dielectric properties are determined by the extent to which the applied field penetrates the cell interior via the capacitance of the plasma membrane. At low frequencies, the field penetration is small and the entire applied field appears across the poorly-conducting membrane. Thus, cells are less polarizable than the suspending medium and tend to be repelled from strong electrical field regions by negative DEP forces. In our electrode configuration, this causes levitation. At higher frequencies, the field penetrates the plasma membrane into the cell interior, which is more conductive than the suspending medium under our conditions. Cells become more polarizable than the medium, the DEP forces become positive, and cells are attracted to the strong field regions and immobilized at the electrodes (Becker et al, 1995; Fuhr et al, 1996; Kaler & Jones, 1990; Pethig 1996). Take breast cancer MDA-435 cells and T-lymphocytes as an example. Because of differences in cell membrane morphology and composition, T-lymphocytes have a mean membrane capacitance approximately half that of breast cancer cells (Gascoyne et al, 1997; Huang et al, 1996; Huang et al, 1999), and the frequency range in which sufficient field penetration occurred for the DEP force to become positive was therefore higher for T-lymphocytes. Thus in the frequency range from 15 to 35 kHz, T-lymphocytes were strongly levitated by negative DEP forces and were transported quickly through the chamber under the influence of the fluid flow. Breast cancer cells, however, were only weakly levitated into the slow moving fluid close to the chamber bottom wall or were trapped by positive DEP forces at the electrodes. The differential velocities for T-lymphocytes and the breast cancer cells resulted in the distinct and to depend not only on cell type but also on the biological state. For this reason, we have introduced the concept of cell dielectric phenotype (Becker et al, 1995; Gascoyne et al, 1997). The dielectric phenotypes of T-lymphocytes allow them to be distinguished from breast cancer cells, monocytes and granulocytes, and leukemia cells can be distinguished from normal leukocytes. Other examples include significant membrane dielectric alterations accompanying temperature-sensitive transformation of rat kidney cells (Huang et al, 1996), drug-induced differentiation in leukemia cells (Wang et al, 1994), mitogenic stimulation of human lymphocytes (Huang et al, 1999), fertilization of rabbit oocytes (Arnold et al, 1989), and changes in cell environment such as exposure to heavy metals (Arnold et al, 1986), organic toxins (Arnold, 1988), or hypo-osmotic media (Sukorukov, 1993). These examples suggest that by exploiting such dielectric phenotypes, the DEP-FFF technique may be applied for discrimination, characterization and separation of cell subpopulations in many biomedical problems.

It is contemplated that the apparatus and methods according to the present invention may be used for cell or particle characterization, as a diagnostic tool to identify, for example, cancer cells or other cells that are desired or of interest to the clinician, and as a therapeutic tool to purge a patient sample of undesired cells or other particle.

For example, the methods according to the present invention may be used to characterize the physical properties of an unknown particulate matter. A sample including an unknown biological or organic or mineral sample may be input into the chamber and separated according to the procedures set forth above. Following separation and removal of extraneous particles, the unknown particle may be collected at an output port of the chamber. The particle can then be analyzed using standard particle characterization techniques known in the art, such as those used in diagnostic microbiology and in histology, for example, electron microscopy. After determining characteristics that are unique to a particle, an investigator may then compare these characteristics to the known characteristics of a particle. Therefore, the researcher may determine whether the unknown particle is the same as a known particle, or whether it has similar properties.

In addition, the invention contemplates the characterization of known particles, which may then be used as a reference tool for determining unknown particles based on similar trapping frequencies, voltages, flow rates, and other parameters set forth above. The sample may be introduced into the chamber of the present invention and then be subjected to the separation methods detailed above. By performing these separation techniques, the trapping frequency and release frequency of the particle can be determined. These values are then useful in comparing similar parameters of an unknown sample to this known sample. Certain clinical applications requiring separation of a known particle from an unknown particle would require such values to complete the methods of separation.

A clinical application of the present invention would be to use the present apparatus and methods as a diagnostic tool to screen unknown samples for the presence or absence of various cell types. First, as set forth previously, a patient's sample may be placed in the apparatus, and various cell types may be separated based on previously determined parameters or characteristics. These cells may include cancer cells, or cells infected with bacteria, viruses, protozoans, or parasites, bacteria, viruses protozoans, or they may include cells that are deficient in certain enzymes or cell organelles, altered biopsies, plaques and scrape tests including Pap smears and so forth. Thus, it is well within the scope of the invention to separate all types of particles that have differential sedimentation rates in a fluid stream, based on size, density, dielectric strength, and conductivity, for example. Therefore, the present invention may be used to diagnose the presence of a condition, for example, a cancer, or other cellular disorder.

Another clinical application would be to use the apparatus and methods of the present invention to separate unwanted cells, such as cancerous cells, from a cell population including wanted or normal cells. For example, once a cancer has been detected, for instance in bone marrow, a patient's bone marrow may be input into an apparatus according to the present invention to separate the cancer cells, or preneoplastic cells, from normal cells. These normal cells may then be collected at the output of the chamber and returned to the patient, while the unwanted cancer cells may be later collected at the output of the chamber and characterized, utilized in further studies, or discarded. In this manner, unwanted cells are purged from a normal cell population, while at the same time a particular cell type is enriched, such as tumor cells, normal cells, progenitor cells, etc.

The apparatus and methods disclosed and claimed herein can be made and executed without undue experimentation in light of the present disclosure. While the apparatus and methods of this invention have been described in terms of preferred embodiments, it will be apparent to those of skill in the art that variations may be applied to the apparatus, methods and in the steps or in the sequence of steps of the method described herein without departing from the concept, spirit and scope of the invention. All substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Arnold, W. M. and Zimmermann U. (1982) *Naturwissenischaften*, 69,297–300.
2. Arnold, W. M. et al. 1986. *Biochim. Biophys. Acta.* 889, 35–48.
3. Arnold, W. M. & Zimmermann, U. (1988) *J. Electrostat.* 21, 151–191.
4. Arnold, W. M. et al. 1988. *Biochim. Biophys. Acta.* 942, 83–95.
5. Arnold, W. M. et al.1989. *Biochim. Biophys. Acta.* 979, 142–146.
6. Becker, F. F. et al. (1994) *J. Phys. D: Appl. Phys.* 27(12), 2659–2662.
7. Becker, F. F. et al. (1995) *Proc. Natl. Acad. Sci.* 92, 860–864.
8. Boyum, A. (1974) *Tissue Antigens* 4, 269–274.
9. Cailleau, R.;Olive, M.; Cruciger, Q. V. J. *In Vitro* 1978, 14, 911–915.
10. Cantrell, D. A. et al. (1992) *Ciba. Found Symp.* 164, 208–222.
11. Chess, L. et al. (1976) in: *In vitro Methods in Cell Mediated and Tumor Immunity*, 255–261.
12. Fischer, A. (1993) *Brit. J. Haematol.* 83, 531–534.
13. Fuhr, G. (1985) Über die rotation dieelektrischer korper in rotierenden feldern, PhD. Dissertation, Humboldt-Universit_t, Berlin, Chap. 3, 24–53.
14. Fuhr, G.; Hagedorn, R. (1996) In *Electrical Manipulation of Cells*; Lynch, P. T., Davey, M. R. Eds.; Chapman & Hall: New York. pp 37–70.
15. Fuhr, G. et al. (1996) in *Electromanipulation of cells*, Zimmermann, U. and Neil, G. A. (eds.). CRC Press, Boca Raton, Fla. pp259–328.
16. Gascoyne, P. R. C. et al. (1994) *IEEE. Trans. Ind. Appl.* 30, 829–834.
17. Gascoyne, P. R. C., et al. (1992) *Meas. Sci. Technol.* 3, 439–445.
18. Gascoyne P. R. C. et al 1996. *Biophys. J.* 70: A330.
19. Gascoyne, P. R. C.; et al. (1997) *IEEE Trans. Ind. Appl. Soc.*, 33, 670–678.
20. Giddings, J. C., (1993) *Science* 260, 1456–1465.
21. Hagedom, R. et al. (1992) *Electrophoresis* 13, 49–54.
22. Holzel, R. and Lamprecht I. (1992) *Biochim. Biophyus. Acta* 1101, 195–200.
23. Huang, Y. et al. (1992) *Phys. Med. Biol.* 37, 1499–1517.
24. Huang, Y. et al. (1993) *Phys. Med. Biol.* 37, 1499–1517.
25. Huang, Y. et al. (1996) *Biochim. Biophys. Acta* 1282, 76–84.
26. Huang, Y. et al. (1997) *Biophys. J.* 73, 1118–1129.
27. Huang, Y. et al. (1999) *Biochim. Biophys. Acta* 1417, 51–62.
28. Irimajiri, A. et al. (1979) *J. Theor. Biol.* 78, 251–269.
29. Kakutani, T. et al. (1993) *Bioelectrochem. Bioenerg.* 31, 131–145.
30. Kaler, K. V. I. S. amd Jones T. B. 1990. *Biophys. J.* 57, 173–182.
31. Liu L-K., et al. (1991) *Anal. Chem.* 63, 2115–2122.
32. Markx, G. H. et al. (1994) *Microbiology* 140,585–591.
33. Pazourek J. & Chmelik J. (1992) *J. Chromatography,* 593, 357–362.
34. Pethig, R. (1996). *Crit. Rev. Biotechnol.* 16, 331–348.
35. Pethig, R.; Kell, D. B. (1987) *Phys. Med. Biol.* 32, 933–970.
36. Smeland, E. B. et al. (1992) *Leukemia*, 6, 845–852.
37. Schwan H. P. (1992) *Ann. Biomed. Eng.* 20, 269–288.
38. Stout, R. D. (1993) *Curr. Opin. Immunol.* 5(3), 398–403.
39. Sukorukov, V. L., et al. (1993) *J. Membrane Biol.* 132, 27–40.
40. Talary M, et al. (1995) *Med. Biol. Eng. Comp.* 33, 235–237.

41. Wang, X.-B. et al. (1993) *J. Phys. D: Appl. Phys.* 26, 1278–1285.
42. Wang, X.-B. et al. (1994) *Biochim. Biophys. Acta* 1193, 330–344.
43. Wang, X.-B. et al. (1995) *Biochim. Biophys. Acta* 1243, 185–194.
44. Wang, X., et al. (1996) *J. Phys. D: Appl. Phys.* 29, 1649–1660.
45. Wang, X.-B. et al.(1997). *IEEE Trans. Ind. Appl.* 33, 660–669.
46. Wang, X.-B. et al. (1998) *Biophys. J.* 74, 2689–2701.
47. Williams P. S., et al (1992) *Chem. Eng. Comm.* 111, 121–147.
48. Yang J. et al. (1999a) *Anal. Chem.* 71, 911–918.
49. Yang J., et al. (1999b) *Biophys. J.* 76, 3307–3314.
50. Zhang, R. D. & Fidler, I. J. (1991) *Invasion Metastasis* 11, 204–211.

What is claimed is:

1. A method of discriminating matter in a chamber having an inlet port and an outlet port, said chamber defined by a pair of side walls, a top wall and a bottom wall, and an electrode element adapted to said chamber, said chamber having a substantially greater width than thickness, utilizing dielectrophoresis and field flow fractionation, comprising:
   introducing a carrier medium including said matter into said inlet port and directing said carrier medium from said inlet port to said outlet port, such that said carrier medium travels through said chamber according to a velocity profile;
   applying a programmed voltage signal to said electrode element to create a spatially inhomogeneous electric field which causes a dielectrophoretic force on said matter having components normal to the direction of said carrier medium traveling through said chamber; and
   controlling said spatially inhomogeneous electric field to balance said dielectrophoretic force with a gravitational force on said matter to displace said matter to positions within said velocity profile in said carrier medium to discriminate said matter.

2. The method of claim 1, wherein said programmed voltage signal comprises a time dependent amplitude or frequency.

3. The method of claim 1, wherein said programmed voltage signal comprises frequency modulation.

4. The method of claim 1, wherein said programmed voltage signal comprises amplitude modulation.

5. The method of claim 1, wherein said programmed voltage signal comprises a sweeping frequency.

6. The method of claim 1, wherein said programmed voltage signal comprises a series of voltage signals, said voltage signals having different waveforms.

7. The method of claim 6, wherein said different waveforms differ in signal frequency, signal amplitude, frequency modulation, or amplitude modulation.

8. The method of claim 1, wherein said matter travels through said chamber at a velocity proportionate to its displacement within said velocity profile.

9. The method of claim 1, wherein said matter exits from said outlet port at time intervals proportionate to its displacement within said velocity profile.

10. The method of claim 1, wherein said matter exits from said outlet port at positions laterally displaced from said inlet port.

11. The method of claim 1, wherein said method of discriminating matter is in continuous mode.

12. The method of claim 1, wherein said method of discriminating matter is in batch mode.

13. A method of discriminating matter, utilizing dielectrophoresis and field flow fractionation, in a chamber having an inlet port and an outlet port, said chamber defined by a pair of side walls, a top wall and a bottom wall, and an electrode element adapted to said chamber, said chamber having a substantially greater width than thickness, comprising:
   introducing a carrier medium from said inlet port into said chamber;
   introducing said matter into said inlet port;
   introducing a transport fluid into said inlet port and directing said transport fluid from said inlet port to said outlet port, such that said transport fluid travels through said chamber according to a velocity profile;
   applying a programmed voltage signal to said electrode element to create a spatially inhomogeneous electric field which causes a dielectrophoretic force on said matter having components normal to the direction of said transport fluid traveling through said chamber; and
   controlling said spatially inhomogeneous electric field to balance said dielectrophoretic force with a gravitational force on said matter to displace said matter to positions within said velocity profile in said transport fluid to discriminate said matter.

14. The method of claim 13, wherein said matter travels through said chamber at a velocity proportionate to its displacement within said velocity profile.

15. The method of claim 13, wherein said matter exits from said outlet port at time intervals proportionate to its displacement within said velocity profile.

16. A method of discriminating matter utilizing dielectrophoresis and field flow fractionation in a chamber defined by a pair of side walls, a top wall, and a bottom wall, said method comprising:
   introducing a carrier medium including said matter into an inlet port of said chamber and directing said carrier medium from said inlet port toward top and bottom outlet ports coupled to said top and bottom walls, respectively;
   applying an electrical signal to an electrode element coupled to said chamber to create a spatially inhomogeneous electric field to generate a dielectrophoretic force on said matter having components normal to the direction of said carrier medium traveling through said chamber;
   controlling said spatially inhomogeneous electric field to balance said dielectrophoretic force with a gravitational force on said matter to displace said matter to different heights within said chamber to discriminate said matter;
   withdrawing a first portion of said carrier medium from said top outlet port; and
   withdrawing a second portion of said carrier medium from said bottom outlet port.

17. The method of claim 16, wherein at least a portion of said matter is withdrawn from said top outlet port.

18. The method of claim 16, wherein at least a portion of said matter is withdrawn from said bottom outlet port.

19. The method of claim 16, wherein said carrier medium is introduced into said inlet port at a first fluid flow rate, and wherein said first portion is withdrawn at a second fluid flow rate, said second fluid flow rate being less than or equal to said first fluid flow rate.

20. The method of claim 16, wherein said carrier medium is introduced into said inlet port at a first fluid flow rate, and wherein said first portion is withdrawn at a second fluid flow rate equal to about one half of said first fluid flow rate.

21. The method of claim 16, wherein said first portion is withdrawn at a first fluid flow rate and wherein said second portion is withdrawn at a second fluid flow rate.

22. The method of claim 21, further comprising varying said first and second fluid flow rates to reduce fluid pressure of at least one of said top or bottom outlet ports.

23. The method of claim 21, further comprising varying said first and second fluid flow rates to further discriminate said matter.

24. The method of claim 16, wherein said first portion or said second portion is withdrawn with a syringe pump.

25. The method of claim 16, wherein said method of discriminating is in continuous mode.

26. The method of claim 16, wherein said method of discriminating is in batch mode.

27. The method of claim 16, wherein said carrier medium travels through said chamber according to a velocity profile such that said carrier medium moves more rapidly at the center of said chamber.

28. The method of claim 27, wherein said velocity profile is parabolic.

29. The method of claim 16, wherein said carrier medium travels through said chamber according to a plug-like profile.

30. The method of claim 16, wherein said electrical signal comprises a programmed voltage signal.

31. The method of claim 16, wherein said chamber has a substantially greater width than thickness.

32. A method of discriminating matter utilizing dielectrophoresis and field flow fractionation in a chamber defined by a pair of side walls, a top wall, and a bottom wall, said method comprising:

introducing a carrier medium including said matter into an inlet port of said chamber and directing said carrier medium from said inlet port toward top and bottom outlet ports coupled to said top and bottom walls, respectively;

applying an electrical signal to an electrode element coupled to said chamber to create a spatially inhomogeneous electric field to generate a dielectrophoretic force on said matter having components normal to the direction of said carrier medium;

controlling said spatially inhomogeneous electric field to balance said dielectrophoretic force with a gravitational force on said matter to displace said matter to different heights within said chamber to discriminate said matter;

withdrawing a first portion of said carrier medium from said top outlet port at a first fluid flow rate; and withdrawing a second portion of said carrier medium from said bottom outlet port at a second fluid flow rate.

33. The method of claim 32, further comprising controlling said first and second fluid flow rates to further discriminate said matter.

34. The method of claim 32, further comprising detecting discriminated matter with a detector coupled to said chamber.

35. The method of claim 32, wherein said carrier medium is introduced into said inlet port at a third fluid flow rate, and wherein said first fluid flow rate is less than or equal to said third fluid flow rate.

36. The method of claim 32, wherein said carrier medium is introduced into said inlet port at a third fluid flow rate, and wherein said first fluid flow rate is about one half of said third fluid flow rate.

37. The method of claim 32, wherein said method of discriminating is in continuous mode.

38. The method of claim 32, wherein said method of discriminating is in batch mode.

39. The method of claim 32, wherein said electrical signal comprises a programmed voltage signal.

40. An apparatus for discriminating matter, comprising:

a chamber defined by a top and bottom wall;

an outlet port coupled to said chamber;

an inlet port coupled to said chamber and in spaced relation with outlet port;

an electrode element coupled to said chamber and configured to create a spatially inhomogeneous electric field to generate a dielectrophoretic force on said matter; and two or more sensing electrode elements coupled to said chamber and defining a detector integral with said chamber.

\* \* \* \* \*